(12) United States Patent
Keady

(10) Patent No.: US 12,256,188 B2
(45) Date of Patent: Mar. 18, 2025

(54) EARTIPS AND EARPHONE DEVICES, AND SYSTEMS AND METHODS THEREFORE

(71) Applicant: Earsoft, LLC, Delray Beach, FL (US)

(72) Inventor: John P. Keady, Fairfax Station, VA (US)

(73) Assignee: Earsoft, LLC, Delray Beach, FL (US)

( * ) Notice: Subject to any disclaimer, the term of this patent is extended or adjusted under 35 U.S.C. 154(b) by 0 days.

(21) Appl. No.: 18/215,827

(22) Filed: Jun. 29, 2023

(65) Prior Publication Data

US 2023/0403497 A1    Dec. 14, 2023

Related U.S. Application Data

(63) Continuation of application No. 17/861,820, filed on Jul. 11, 2022, now Pat. No. 11,743,630, which is a
(Continued)

(51) Int. Cl.
*H04R 1/10*    (2006.01)
*A61F 11/08*    (2006.01)
*A61F 11/10*    (2006.01)

(52) U.S. Cl.
CPC ......... *H04R 1/1083* (2013.01); *H04R 1/1016* (2013.01); *H04R 1/1058* (2013.01);
(Continued)

(58) Field of Classification Search
CPC .. A61F 11/085; A61F 11/10; A61F 2250/001; A61F 11/08; H04R 1/1083;
(Continued)

(56) References Cited

U.S. PATENT DOCUMENTS 2,521,414 A    9/1950    Schier et al.
2,803,308 A    8/1957    Mattia
(Continued)

FOREIGN PATENT DOCUMENTS

DE    102012221233    3/2014
DE    102013203334    5/2014
(Continued)

OTHER PUBLICATIONS

UK Examination Report under Section 18(3), Sep. 22, 2021, App. No. GB2015940.6 (attached).
(Continued)

*Primary Examiner* — Brian Ensey
(74) *Attorney, Agent, or Firm* — Akerman LLP; Peter A. Chiabotti; David J. Fernandez-Fidalgo

(57) ABSTRACT

The application discloses an eartip, an earphone device, an earphone housing and a hearbud housing device. The eartip can include an outer portion, an inner portion, and an encapsulated volume formed by the inner and outer portion, wherein the outer portion is designed to contact the ear canal, and wherein the inner portion is designed to fit upon a stent. In an alternative embodiment, the airtip can include an inverted body, wherein when the inverted body is at least partially folded on itself the inverted body is arranged to include a bulbous region sized for insertion in an ear canal, a cavity internal to the bulbous region that holds a gas, where increasing pressure on the bulbous region releases a portion of the gas.

9 Claims, 61 Drawing Sheets

Related U.S. Application Data continuation of application No. 16/979,076, filed as application No. PCT/US2019/021508 on Mar. 9, 2019, now Pat. No. 11,638,084.

(60) Provisional application No. 62/790,427, filed on Jan. 9, 2019, provisional application No. 62/696,682, filed on Jul. 11, 2018, provisional application No. 62/685,271, filed on Jun. 14, 2018, provisional application No. 62/681,083, filed on Jun. 5, 2018, provisional application No. 62/676,280, filed on May 25, 2018, provisional application No. 62/666,026, filed on May 2, 2018, provisional application No. 62/640,967, filed on Mar. 9, 2018.

(52) U.S. Cl.
CPC ............. *A61F 11/085* (2022.01); *A61F 11/10* (2013.01); *H04R 2460/09* (2013.01)

(58) Field of Classification Search
CPC .................... H04R 1/1016; H04R 1/1058; H04R 2460/09; H04R 1/2807; H04R 25/656; H04R 2225/77; H04R 1/1066
See application file for complete search history.

(56) References Cited

U.S. PATENT DOCUMENTS

| | | | |
|---|---|---|---|
| 4,852,683 A * | 8/1989 | Killion | A61F 11/10 |
| | | | 181/135 |
| 5,781,638 A | 7/1998 | Hosaka et al. | |
| 6,094,494 A | 6/2000 | Haroldson | |
| 6,513,621 B1 | 2/2003 | Deslauriers et al. | |
| 7,130,437 B2 | 10/2006 | Stonikas et al. | |
| 8,047,207 B2 | 11/2011 | Perez et al. | |
| 8,061,472 B2 * | 11/2011 | Tiemens | C08J 9/0061 |
| | | | 181/135 |
| 8,186,478 B1 | 5/2012 | Grason | |
| 8,229,128 B2 | 7/2012 | Keady | |
| 8,251,925 B2 | 8/2012 | Staab et al. | |
| 8,391,534 B2 | 3/2013 | Ambrose et al. | |
| 8,522,916 B2 | 9/2013 | Keady | |
| 8,548,181 B2 | 10/2013 | Kraemer | |
| 8,631,801 B2 | 1/2014 | Keady | |
| 8,649,540 B2 | 2/2014 | Killion et al. | |
| 8,678,011 B2 | 3/2014 | Goldstein et al. | |
| 8,774,435 B2 | 7/2014 | Ambrose et al. | |
| 8,792,669 B2 | 7/2014 | Harsch | |
| 8,903,113 B2 | 12/2014 | Gebert | |
| 8,942,405 B2 | 1/2015 | Jones et al. | |
| 9,288,592 B2 | 3/2016 | Basseas | |
| 9,338,568 B2 | 5/2016 | van Hal | |
| 9,462,100 B2 | 10/2016 | Usher et al. | |
| 10,045,107 B2 | 8/2018 | Kirsch et al. | |
| 10,506,320 B1 | 12/2019 | Lott | |
| 10,917,711 B2 | 2/2021 | Higgins | |
| 11,006,198 B2 | 5/2021 | Lott | |
| 11,012,770 B2 | 5/2021 | Hatfield et al. | |
| 11,294,619 B2 | 4/2022 | Usher et al. | |
| 2004/0258263 A1 | 12/2004 | Saxton et al. | |
| 2007/0221232 A1 | 9/2007 | Jenkins | |
| 2008/0187161 A1 * | 8/2008 | Tiemens | H04R 1/1016 |
| | | | 381/380 |
| 2009/0101433 A1 | 4/2009 | Stiehl et al. | |
| 2011/0079227 A1 | 4/2011 | Turncot et al. | |
| 2013/0136285 A1 | 5/2013 | Naumann | |
| 2013/0251172 A1 | 9/2013 | Mosseri | |
| 2014/0205123 A1 | 7/2014 | Lafort et al. | |
| 2016/0050483 A1 | 2/2016 | Kulavik et al. | |
| 2016/0057528 A1 | 2/2016 | Trine et al. | |
| 2016/0127818 A1 | 5/2016 | Ambrose | |
| 2016/0295311 A1 | 10/2016 | Keady et al. | |
| 2018/0220239 A1 | 8/2018 | Keady et al. | |
| 2019/0387305 A1 | 12/2019 | Keady | |
| 2021/0152924 A1 | 5/2021 | Keady | |
| 2022/0061767 A1 | 3/2022 | Goldstein et al. | |

FOREIGN PATENT DOCUMENTS

| | | |
|---|---|---|
| EP | 1841283 | 10/2007 |
| EP | 2749043 | 7/2014 |
| EP | 2991381 | 4/2019 |
| EP | 3068142 | 9/2019 |
| FR | 2560520 | 9/1985 |
| JP | 2017147677 A | 8/2017 |
| KR | 101194923 B1 | 10/2012 |
| WO | WO2019081650 | 5/2019 |

OTHER PUBLICATIONS

Office Action in Korean Patent Application No. 10-2020-7028874, Issued May 16, 2023, with translation.

\* cited by examiner

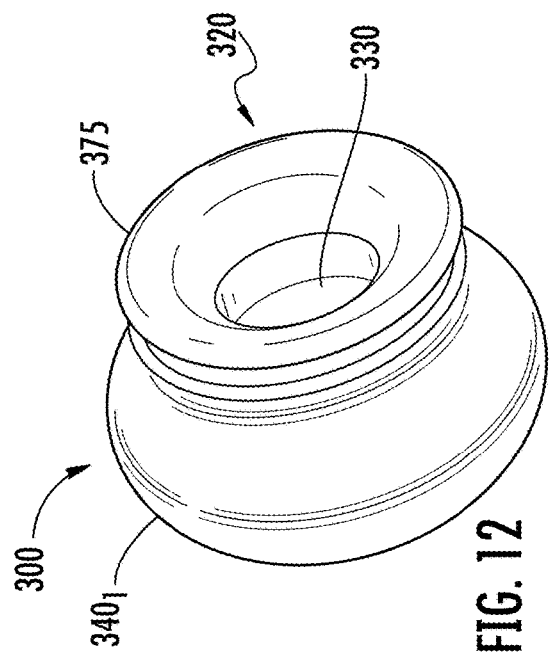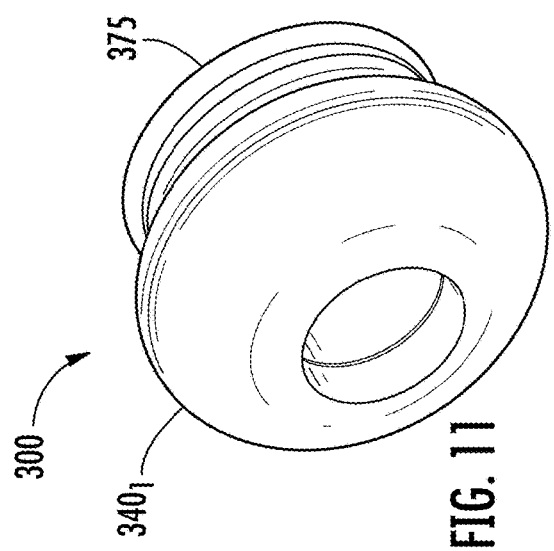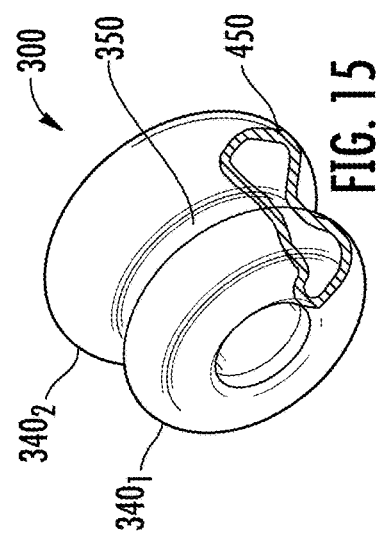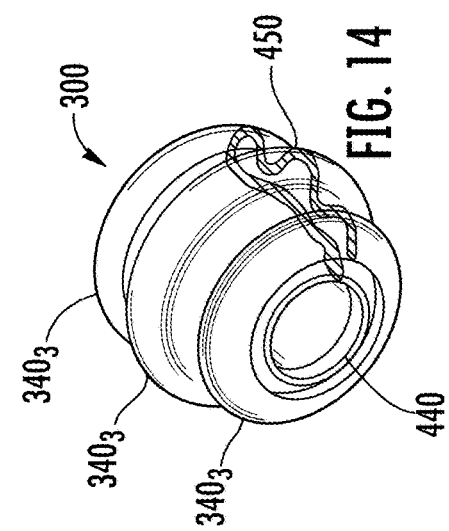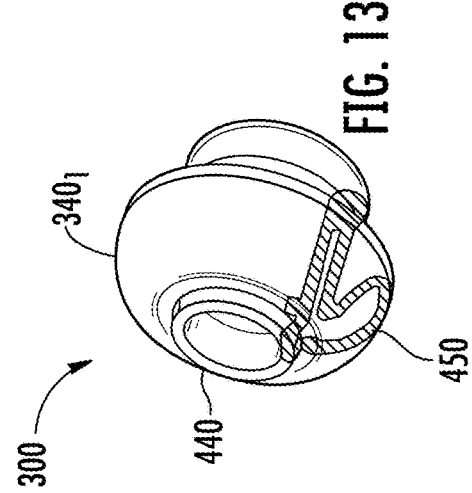

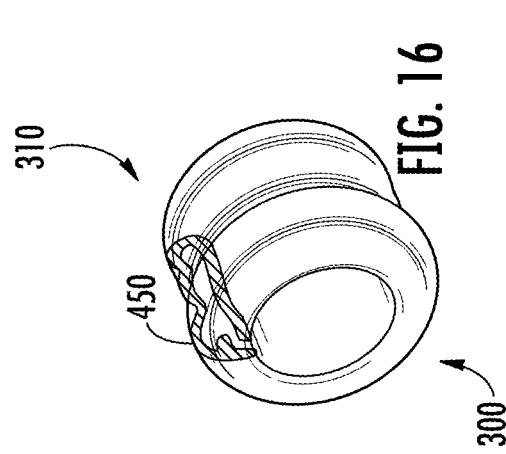
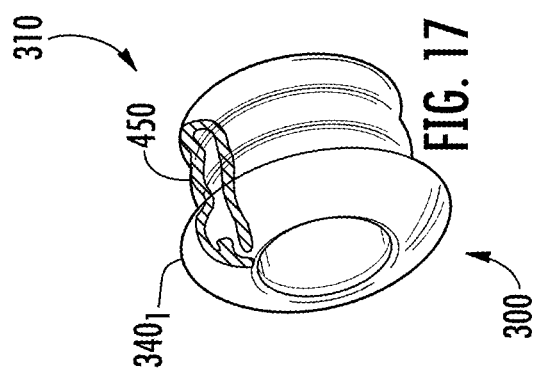
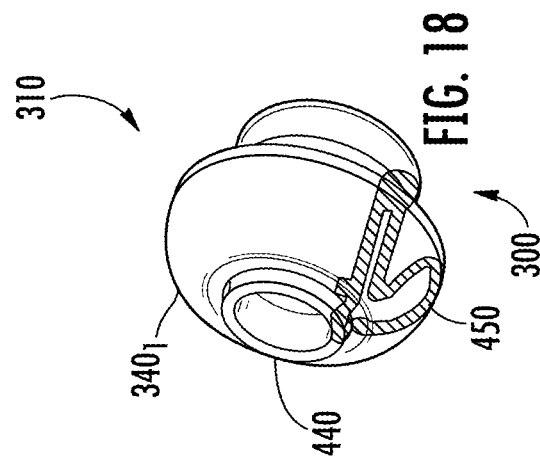

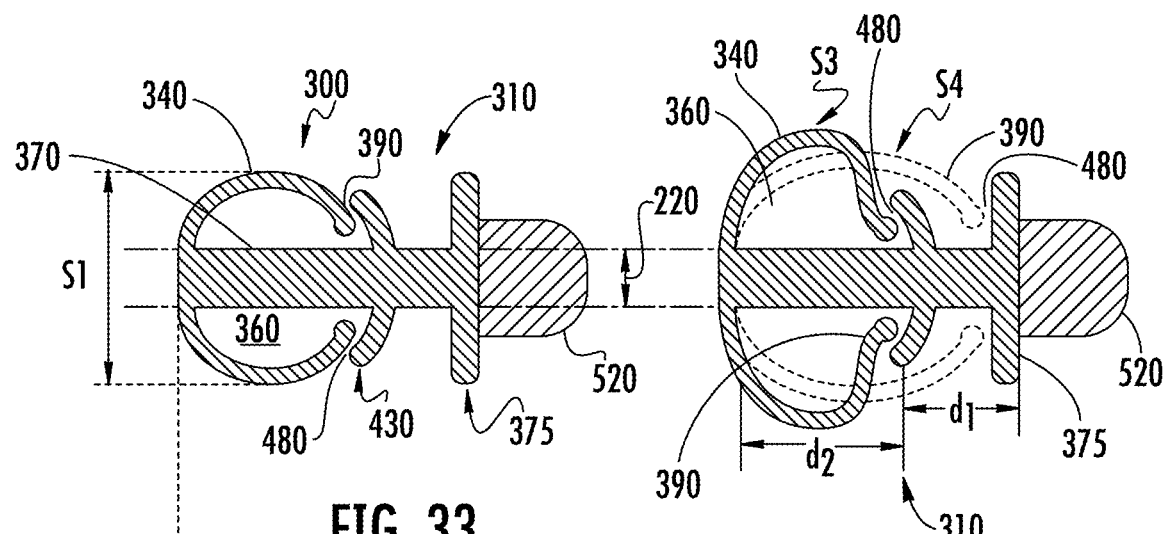
FIG. 33
FIG. 34A
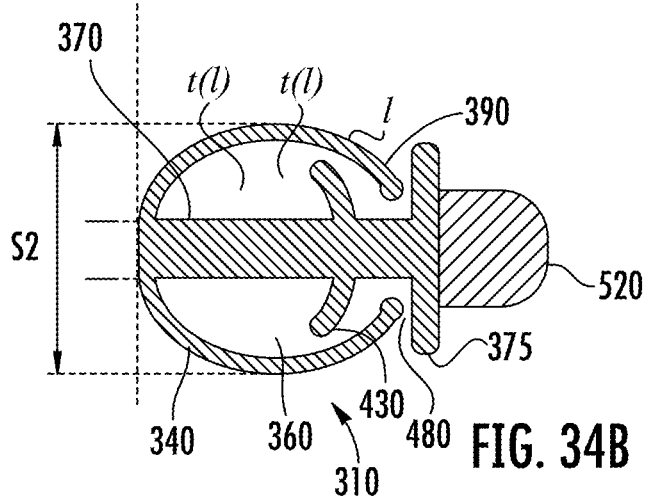
FIG. 34B
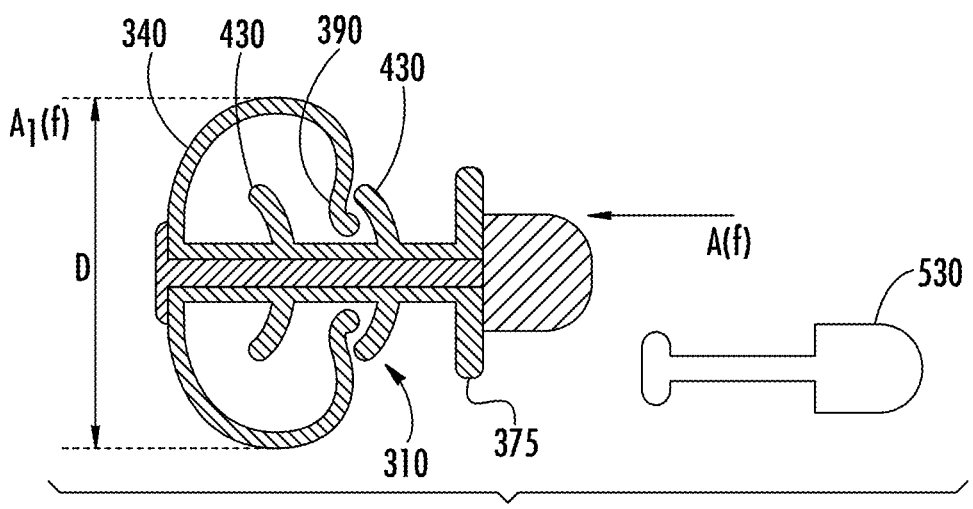
FIG. 35

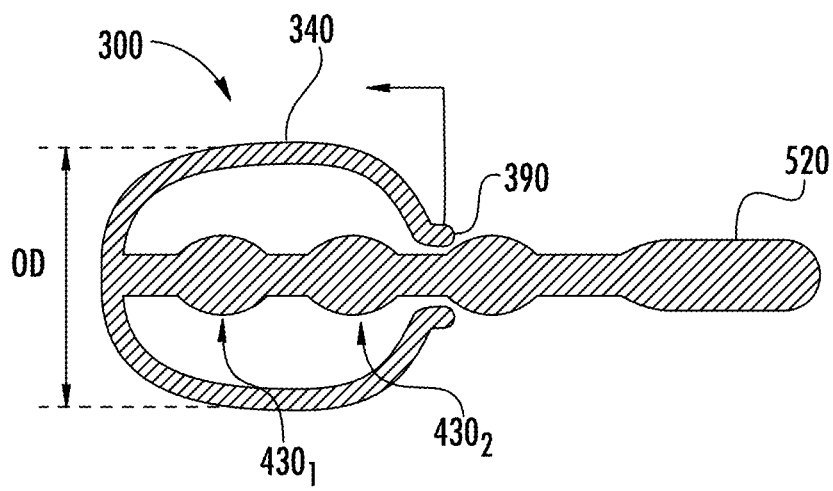
FIG. 42
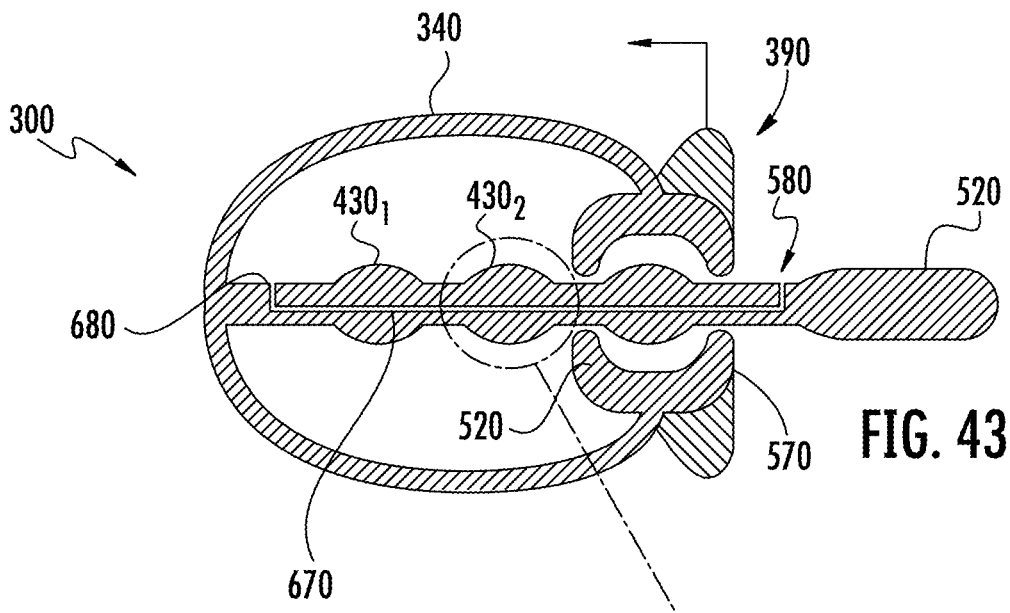
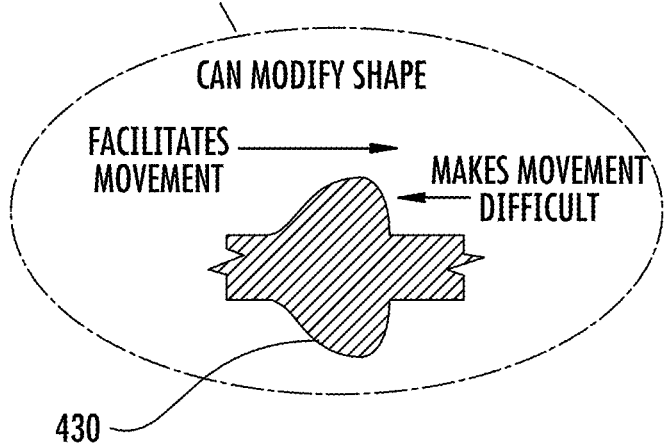
FIG. 43

OPTIONAL 3RD SIZE

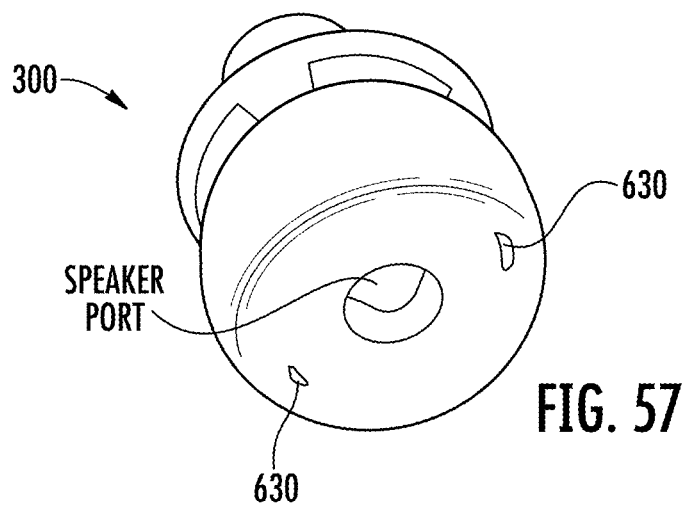
FIG. 57
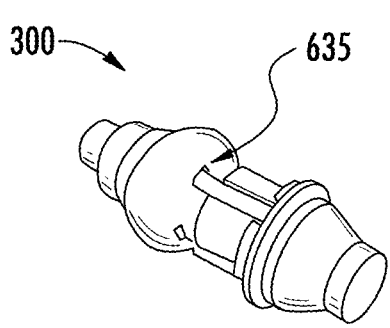
FIG. 58
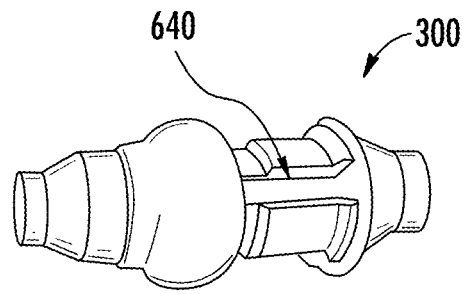
FIG. 59
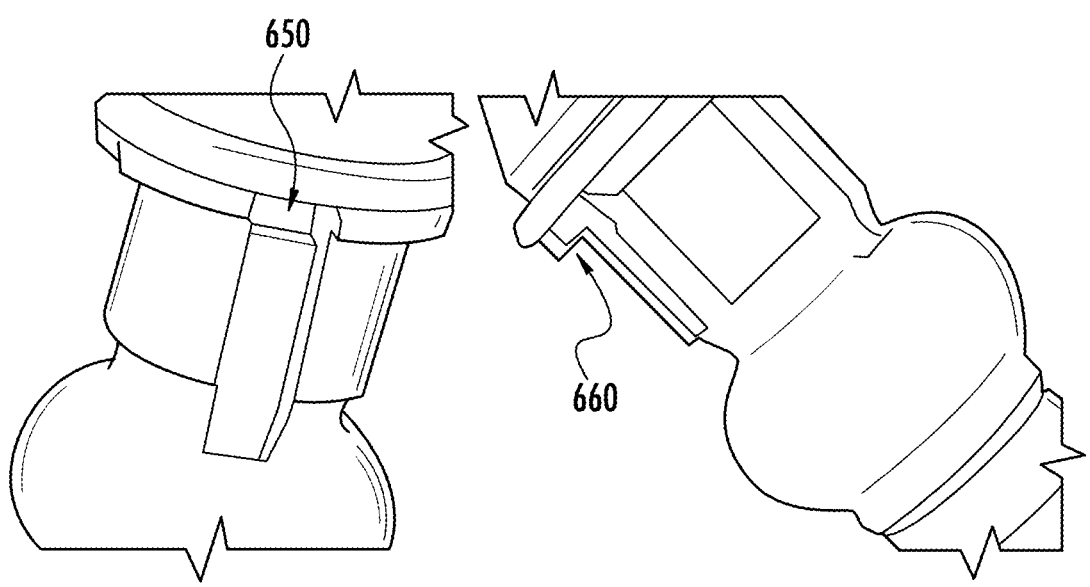
FIG. 60A
FIG. 60B

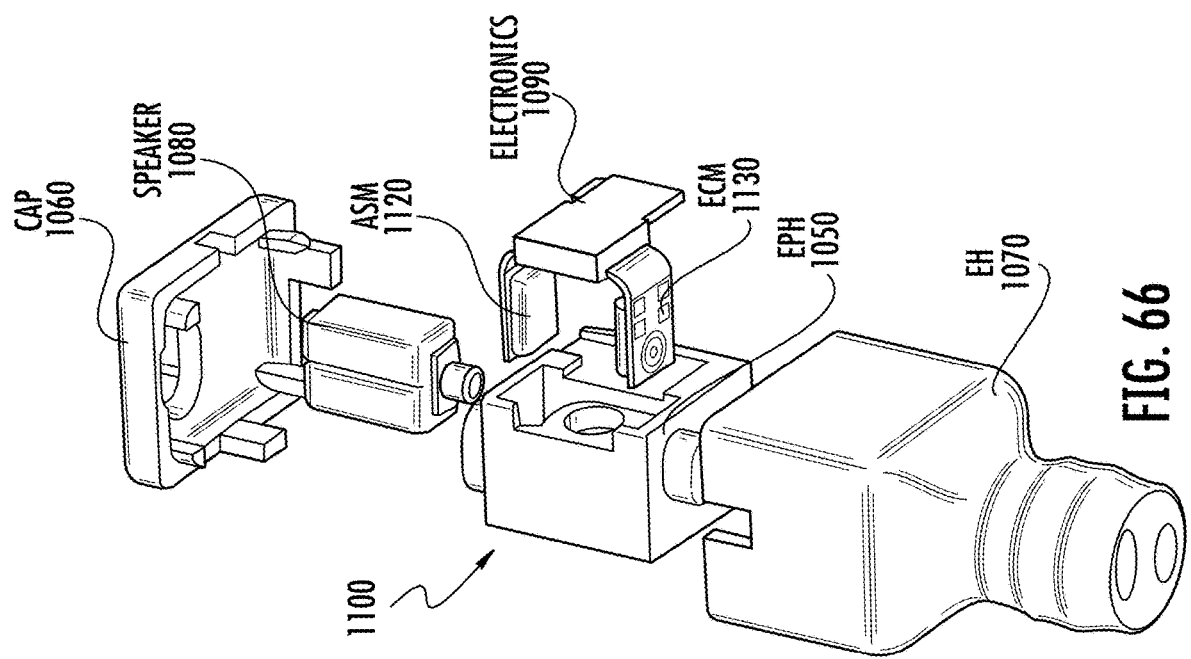
FIG. 66
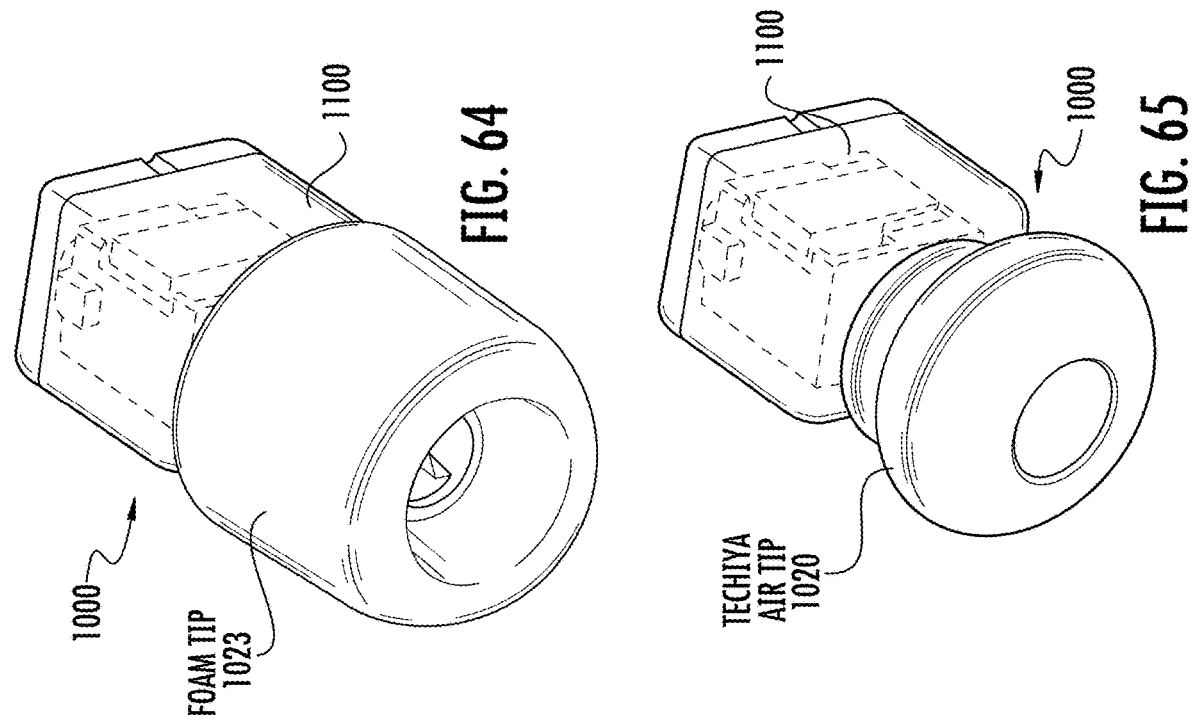
FIG. 64
FIG. 65

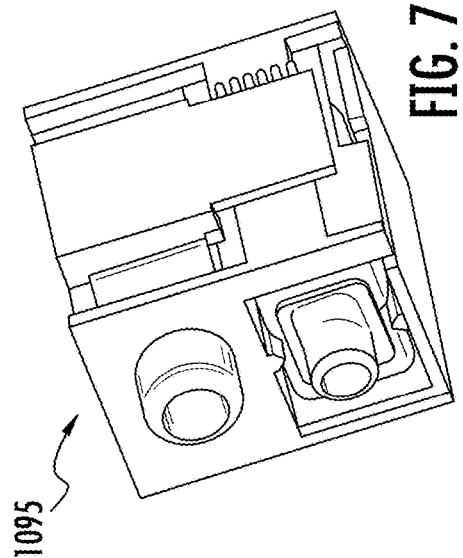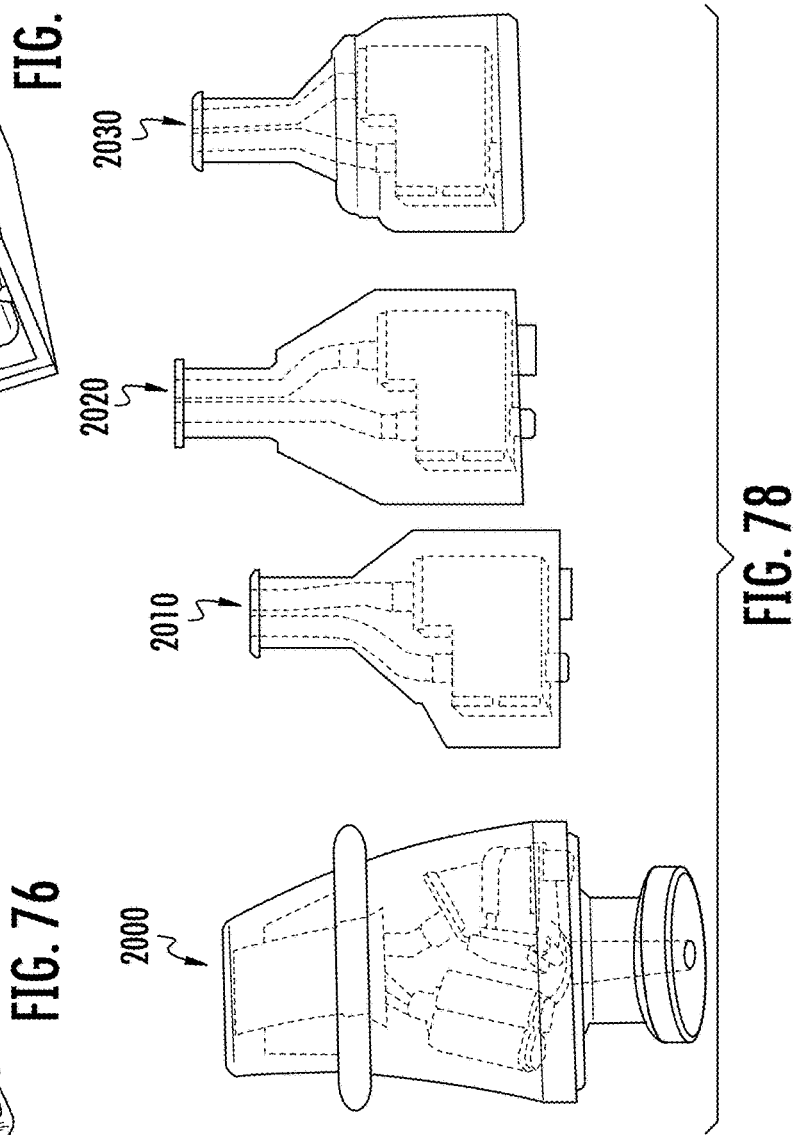
FIG. 77
FIG. 76
FIG. 78

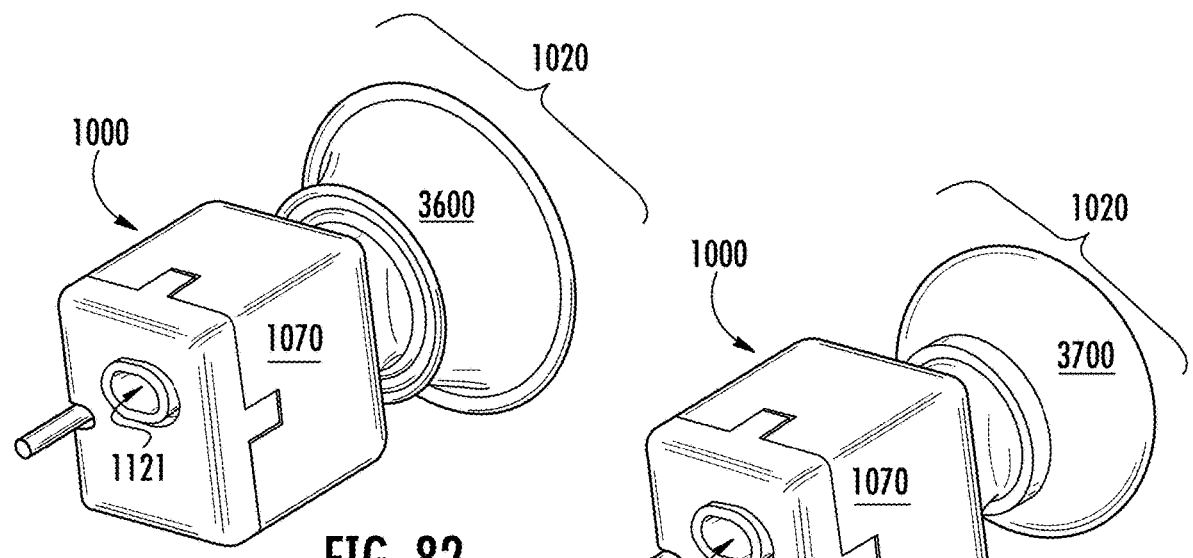
FIG. 82
FIG. 83
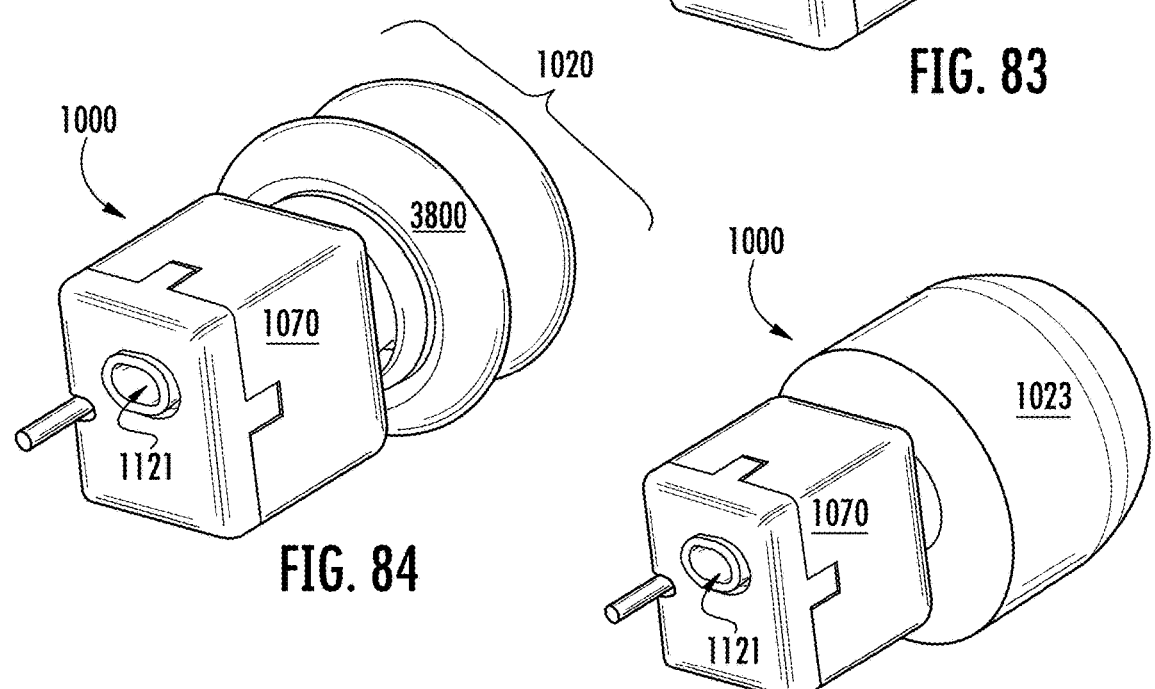
FIG. 84
FIG. 85

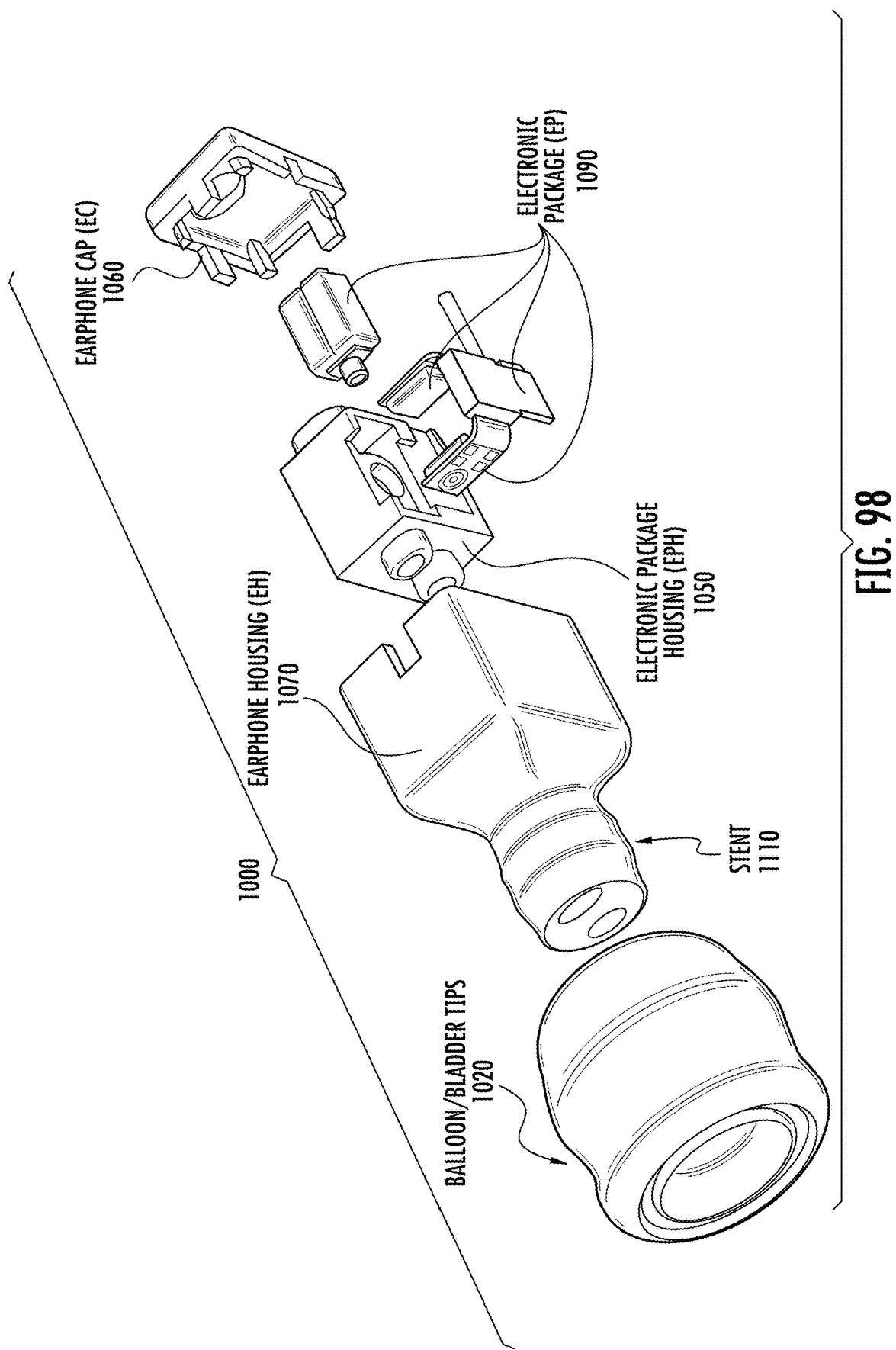

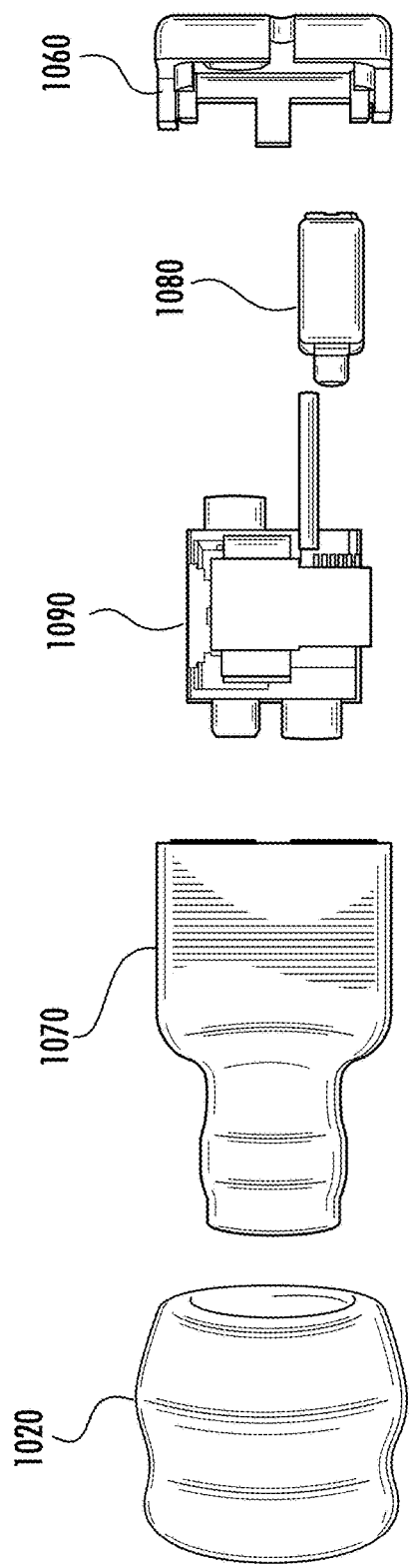
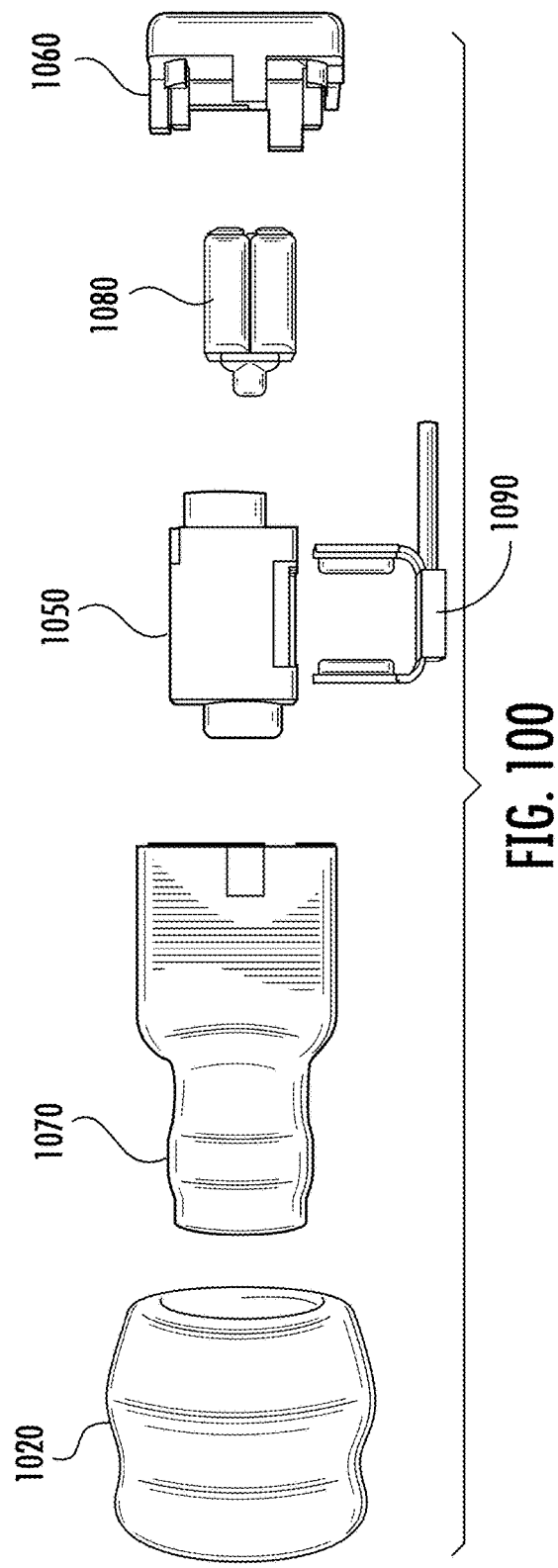

| 1/3 OCTAVE BAND CENTER (Hz) | 125 | 250 | 500 | 1000 | 2000 | 3150 | 4000 | 6300 | 8000 |
|---|---|---|---|---|---|---|---|---|---|
| MEAN ATTENUATION (dB) | 23.7 | 24.8 | 23.1 | 23.5 | 31.1 | 36.2 | 35.3 | 31.2 | 32.5 |
| STANDARD DEVIATION (dB) | 3.2 | 3.6 | 4.7 | 2.4 | 3.7 | 3.9 | 3.9 | 3.4 | 3.9 |

EARTIPS AND EARPHONE DEVICES, AND SYSTEMS AND METHODS THEREFORE

CROSS REFERENCE TO RELATED APPLICATIONS AND PRIORITY

This application is a continuation of and claims priority to U.S. patent application Ser. No. 17/861,820, filed 11 Jul. 2022, which is a continuation of and claims priority to U.S. patent application Ser. No. 16/979,076, filed 11 Jul. 2022, now U.S. Pat. No. 11,638,084, which is a National Phase of and claims priority to PCT/US19/21508, filed 9 Mar. 2019, which claims priority to U.S. Provisional Patent Application No. 62/640,967, filed Mar. 9, 2018, U.S. Provisional Patent Application No. 62/666,026, filed May 2, 2018, U.S. Provisional Patent Application No. 62/676,280, filed May 25, 2018, U.S. Provisional Patent Application No. 62/681,083, filed Jun. 5, 2018, U.S. Provisional Patent Application No. 62/685,271, filed Jun. 14, 2018, U.S. Provisional Patent Application No. 62/696,682, filed Jul. 11, 2018, U.S. Provisional Patent Application No. 62/790,427, Jan. 9, 2019, the entireties of which are hereby incorporated by reference.

FIELD OF THE APPLICATION

The present application relates to devices that modify acoustic signals, and more particularly, though not exclusively, devices that can be used in the ear.

BACKGROUND

Many devices have been developed over time to deliver acoustic content to a user. Many of these devices take the form of an earphone (a device to deliver audio content directly to the ear, e.g., muff, earbud, in-ear system, hearing aid), which can be connected either wired or wireless to a computational device which delivers content or standalone (e.g., hearing aid). Most designs of earphones have electrical components that are uniquely oriented for a particular form factor and not easily transferrable to other form factors. In essence the electronics are often forced into a form factor rather than a smallest electrical package developed and the form factor developed around the package. Additionally when the earphone has a component that is at least partially inserted into the ear canal, comfort can be an issue in prolonged use.

Ease of manufacturing and enhanced comfortable use of earphones are some of the issues to be resolved.

Also, hearing protection can take several forms such as earplugs and muffs. Such hearing protection devices attenuate acoustic energy before it reaches the eardrum (tympanum) by creating an insertion loss that is achieved by reflection of the sound waves, dissipation with the device's structure, impedance of the waves through tortuous paths, closing of acoustical valves, and other means. For a hearing protector, the amount of sound pressure level (SPL) reduced, usually measured in decibels (dB), is typically depicted graphically as a function of frequency. Most hearing protection fails to deliver a flat attenuation across frequency spectrum, instead typically providing attenuation which increases in dB as frequency increases; therefore, the attenuation spectrum is typically nonlinear, which affects the perception of sound frequencies across the audible spectrum in different degrees. For this reason, pitch perception and other auditory experiences which rely on frequency-based cues can be compromised by the nonlinear attenuation imparted by conventional hearing protectors. This leads to the need for uniform or "flat" attenuation, which is desirable in many situations, for example, musicians would like to conserve their hearing while hearing an accurate frequency representation of the produced music, or workers who must listen for certain spectral characteristics associated with their machinery or environment.

One of the current issues with hearing protection and hearing assistance systems is that the attenuation cannot be tuned for a particular situation.

SUMMARY

Devices, system and methods for eartips, the use of eartips and the manufacture of eartips is disclosed.

The outer portion of an eartip (e.g. outer bulb surface) contacts the ear canal wall when inserted into the ear canal. The inner portion contains a core or channel that can fit on a stent (earphone eartip), while a wider portion aids in insertion onto a stent, or if used as an earplug the core or channel will be at least partially filled in or blocked. Prior to insertion into an ear canal the outer portion and inner portion encapsulate or receive a structure (Eartip membrane contacts a structure (e.g., stent part, ledge-movable or part of stent), when inserted or as presented (final form after folded from a negative mold)) a medium (e.g., gas, fluid) that can have an opening aiding molding. Note that the opening can be faced inward toward the ear canal or formed to face toward the ambient environment. Note that the stent can be fabricated from various materials (e.g., silicon, urethane, rubber) and can include internal channel (tubes). The stent can also be a multi-lumen (i.e., multi-passageway) stent where the channels/tubes are various lumens of the multi-lumen stent, or solid (e.g., earplug stent). Note that the material of the membrane can have different properties from the stent or membrane wall or channel wall. Upon insertion into an ear canal, the ear canal wall pressure on the outer portion of a ridge and the outer portion can move radially and axially to relieve the pressure pressing against the ear canal wall. This is in contrast to foam tips that will always press back radially dependent upon the amount of deformation of the foam. The combination of radial and axial movement of the outer section helps decrease pressure on the ear canal wall and increase contact area also decreasing pressure for a given retaining force.

In one embodiment, an eartip can have an outer portion, an inner portion, and an encapsulated volume formed by the inner and outer portion, wherein the outer portion is designed to contact the ear canal, and wherein the inner portion is designed to fit upon a stent. The eartip can also have a passage to an ambient environment, where the passage is decreased when the eartip is inserted upon a stent or inserted into an ear canal. Also, the encapsulated volume may be at a pressure that is reduced when pressure on the outer surface exceeds a threshold value.

In another embodiment, an eartip may have an inverted body, where when the inverted body is at least partially folded on itself the inverted body is arranged to a bulbous region sized for insertion in an ear canal, a cavity internal to the bulbous region that holds a gas or enclosed volume, where increasing pressure on the bulbous region releases a portion of the gas. As such and as disclosed herein, gas can escape from enclosed volume or cavity in the eartip to customize the pressure or force provided by the eartip to provide a snug and comfortable tip without the eartip causing user discomfort from excessive pressure or force. Also, the eartip may have a channel wall that forms the cavity with the bulbous region and that forms a core through a stent can be inserted and/or received.

In one embodiment, the eartip can have a plurality of bulbous regions. Likewise, the eartip can have a plurality of cavities, where each cavity of the plurality of cavities is formed by each bulbous region of the plurality of bulbous regions and the channel wall. The eartip can also include a transition region between the plurality of bulbous regions where the transition region has an concavity that is inverse to the convex surface of the bulbous regions. The eartip can also have a lip extending from the channel wall and a sealing section extending from the bulbous region.

In one embodiment, a sealing tip can be located on the sealing section can be provided. In some arrangements, the cavity is sealed by seating the sealing tip against the channel wall. Also, the can have a material property between 2 Shore A to 90 Shore A. Also, the eartip can be an earplug with a U.S. Environmental Protection Agency (EPA) Noise Reduction Rating (NRR) rating of 3.

Methods of manufacturing a eartip and/or earplug are also disclosed. One method can include printing an eartip as an inverted body, such that when the inverted body is at least partially folded on itself the inverted body is arranged to include one or more of the features disclosed herein. For instance, the eartip can have a bulbous region sized for insertion in an ear canal, a cavity internal to the bulbous region that holds a gas, where increasing pressure on the bulbous region releases a portion of the gas. Further, the method can provide an inverted body eartip with a material property between 2 Shore A to 90 Shore A.

In another embodiment, an earphone system is disclosed. The earphone system can include an earphone and an eartip. The eartip can have structures and functionality described herein.

In another embodiment, a method of forming an eartip is disclosed. The method can include forming a mold of an unfolded shape of an eartip, providing or supplying a flexible material to the mold for a threshold time and temperature for curing to form a cured inverted eartip, removing the cured inverted eartip and folding at least a portion of the cured inverted eartip to form a final eartip. Forming a mold can be skipped if a mold already has been made. Also, folding at least a portion of cured inverted eartip is optional.

In another embodiment, an earphone is disclosed. The earphone can include a housing, where the housing includes a stent configured to accept or insert into various foam tips, flange tips, and eartips. The earphone can also include an electronics package unit, where the electronics package unit includes an electronic package, and an electronic package housing, wherein the electronics package unit is designed to be independent of the housing. The earphone can also include a key, where the key is part of the housing and is designed to fit with the electronic package unit, where the electronic package includes two microphones and a speaker.

In certain embodiments, the outer portion of an eartip (e.g. the outer surface of an eartip) contacts the ear canal wall when inserted into the ear canal. The inner portion contains a core that can fit on a stent, while a wider portion (inside funnel shape of a ridge) aids in insertion onto a stent. Prior to insertion into an ear canal the outer portion and inner portion encapsulates a medium (e.g., gas, fluid) that can have an opening aiding molding. Upon insertion onto a stent the inner portion can move flexibly outward decreasing the opening, and/or upon inserting into an ear canal, the ear canal wall can press inward on the outer surface toward the stent moving the outer portion of the ridge inward, decreas-ing the opening. Note that the opening can be faced inward toward the ear canal or formed to face toward the ambient environment. Note that the stent can be fabricated from various materials (e.g., silicon, urethane, rubber) and can include internal channel (tubes). The stent can also be a multi-lumen (i.e., multi-passageway) stent where the channels/tubes are various lumens of the multi-lumen stent. Upon insertion into an ear canal the ear canal wall pressure on the outer portion of a ridge and the outer portion can move radially and axially to relieve the pressure pressing against the ear canal wall. This is in contrast to foam tips that will always press back radially dependent upon the amount of deformation of the foam. The combination of radial and axial movement of the outer section helps decrease pressure on the ear canal wall and increase contact area also decreasing pressure for a given retaining force.

These and other features of the eartip, earplug, earphone systems and methods are described in the following detailed description, drawings, and appended claims.

BRIEF DESCRIPTION OF THE DRAWINGS

FIG. 11 illustrates a front view of another embodiment of an eartip.

FIG. 12 illustrates the back view of the embodiment of an eartip of FIG. 11.

FIG. 13 illustrates another embodiment of an eartip in perspective view with a partial cross section thereof shown in the perspective view.

FIG. 14 illustrates another embodiment of an eartip in perspective view with a partial cross section thereof shown in the perspective view.

FIG. 15 illustrates another embodiment of an eartip in perspective view with a partial cross section thereof shown in the perspective view.

FIG. 16 illustrates another embodiment of an eartip in perspective view with a partial cross section thereof shown in the perspective view.

FIG. 17 illustrates another embodiment of an eartip in perspective view with a partial cross section thereof shown in the perspective view.

FIG. 18 illustrates another embodiment of an eartip in perspective view with a partial cross section thereof shown in the perspective view.

FIG. 33 illustrates a cross sectional view of another embodiment of an eartip.

FIG. 34A illustrates a cross sectional view of another embodiment of an eartip showing the adjustable sizing of the eartip.

FIG. 34B illustrates a cross sectional view of the embodiment of FIG. 34A of an eartip showing the adjustable sizing of the eartip.

FIG. 35 illustrates a cross sectional view of another embodiment of an eartip with an earplug.

FIG. 42 illustrates a cross sectional view of another embodiment of an eartip.

FIG. 43 illustrates a cross sectional view of another embodiment of an eartip.

FIG. 57 illustrates another embodiment of an eartip.

FIG. 58 illustrates another view of eartip of FIG. 57.

FIG. 59 illustrates another view of eartip of FIG. 57.

FIGS. 60A and 60B illustrate a close up of an occlusion effect eartip.

FIG. 64 illustrates an earphone device with a foam tip according to an embodiment of the present disclosure.

FIG. 65 illustrates an earphone device with an eartip according to an embodiment of the present disclosure.

FIG. 66 illustrates an additional exploded view of a hearbud housing device of an earphone device according to an embodiment of the present disclosure.

FIG. 76 illustrates a comparison between a typical design dependent component layout with a standardized electronics packaging unit according to an embodiment of the present disclosure.

FIG. 77 illustrates a front view of an electronics packaging unit according to an embodiment of the present disclosure.

FIG. 78 illustrates a comparison of an earphone device along with three different earphone housing designs for use with the earphone device according to embodiments of the present disclosure.

FIG. 82 illustrates an earphone device with a first type of eartip according to an embodiment of the present disclosure.

FIG. 83 illustrates an earphone device with a second type of eartip according to an embodiment of the present disclosure.

FIG. 84 illustrates an earphone device with a third type of eartip according to an embodiment of the present disclosure.

FIG. 85 illustrates and earphone device with a foam tip according to an embodiment of the present disclosure.

FIG. 95 is an angled back view of an earphone device including an embodiment of an eartip designed to fit on a stent.

FIG. 96 is another angled back view of an earphone device including a different embodiment of an eartip.

FIG. 97 is another angled back view of an earphone device including a further embodiment of an eartip.

FIG. 98 illustrates an exploded view of an earphone device according to an embodiment of the present disclosure.

FIG. 99 illustrates a side exploded view of an earphone device according to an embodiment of the present disclosure.

FIG. 100 illustrates another side exploded view of an earphone device according to an embodiment of the present disclosure.

FIG. 101 illustrates an angled back exploded view of an earphone device according to an embodiment of the present disclosure.

FIG. 102 illustrates an angled front exploded view of an earphone device according to an embodiment of the present disclosure.

FIG. 103 illustrates an angled bottom exploded view of an earphone device according to an embodiment of the present disclosure.

FIG. 104 illustrates an angled front exploded view of an earphone device according to an embodiment of the present disclosure.

FIG. 105 illustrates an angled back exploded view of an earphone device according to an embodiment of the present disclosure.

FIG. 106 illustrates an angled rear view of an electronic package housing for use with an earphone device according to an embodiment of the present disclosure.

Figure 107:
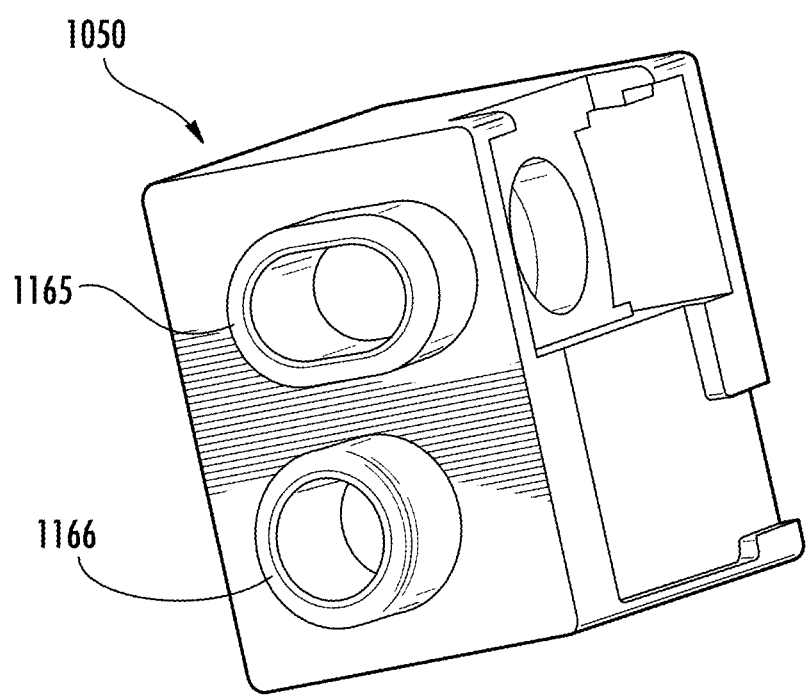
Figure 108:
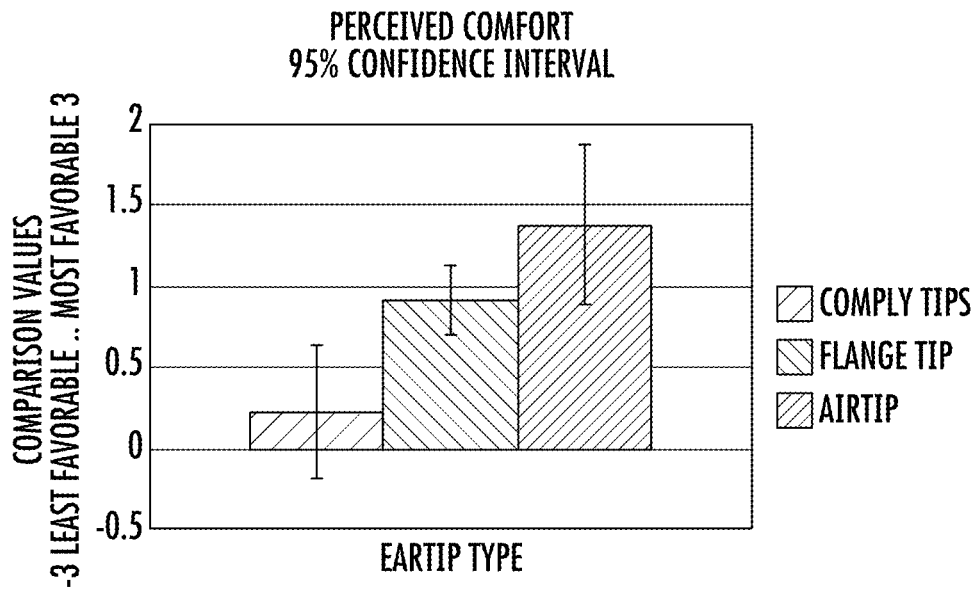
Figure 109:
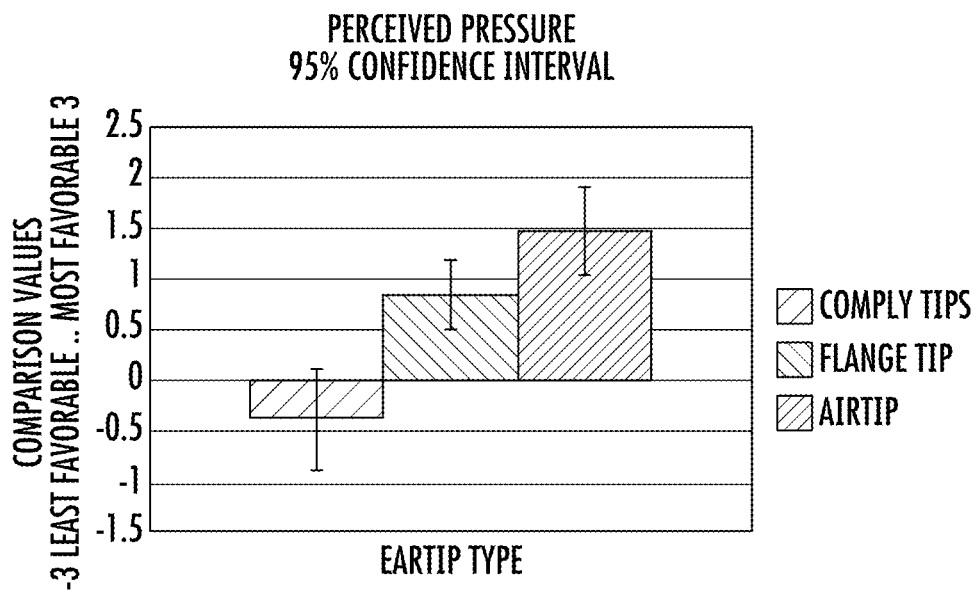
Figure 110:
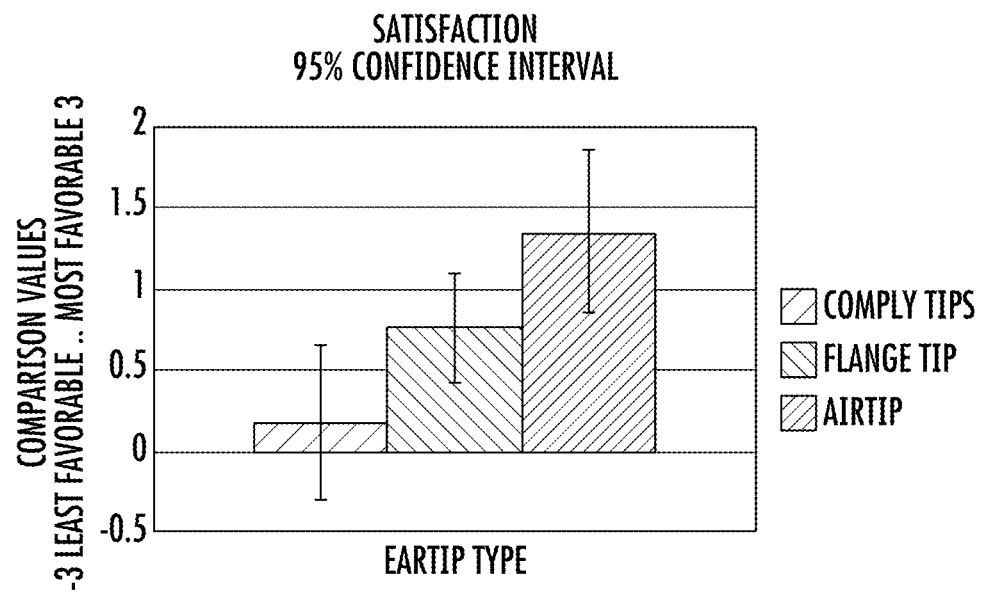
Figure 111:
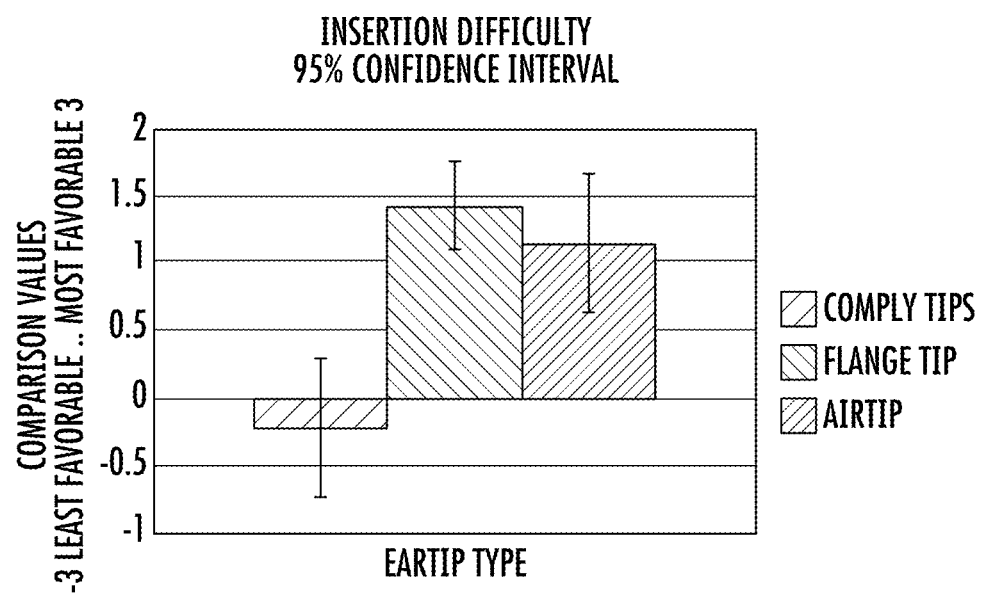

FIG. 107 illustrates an angled front view of an electronic package housing for use with an earphone device according to an embodiment of the present disclosure.

FIGS. 108-111 illustrate test results.

Figures 112, 113:
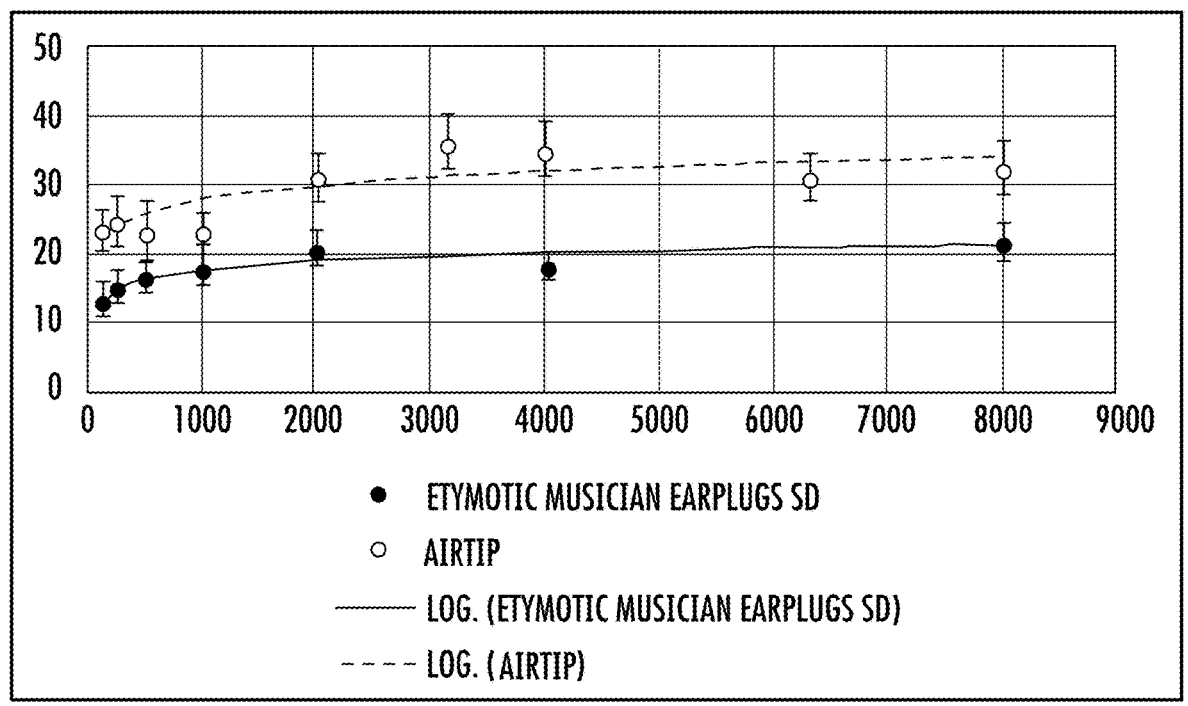

FIG. 112 sets forth U.S. Environmental Protection Agency (EPA) Noise Reduction Rating (NRR) attenuation test data for an eartip.

FIG. 113 illustrates the eartip mean attenuation profile in comparison with a market advertised flat attenuation earplug.

Figure 114:
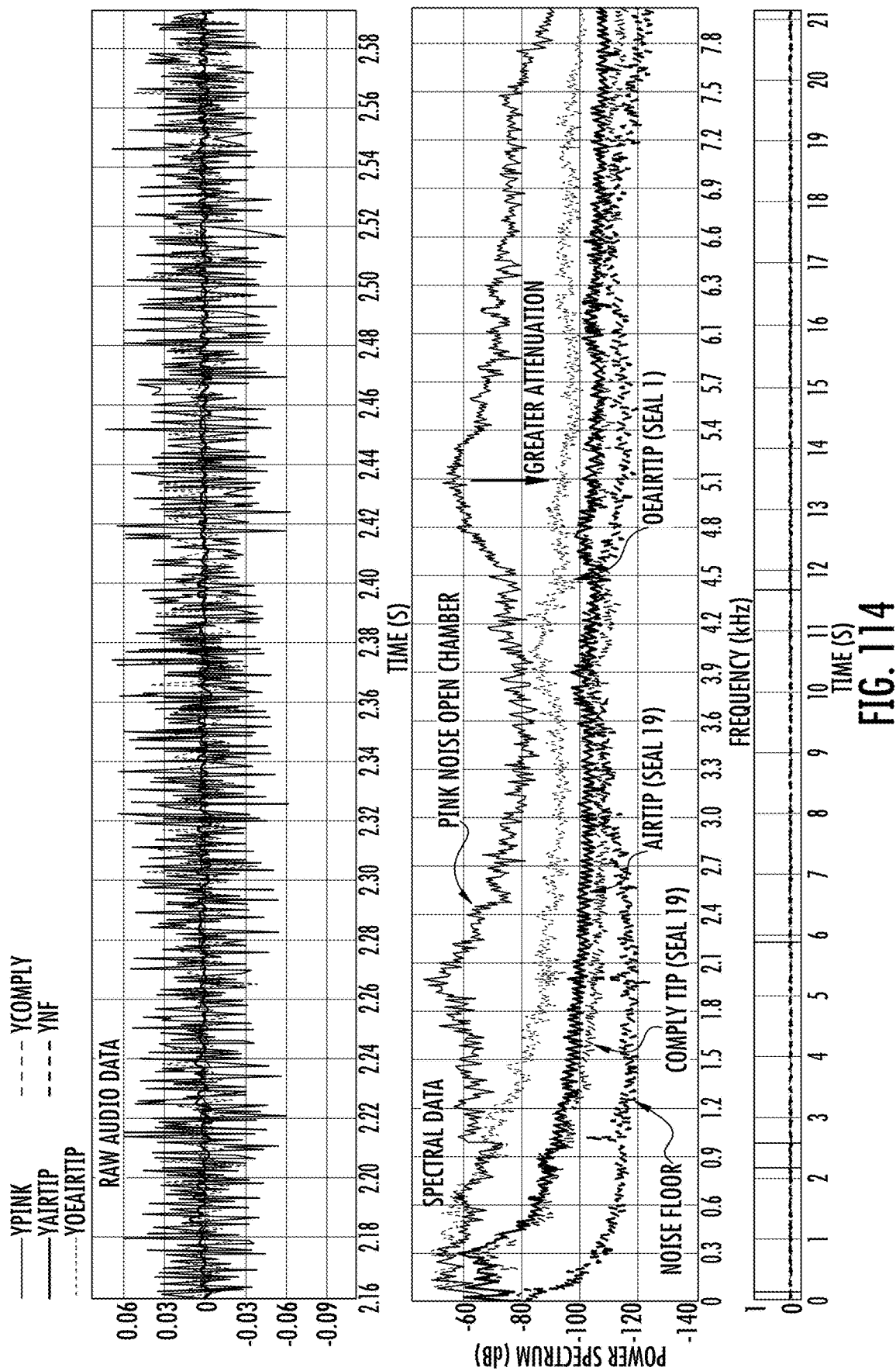
Figure 115:
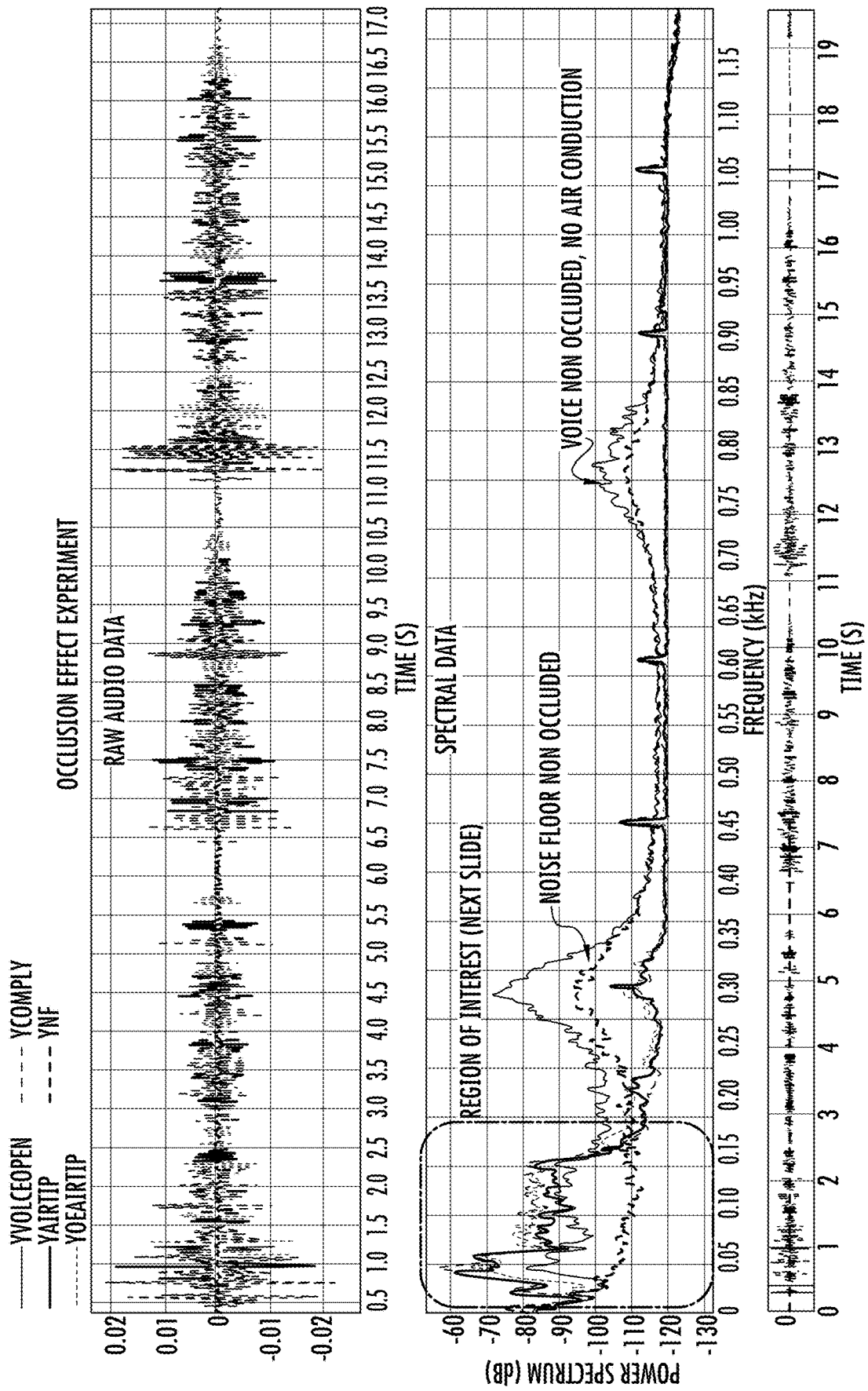
Figure 116:
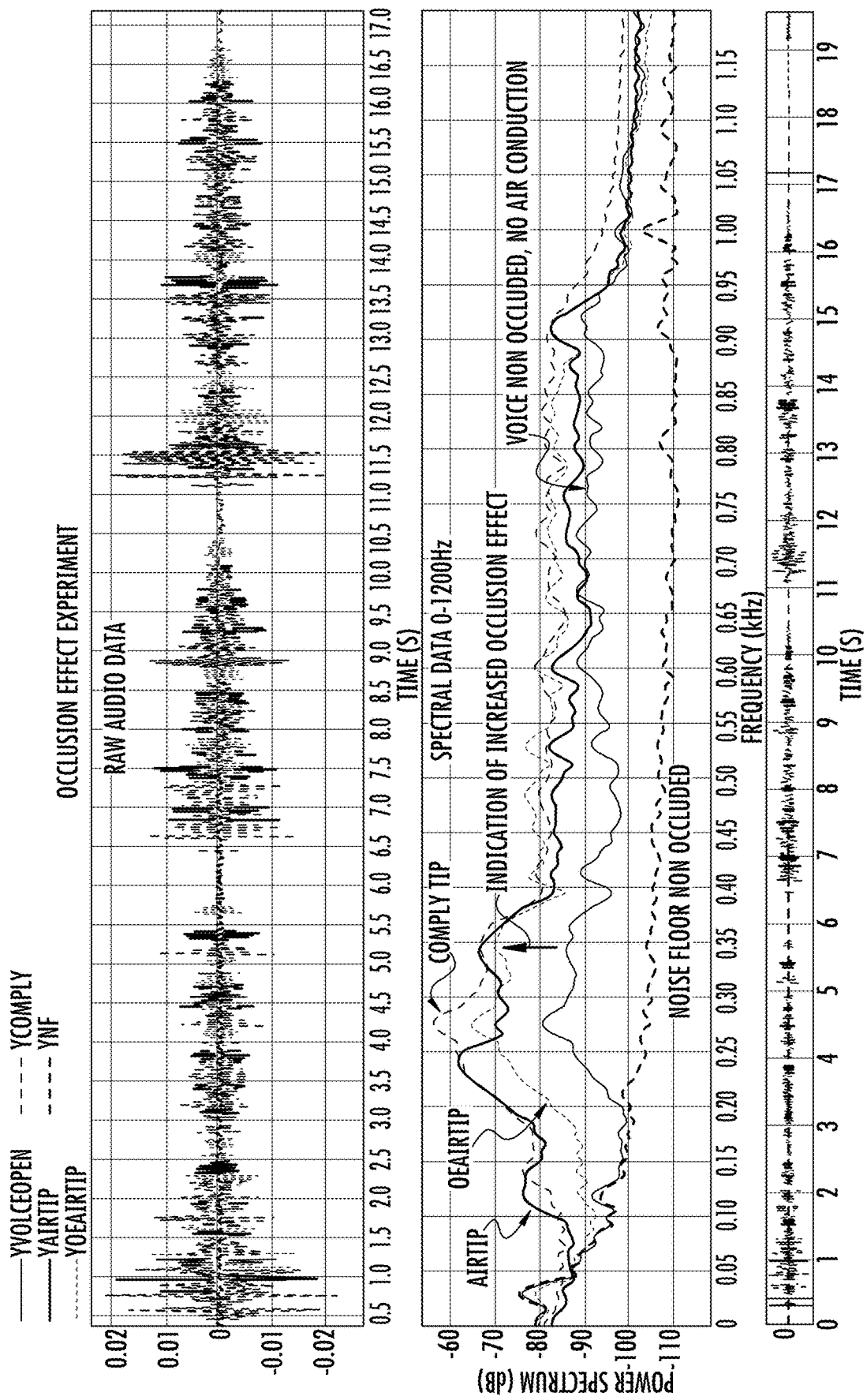

FIGS. 114-116 illustrate an acoustic spectrum which illustrates that the attenuation of occlusion effect eartips.

Figure 117:
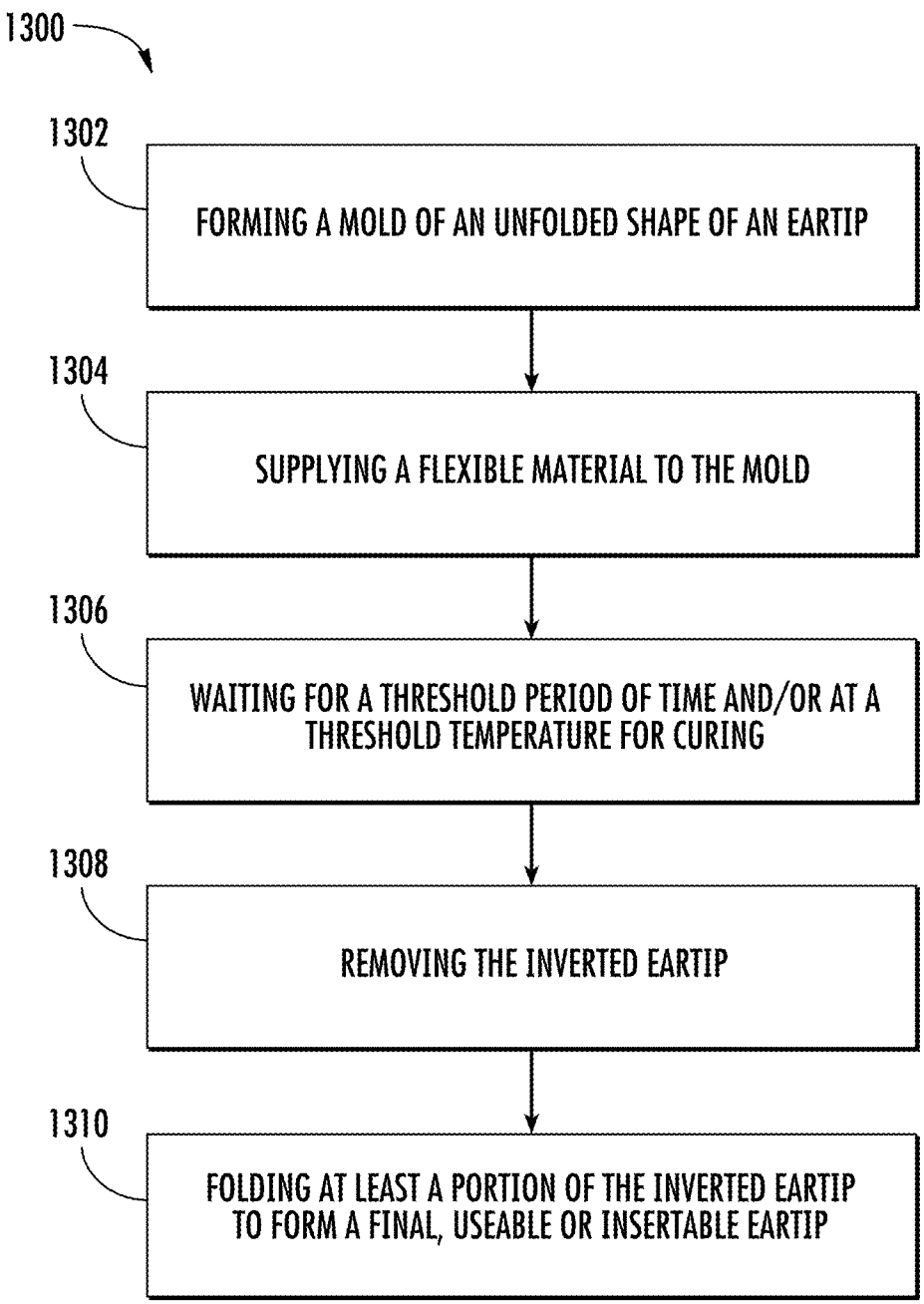

FIG. 117 a flow chart of a method of manufacturing an eartip.

Figure 118:
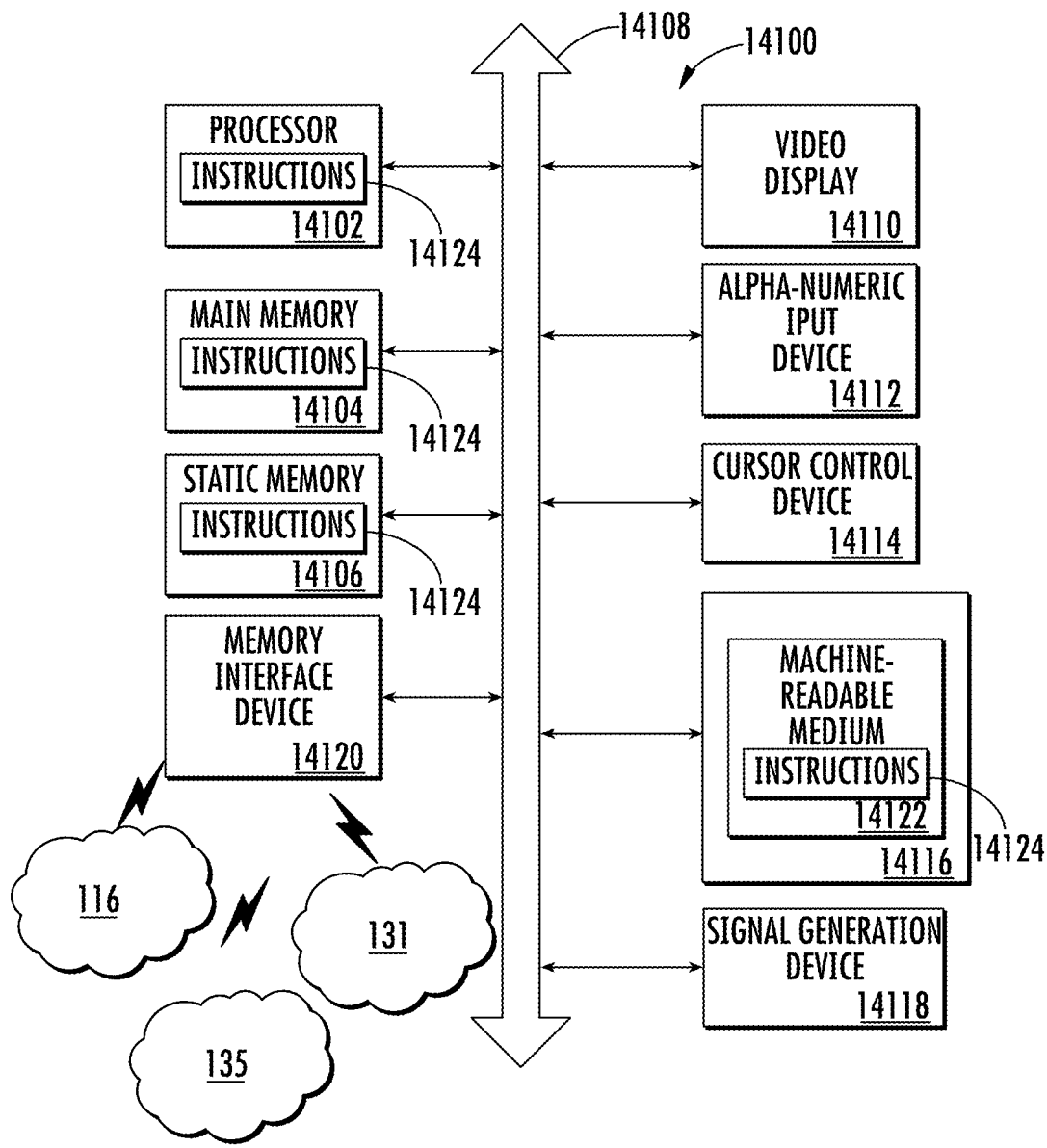

FIG. 118 is a schematic diagram of a machine in the form of a computer system within which a set of instructions, when executed, may cause the machine to perform any one or more of the methodologies or operations of the systems and methods for utilizing an eartip according to embodiments of the present disclosure.

DETAILED DESCRIPTION OF THE INVENTION

Exemplary embodiments of eartips and earphone devices, and systems and methods therefore are disclosed. The eartips are self-adjusting for the variable sizes of user anatomy. In use, the eartip can adjust radially and/or linearly for maximum comfort with a maintenance force that is less than an insertion force. The structural configuration of the eartip provides such adjustability while providing a flatter high frequency attenuation profile that maintains audio quality in comparison to traditional ear buds. Further, such adjustability is provided for with improved manufacturing techniques Exemplary embodiments are directed to or can be operatively used on various passive eartips for hearing protection or electronic wired or wireless earpiece devices (e.g., hearing aids, ear monitors, headphones, ear terminal, behind the ear devices or other acoustic devices as known by one of ordinary skill, and equivalents). For example, the earpieces can have one or more transducers (e.g. ambient sound microphone (ASM), ear canal microphone (ECM), ear canal receiver (ECR/SPKR)) for monitoring/providing sound. In all of the examples illustrated and discussed herein, any specific values should be interpreted to be illustrative only and non-limiting. Thus, other examples of the exemplary embodiments could have different values.

Figure 1:
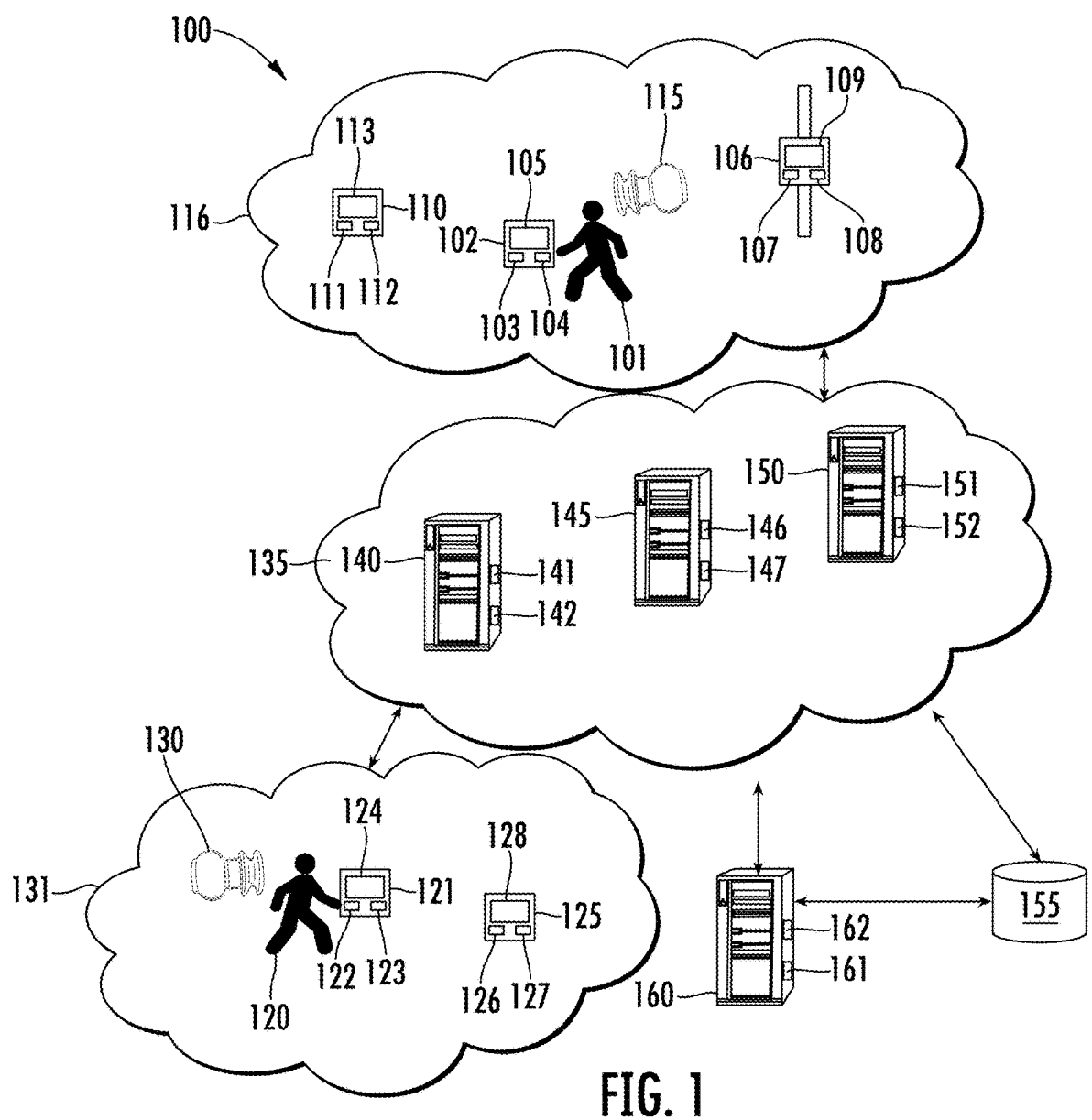
FIG. 1 is a schematic diagram of a system for utilizing eartips according to an embodiment of the present disclosure.

As shown in FIG. 1, a system 100 and methods for utilizing eartips and/or earphone devices are disclosed.

The system 100 may be configured to support, but is not limited to supporting, data and content services, audio processing applications and services, audio output and/or input applications and services, applications and services for transmitting and receiving audio content, authentication applications and services, computing applications and services, cloud computing services, internet services, satellite services, telephone services, software as a service (SaaS) applications, platform-as-a-service (PaaS) applications, gaming applications and services, social media applications and services, productivity applications and services, voice-over-internet protocol (VoIP) applications and services, speech-to-text translation applications and services, interactive voice applications and services, mobile applications and services, and any other computing applications and services. The system may include a first user 101, who may utilize a first user device 102 to access data, content, and applications, or to perform a variety of other tasks and functions. As an example, the first user 101 may utilize first user device 102 to access an application (e.g. a browser or a mobile application) executing on the first user device 102 that may be utilized to access web pages, data, and content associated with the system 100. In certain embodiments, the first user 101 may be any type of user that may potentially desire to listen to audio content, such as from, but not limited to, a music playlist accessible via the first user device 102, a telephone call that the first user 101 is participating in, audio content occurring in an environment in proximity to the first user 101, any other type of audio content, or a combination thereof. For example, the first user 101 may be an individual that may be participating in a telephone call with another user, such as second user 120.

The first user device 102 utilized by the first user 101 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include an interface 105 (e.g. screen, monitor, graphical user interface, etc.) that may enable the first user 101 to interact with various applications executing on the first user device 102, to interact with various applications executing within the system 100, and to interact with the system 100 itself. In certain embodiments, the first user device 102 may include any number of transducers, such as, but not limited to, microphones, speakers, any type of audio-based transducer, any type of transducer, or a combination thereof. In certain embodiments, the first user device 102 may be a computer, a laptop, a tablet device, a phablet, a server, a mobile device, a smartphone, a smart watch, and/or any other type of computing device. Illustratively, the first user device 102 is shown as a mobile device in FIG. 1. The first user device 102 may also include a global positioning system (GPS), which may include a GPS receiver and any other necessary components for enabling GPS functionality, accelerometers, gyroscopes, sensors, and any other componentry suitable for a mobile device.

In addition to using first user device 102, the first user 101 may also utilize and/or have access to a second user device 106 and a third user device 110. As with first user device 102, the first user 101 may utilize the second and third user devices 106, 110 to transmit signals to access various online services and content. The second user device 106 may include a memory 107 that includes instructions, and a processor 108 that executes the instructions from the memory 107 to perform the various operations that are performed by the second user device 106. In certain embodiments, the processor 108 may be hardware, software, or a combination thereof. The second user device 106 may also include an interface 109 that may enable the first user 101 to interact with various applications executing on the second user device 106 and to interact with the system 100. In certain embodiments, the second user device 106 may include any number of transducers, such as, but not limited to, microphones, speakers, any type of audio-based transducer, any type of transducer, or a combination thereof. In certain embodiments, the second user device 106 may be and/or may include a computer, any type of sensor, a laptop, a set-top-box, a tablet device, a phablet, a server, a mobile device, a smartphone, a smart watch, and/or any other type of computing device. Illustratively, the second user device 102 is shown as a smart watch device in FIG. 1.

The third user device 110 may include a memory 111 that includes instructions, and a processor 112 that executes the instructions from the memory 111 to perform the various operations that are performed by the third user device 110. In certain embodiments, the processor 112 may be hardware, software, or a combination thereof. The third user device 110 may also include an interface 113 that may enable the first user 101 to interact with various applications executing on the second user device 106 and to interact with the system 100. In certain embodiments, the third user device 110 may include any number of transducers, such as, but not limited to, microphones, speakers, any type of audio-based transducer, any type of transducer, or a combination thereof. In certain embodiments, the third user device 110 may be and/or may include a computer, any type of sensor, a laptop, a set-top-box, a tablet device, a phablet, a server, a mobile device, a smartphone, a smart watch, and/or any other type of computing device. Illustratively, the third user device 110 is shown as a smart watch device in FIG. 1.

The first, second, and/or third user devices 102, 106, 110 may belong to and/or form a communications network 116. In certain embodiments, the communications network 116 may be a local, mesh, or other network that facilitates communications among the first, second, and/or third user devices 102, 106, 110 and/or any other devices, programs, and/or networks of system 100 or outside system 100. In certain embodiments, the communications network 116 may be formed between the first, second, and third user devices 102, 106, 110 through the use of any type of wireless or other protocol and/or technology. For example, the first, second, and third user devices 102, 106, 110 may communicate with one another in the communications network 116, such as by utilizing Bluetooth Low Energy (BLE), classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 116 may be configured to communicatively link with and/or communicate with any other network of the system 100 and/or outside the system 100.

The system 100 may also include an earphone device 115, which the first user 101 may utilize to hear and/or audition audio content, transmit audio content, receive audio content, experience any type of content, process audio content, adjust audio content, store audio content, perform any type of operation with respect to audio content, or a combination thereof. The earphone device 115 may be an earpiece, a hearing aid, an ear monitor, an ear terminal, a behind-the-ear device, any type of acoustic device, or a combination thereof. The earphone device 115 may include any type of component utilized for any type of earpiece. In certain embodiments, the earphone device 115 may include any number of ambient sound microphones that may be configured to capture and/or measure ambient sounds and/or audio content occurring in an environment that the earphone device 115 is present in and/or is proximate to. In certain embodiments, the ambient sound microphones may be placed at a location or locations on the earphone device 115 that are conducive to capturing and measuring ambient sounds occurring in the environment. For example, the ambient sound microphones may be positioned in proximity to a distal end (e.g. the end of the earphone device 115 that is not inserted into the first user's 101 ear) of the earphone device 115 such that the ambient sound microphones are in an optimal position to capture ambient or other sounds occurring in the environment. In certain embodiments, the earphone device 115 may include any number of ear canal microphones, which may be configured to capture and/or measure sounds occurring in an ear canal of the first user 101 or other user wearing the earphone device 115. In certain embodiments, the ear canal microphones may be positioned in proximity to a proximal end (e.g. the end of the earphone device 115 that is inserted into the first user's 101 ear) of the earphone device 115 such that sounds occurring in the ear canal of the first user 101 may be captured more readily.

The earphone device 115 may also include any number of transceivers, which may be configured transmit signals to and/or receive signals from any of the devices in the system 100. In certain embodiments, a transceiver of the earphone device 115 may facilitate wireless connections and/or transmissions between the earphone device 115 and any device in the system 100, such as, but not limited to, the first user device 102, the second user device 106, the third user device 110, the fourth user device 121, the fifth user device 125, the earphone device 130, the servers 140, 145, 150, 160, and the database 155. The earphone device 115 may also include any number of memories for storing content and/or instructions, processors that execute the instructions from the memories to perform the operations for the earphone device 115, and/or any type integrated circuit for facilitating the operation of the earphone device 115. In certain embodiments, the processors may comprise, hardware, software, or a combination of hardware and software. The earphone device 115 may also include one or more ear canal receivers, which may be speakers for outputting sound into the ear canal of the first user 101. The ear canal receivers may output sounds obtained via the ear canal microphones, ambient sound microphones, any of the devices in the system 100, from a storage device of the earphone device 115, or any combination thereof.

The ear canal receivers, ear canal microphones, transceivers, memories, processors, integrated circuits, and/or ear canal receivers may be affixed to an electronics package that includes a flexible electronics board. The earphone device 115 may include an electronics packaging housing that may house the ambient sound microphones, ear canal microphones, ear canal receivers (i.e. speakers), electronics supporting the functionality of the microphones and/or receivers, transceivers for receiving and/or transmitting signals, power sources (e.g. batteries and the like), any circuitry facilitating the operation of the earphone device 115, or any combination thereof. The electronics package including the flexible electronics board may be housed within the electronics packaging housing to form an electronics packaging unit. The earphone device 115 may further include an earphone housing, which may include receptacles, openings, and/or keyed recesses for connecting the earphone housing to the electronics packaging housing and/or the electronics package. For example, nozzles of the electronics packaging housing may be inserted into one or more keyed recesses of the earphone housing so as to connect and secure the earphone housing to the electronics packaging housing. When the earphone housing is connected to the electronics packaging housing, the combination of the earphone housing and the electronics packaging housing may form the earphone device 115. The earphone device 115 may further include a cap for securing the electronics packaging housing, the earphone housing, and the electronics package together to form the earphone device 115.

In certain embodiments, the earphone device 115 may be configured to have any number of changeable tips, which may be utilized to facilitate the insertion of the earphone device 115 into an ear aperture of an ear of the first user 101, secure the earphone device 115 within the ear canal of an ear of the first user 101, and/or to isolate sound within the ear canal of the first user 101. The tips may be foam tips, which may be affixed onto an end of the earphone housing of the earphone device 115, such as onto a stent and/or attachment mechanism of the earphone housing. In certain embodiments, the tips may be any type of eartip as disclosed and described in the present disclosure. The eartips as disclosed in the present disclosure may be configured to facilitate distributed reduced contact force, sound isolation for sound in the ear canal of the first user 101 (i.e. between the ambient environment and the ear canal environment within an ear of the first user 101), mold into a variety of forms and/or positions, encapsulate volumes upon insertion into an ear aperture of the first user 101, have a pressure adjusting design, facilitate notched stent retention (i.e. on a stent of the earphone housing), facilitate stent insertion into an ear canal of the first user 101 via an ear aperture of the first user 101, or any combination thereof. In certain embodiments, the eartip may be designed to provide sound isolation capability that is at least as effective as conventional foam and/or flange tips. Notably, the eartips may be manufactured and configured to be made in any desired size specifications and/or materials, and may be tailored to each individual user, such as first user 101. In contrast to conventional foam or flange tips, an eartip according to the present disclosure may be adjusted for size without having to substitute the eartip with another eartip, may have an EPA NRR rating of NRR=18, may have a unique flatter high frequency attenuation profile so as to maintain audio quality, may have ease of manufacturability, and may be designed to distribute contact force and minimize radial force against a user's ear canal walls when positioned in a user's ear canal. Additionally, an eartip according to the present disclosure may be made of a non-porous material that is not closed cell foam or open cell foam.

In certain embodiments, the eartip may be designed so that the earphone device's 115 retention force on the ear canal walls of the first user 101 may be distributed over a larger area than traditional foam or flange tips allow, thereby reducing the pressure on the ear canal walls of the first user 10. Unlike foam tips, which primarily provide a restoring radial force that exerts pressure against the ear canal walls of a user, the eartip is designed to move both radially and axially, which allows for more give and redistribution of contact over a larger area, and, thus, decreases the retention pressure. As a result, this allows for increased comfort for the user and allows the user to utilize the eartip for an extended period of time when compared to traditional foam and/or flange tips. In certain embodiments, the eartip utilized with the earphone device 115 may be configured to encapsulate a volume of gas and/or liquid. In either case (i.e. gas or liquid), the bulk of sound isolation provided by the eartip is achieved through the reflection of ambient sound waves so that the encapsulated volume can be low mass. In certain embodiments, portions of the eartip may encapsulate a volume with the ability to release volume when pressed upon without having to incorporate complicated valves. The encapsulated volume may be achieved by the ear canal wall pressing radially and/or axially against the outer surfaces of the eartip, which may force the outer portion of the eartip to seal with the inner portion of the eartip. In certain embodiments, the inner portion of the eartip may be small than the outer diameter of the stent of the earphone housing upon which the eartip is placed so that upon insertion of the eartip on the stent, the inner portion stretches outward to meet the outer surface of the eartip, which further facilitates the sealing of the ear canal of the first user 101.

In certain embodiments, the stent of the eartip, over which the eartip is placed, may be designed to have a smaller diameter front end and a larger diameter middle section to promote retention of the eartip on the stent itself. In certain embodiments, a portion of the eartip may have an inner core diameter that is smaller than the stent outer diameter so that the eartip provides radial compression upon the stent so as to enhance sealing and to add friction to prevent axial slippage within the ear canal of the first user 101. In certain embodiments, an increased mid-section inner core diameter of the eartip may be utilized (i.e. larger than the smaller inner core diameter of the eartip), which may be configured to line up with the mid-section outer diameter of the stent of the earphone housing of the earphone device 115. This may provide axial stability for the earphone device 115, while simultaneously preventing axial slippage from the ear canal of the first user 101. In certain embodiments, the eartip may have an insertion end that has a funnel shape, which aids in inserting the eartip onto the stent of the earphone housing of the earphone device 115.

In certain embodiments, the eartip has a configuration that applies minimal force against the first user's 101 ear canal. Additionally, the eartip can seal the first user's 101 ear canal by providing at least 15 dB of attenuation across frequency. To facilitate manufacturability, the eartip may be molded inverted, thereby allowing inexpensive mass production. Lips of the eartip may then be folded to contact ledges to for the eartip that may be utilized by the first user 101. Sealing and comfort depend upon an accurate fit within the first user's 101 ear canal, and, as a result, eartips according to the present disclosure may be manufactured in several single sizes, and, because of the unique design of the eartips, a single eartip may be adjusted to fit multiple sizes, which minimizes manufacturing costs, while allowing for more flexibility, versatility, and for a greater number of sizes for the eartip. Notably, any of the features of any of the eartips described in the present disclosure may be combined and/or interchanged with any other eartips described in the present disclosure. Furthermore, the shape, size, features and/or functionality of any of the components of the earphone device and/or hearbud housing device described in the present disclosure may be modified for each particular user for the shape and size of each user's ear aperture and/or ear canal, or a combination thereof.

Notably, in experiments conducted using the eartip, the experiments have shown that the eartip allows for similar levels of sound isolation when compared to conventional foam and/or flange tips. For example, experiments have shown that the eartips provided in the present disclosure provided a NRR of 18 with a generally flat high frequency profile. A flat attenuation profile maintains an ambient environment's frequency profile when level reduced by the attenuation, which can be useful in maintaining the quality of ambient speech and music (or other audio content) during the level reduction process.

In further embodiments, the eartip may be configured to have an open configuration prior to insertion onto a stent of the earphone housing and/or the earphone device 115 itself. By having an open configuration, the eartip may be mass produced using conventional molding techniques and/or by utilizing 3D commercial printers. The open configuration of the eartip also facilitates molding, and can be 3D printed, where the open configuration allows for resin removal. For example, resin removal may be achieved by utilizing commercial 3D printers that allow the use of lower durometer materials, such as Stratasys machines and the like. In certain embodiments, since the eartip has an open configuration, which is then sealed, any additional pressure can force encapsulated gas out of the eartip relieving the feedback pressure so as to keep the comfort level for the first user 101 relatively stable.

In addition to the first user 101, the system 100 may include a second user 120, who may utilize a fourth user device 121 to access data, content, and applications, or to perform a variety of other tasks and functions. Much like the first user 101, the second user 120 may be may be any type of user that may potentially desire to listen to audio content, such as from, but not limited to, a storage device of the fourth user device 121, a telephone call that the second user 120 is participating in, audio content occurring in an environment in proximity to the second user 120, any other type of audio content, or a combination thereof. For example, the second user 120 may be an individual that may be listening to songs stored in a playlist that resides on the fourth user device 121. Also, much like the first user 101, the second user 120 may utilize fourth user device 121 to access an application (e.g. a browser or a mobile application) executing on the fourth user device 121 that may be utilized to access web pages, data, and content associated with the system 100. The fourth user device 121 may include a memory 122 that includes instructions, and a processor 123 that executes the instructions from the memory 122 to perform the various operations that are performed by the fourth user device 121. In certain embodiments, the processor 123 may be hardware, software, or a combination thereof. The fourth user device 121 may also include an interface 124 (e.g. a screen, a monitor, a graphical user interface, etc.) that may enable the second user 120 to interact with various applications executing on the fourth user device 121, to interact with various applications executing in the system 100, and to interact with the system 100. In certain embodiments, the fourth user device 121 may include any number of transducers, such as, but not limited to, microphones, speakers, any type of audio-based transducer, any type of transducer, or a combination thereof. In certain embodiments, the fourth user device 121 may be a computer, a laptop, a tablet device, a phablet, a server, a mobile device, a smartphone, a smart watch, and/or any other type of computing device. Illustratively, the fourth user device 121 may be a computing device in FIG. 1. The fourth user device 121 may also include any of the componentry described for first user device 102, the second user device 106, and/or the third user device 110. In certain embodiments, the fourth user device 121 may also include a global positioning system (GPS), which may include a GPS receiver and any other necessary components for enabling GPS functionality, accelerometers, gyroscopes, sensors, and any other componentry suitable for a computing device.

In addition to using fourth user device 121, the second user 120 may also utilize and/or have access to a fifth user device 125. As with fourth user device 121, the second user 120 may utilize the fourth and fifth user devices 121, 125 to transmit signals to access various online services and content. The fifth user device 125 may include a memory 126 that includes instructions, and a processor 127 that executes the instructions from the memory 126 to perform the various operations that are performed by the fifth user device 125. In certain embodiments, the processor 127 may be hardware, software, or a combination thereof. The fifth user device 125 may also include an interface 128 that may enable the second user 120 to interact with various applications executing on the fifth user device 125 and to interact with the system 100. In certain embodiments, the fifth user device 125 may include any number of transducers, such as, but not limited to, microphones, speakers, any type of audio-based transducer, any type of transducer, or a combination thereof. In certain embodiments, the fifth user device 125 may be and/or may include a computer, any type of sensor, a laptop, a set-top-box, a tablet device, a phablet, a server, a mobile device, a smartphone, a smart watch, and/or any other type of computing device. Illustratively, the fifth user device 125 is shown as a tablet device in FIG. 1.

The fourth and fifth user devices 121, 125 may belong to and/or form a communications network 131. In certain embodiments, the communications network 131 may be a local, mesh, or other network that facilitates communications between the fourth and fifth user devices 121, 125, and/or any other devices, programs, and/or networks of system 100 or outside system 100. In certain embodiments, the communications network 131 may be formed between the fourth and fifth user devices 121, 125 through the use of any type of wireless or other protocol and/or technology. For example, the fourth and fifth user devices 121, 125 may communicate with one another in the communications network 116, such as by utilizing BLE, classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 131 may be configured to communicatively link with and/or communicate with any other network of the system 100 and/or outside the system 100.

Much like first user 101, the second user 120 may have his or her own earphone device 130. The earphone device 130 may be utilized by the second user 120 to hear and/or audition audio content, transmit audio content, receive audio content, experience any type of content, process audio content, adjust audio content, store audio content, perform any type of operation with respect to audio content, or a combination thereof. The earphone device 130 may be an earpiece, a hearing aid, an ear monitor, an ear terminal, a behind-the-ear device, any type of acoustic device, or a combination thereof. The earphone device 130 may include any type of component utilized for any type of earpiece, and may include any of the features, functionality and/or components described and/or usable with earphone device 115. For example, earphone device 130 may include any number of transceivers, ear canal microphones, ambient sound microphones, processors, memories, housings, eartips, foam tips, flanges, any other component, or any combination thereof.

In certain embodiments, the first, second, third, fourth, and/or fifth user devices 102, 106, 110, 121, 125 and/or earphone devices 115, 130 may have any number of software applications and/or application services stored and/or accessible thereon. For example, the first and second user devices 102, 111 may include applications for processing audio content, applications for playing, editing, transmitting, and/or receiving audio content, streaming media applications, speech-to-text translation applications, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 101, 120 to readily interact with the software applications. The software applications and services may also be utilized by the first and second users 101, 120 to interact with any device in the system 100, any network in the system 100 (e.g. communications networks 116, 131, 135), or any combination thereof. For example, the software applications executing on the first, second, third, fourth, and/or fifth user devices 102, 106, 110, 121, 125 and/or earphone devices 115, 130 may be applications for receiving data, applications for storing data, applications for auditioning, editing, storing and/or processing audio content, applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first, second, third, fourth, and/or fifth user devices 102, 106, 110, 121, 125 and/or earphone devices 115, 130 may include associated telephone numbers, internet protocol addresses, device identities, or any other identifiers to uniquely identify the first, second, third, fourth, and/or fifth user devices 102, 106, 110, 121, 125 and/or earphone devices 115, 130 and/or the first and second users 101, 120. In certain embodiments, location information corresponding to the first, second, third, fourth, and/or fifth user devices 102, 106, 110, 121, 125 and/or earphone devices 115, 130 may be obtained based on the internet protocol addresses, by receiving a signal from the first, second, third, fourth, and/or fifth user devices 102, 106, 110, 121, 125 and/or earphone devices 115, 130 or based on profile information corresponding to the first, second, third, fourth, and/or fifth user devices 102, 106, 110, 121, 125 and/or earphone devices 115, 130.

The system 100 may also include a communications network 135. The communications network 135 may be under the control of a service provider, the first and/or second users 101, 120, any other designated user, or a combination thereof. The communications network 135 of the system 100 may be configured to link each of the devices in the system 100 to one another. For example, the communications network 135 may be utilized by the first user device 102 to connect with other devices within or outside communications network 135. Additionally, the communications network 135 may be configured to transmit, generate, and receive any information and data traversing the system 100. In certain embodiments, the communications network 135 may include any number of servers, databases, or other componentry. The communications network 135 may also include and be connected to a mesh network, a local network, a cloud-computing network, an IMS network, a VoIP network, a security network, a VoLTE network, a wireless network, an Ethernet network, a satellite network, a broadband network, a cellular network, a private network, a cable network, the Internet, an internet protocol network, MPLS network, a content distribution network, any network, or any combination thereof. Illustratively, servers 140, 145, and 150 are shown as being included within communications network 135. In certain embodiments, the communications network 135 may be part of a single autonomous system that is located in a particular geographic region, or be part of multiple autonomous systems that span several geographic regions.

Notably, the functionality of the system 100 may be supported and executed by using any combination of the servers 140, 145, 150, and 160. The servers 140, 145, and 150 may reside in communications network 135, however, in certain embodiments, the servers 140, 145, 150 may reside outside communications network 135. The servers 140, 145, and 150 may provide and serve as a server service that performs the various operations and functions provided by the system 100. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. Furthermore, the server 150 may include a memory 151 that includes instructions, and a processor 152 that executes the instructions from the memory 151 to perform the various operations that are performed by the server 150. In certain embodiments, the servers 140, 145, 150, and 160 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 140, 145, 150 may be communicatively linked to the communications network 135, the communications network 116, the communications network 131, any network, any device in the system 100, any program in the system 100, or any combination thereof.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, the communications network 116, the communications network 131, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operation associated with the database 155. In certain embodiments, the database 155 may be connected to the earphone devices 115, 130, the servers 140, 145, 150, 160, the first user device 102, the second user device 106, the third user device 110, the fourth user device 121, the fifth user device 125, any devices in the system 100, any other device, any network, or any combination thereof.

The database 155 may also store information and metadata obtained from the system 100, store metadata and other information associated with the first and second users 101, 120, store user profiles associated with the first and second users 101, 120, store device profiles associated with any device in the system 100, store communications traversing the system 100, store user preferences, store information associated with any device or signal in the system 100, store information relating to patterns of usage relating to the first, second, third, fourth, and fifth user devices 102, 106, 110, 121, 125, store audio content associated with the first, second, third, fourth, and fifth user devices 102, 106, 110, 121, 125 and/or earphone devices 115, 130, store audio content and/or information associated with the audio content that is captured by the ambient sound microphones, store audio content and/or information associated with audio content that is captured by ear canal microphones, store any information obtained from any of the networks in the system 100, store audio content and/or information associated with audio content that is outputted by ear canal receivers of the system 100, store any information and/or signals transmitted and/or received by transceivers of the system 100, store any device and/or capability specifications relating to the earphone devices 115, 130, store historical data associated with the first and second users 101, 115, store information relating to the size (e.g. depth, height, width, curvatures, etc.) and/or shape of the first and/or second user's 101, 120 ear canals and/or ears, store information identifying and or describing any eartip utilized with the earphone devices 101, 115, store device characteristics for any of the devices in the system 100, store information relating to any devices associated with the first and second users 101, 120, store any information associated with the earphone devices 115, 130, store log on sequences and/or authentication information for accessing any of the devices of the system 100, store information associated with the communications networks 116, 131, store any information generated and/or processed by the system 100, store any of the information disclosed for any of the operations and functions disclosed for the system 100 herewith, store any information traversing the system 100, or any combination thereof. Furthermore, the database 155 may be configured to process queries sent to it by any device in the system 100.

The system 100 may also include a software application, which may be configured to perform and support the operative functions of the system 100, such as the operative functions of the first, second, third, fourth, and fifth user devices 102, 106, 110, 121, 125 and/or the earphone devices 115, 130. In certain embodiments, the application may be a website, a mobile application, a software application, or a combination thereof, which may be made accessible to users utilizing one or more computing devices, such as the first, second, third, fourth, and fifth user devices 102, 106, 110, 121, 125 and/or the earphone devices 115, 130. The application of the system 100 may be accessible via an internet connection established with a browser program or other application executing on the first, second, third, fourth, and fifth user devices 102, 106, 110, 121, 125 and/or the earphone devices 115, 130, a mobile application executing on the first, second, third, fourth, and fifth user devices 102, 106, 110, 121, 125 and/or the earphone devices 115, 130, or through other suitable means. Additionally, the application may allow users and computing devices to create accounts with the application and sign-in to the created accounts with authenticating username and password log-in combinations. The application may include a custom graphical user interface that the first user 101 or second user 120 may interact with by utilizing a browser executing on the first, second, third, fourth, and fifth user devices 102, 106, 110, 121, 125 and/or the earphone devices 115, 130. In certain embodiments, the software application may execute directly as an installed program on the first, second, third, fourth, and fifth user devices 102, 106, 110, 121, 125 and/or the earphone devices 115, 130.

Exemplary Embodiments of Eartips and Earplugs

Figure 2A:
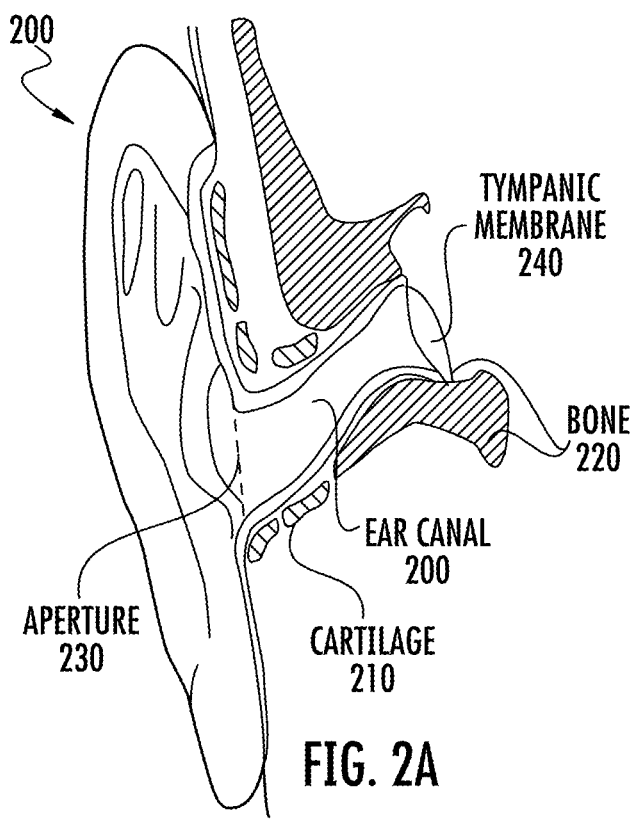
FIG. 2A illustrates a generic cross section of an ear canal.

FIG. 2A illustrates a cross section of an ear canal 200, including a cartilaginous region 210 and a bony region 220 of an ear canal 200. The entrance of the ear canal 200 is referred to as the aperture 230 and defines a first end of the ear canal 200 while the tympanic membrane 240 defines the other, internal end of the ear canal 200.

Figure 2B:
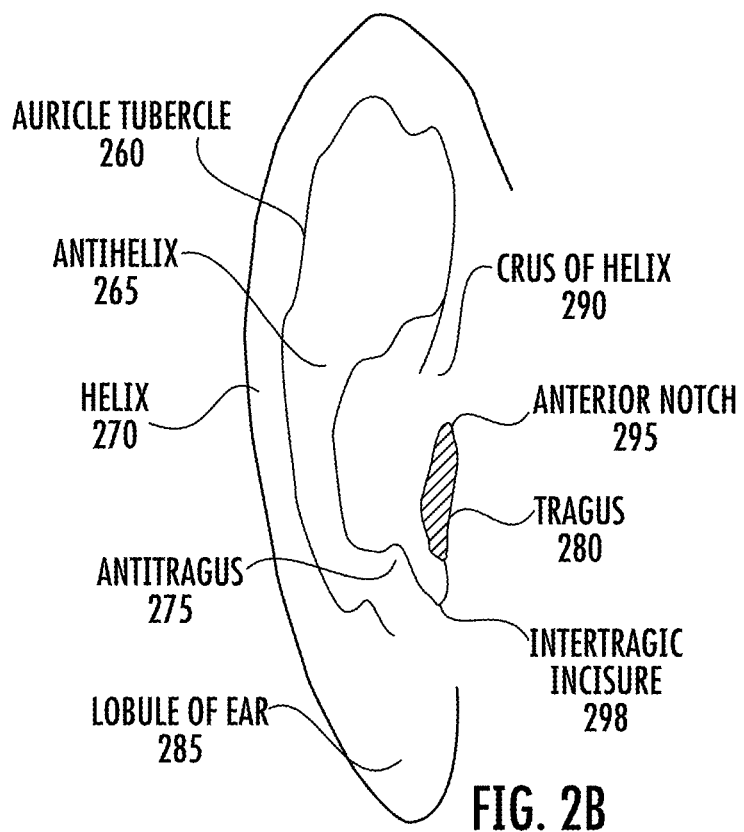
FIG. 2B illustrates the general outer physiology of an ear.

FIG. 2B illustrates the outer physiology of ear 200, which includes an auricle tubercle 260, the antihelix 265, the helix 270, the antitragus 275, tragus 280, lobule 285 of ear 200, crus of helix 290, anterior notch 295, and intertragic incisures 298.

Multiple exemplary embodiments of eartip 300 are disclosed in FIGS. 3-60, and in other figures, with like parts or components having like numbers. Such embodiments can be used with an ear 200, and can be sized and sizable to fit unique ear geometry of different users, including a person with ears that have different geometries.

Figure 3A:
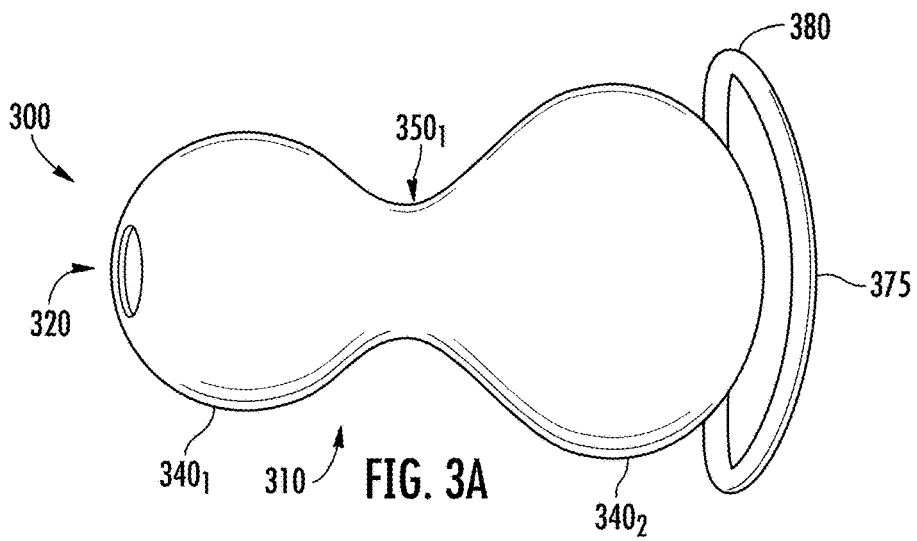
FIG. 3A illustrates one embodiment of an eartip.
Figure 3B:
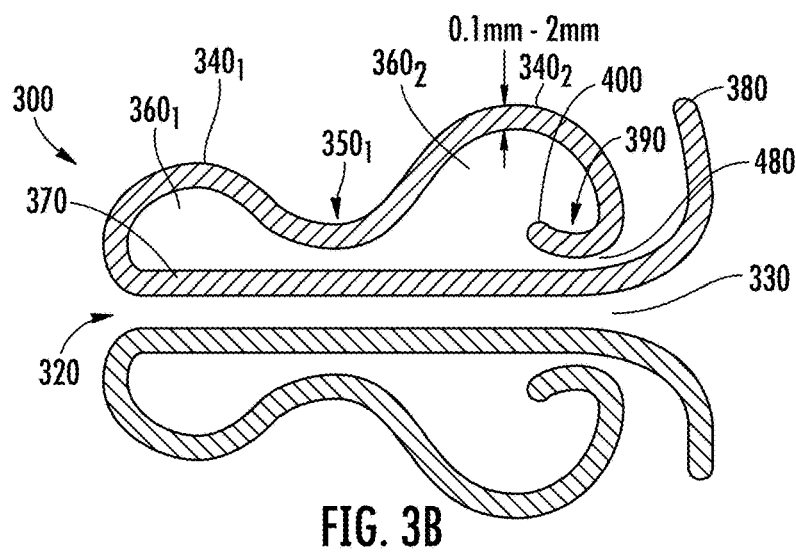
FIG. 3B illustrates a cross-sectional view of the embodiment of FIG. 3A.

FIG. 3A illustrates a perspective view of one embodiment of an eartip 300, and FIG. 3B illustrates a cross-sectional view of the eartip 300 of FIG. 3A. The eartip 300 includes an elongated flexible body 310, which can be formed of membrane, with apertures 320 that continue to channel 330 that forms a core of eartip 300 and that runs longitudinally along the length of elongated body 310. The apertures 320 and channel 330 can receive an earplug or a stent or other coupling member of an earphone device disclosed herein. The elongated body 310 can have multiple bulbous regions $340_{1-n}$, such as first bulbous region $340_1$ and second bulbous region $340_2$. Such an arrangement can be referred to as a double hump or double ridge structure. As shown in FIG. 3B, the membrane of the elongated flexible body 310 forms an outer portion, here illustrated as bulbous regions $340_{1-n}$, and an inner portion, here illustrated as channel wall 370, between which there is an encapsulated volume.

The first bulbous region $340_1$ and second bulbous region $340_2$ can be separated by one or more transition regions $350_{1-n}$, which can be concave or narrowing from side perspective, and (in FIG. 3A) can narrower than the $340_1$ and second bulbous region $340_2$. The bulbous regions $340_1$ and $340_2$ can form one or more cavities $360_{1-n}$, which can be continuous with each other and which also can be sealed independently of each other when transition region $350_1$ seals against channel wall 370 when one or more of bulbous regions $340_{1-n}$ are compressed, including being compressed by insertion in an ear canal where one or more of the bulbous regions $340_{1-n}$ have a un-compressed diameter that is greater than the inner diameter of the ear canal. When sealed with an enclosed volume the bulbous regions $340_{1-n}$ exert a force against the ear canal; however, at least a portion of the enclosed volume can be released as discussed herein when the pressure of the enclosed volume, of the force exerted on the bulbous regions $340_{1-n}$ overcome a threshold value and some gas or fluid of the enclosed volume is released.

The first bulbous region $340_1$ and second bulbous region $340_2$ can be different sizes or the same size. For example, the first bulbous region $340_1$ can have a first bulbous radius at the greatest radial extension of the first bulbous region $340_1$ that is less than a second bulbous radius of the second bulbous region $340_2$ at the greatest radial extension of the second bulbous region $340_2$. Such an arrangement provides an outer diameter of the first bulbous region $340_1$ that is less than the outer diameter of the second bulbous region $340_2$.

The eartip 300 can also have lip or retaining ridge 375, which can contact an ear plug, stent of an earphone phone device or the housing of the earphone device when the eartip 300 is coupled to the earphone device or ear plug. The lip 375 can be curved towards the bulbous regions while also extending in the direction of the earphone device or ear plug to ensure a flush fit between the two components. Further, when one or more of the bulbous regions are compressed, such as by insertion of the eartip 300 in a user's ear canal, the outermost tip 380 of lip 375 can flex axially toward the earphone device and radially toward the wall of the ear canal. With the outermost tip 380 of lip 375 pressing against the ear canal wall, the outermost tip 380 of lip 375 seals the ear cavity internal to the lip 375 until a threshold force at least partially releases some of the enclosed volume of the cavity. The lip 375 can be straight or curved with additional protrusions depending upon the eartip 300.

The eartip 300 can also have internal sealing section 390 that terminates in a sealing tip 400. In an un-flexed or un-compressed state, the internal sealing section 390 can be curved, such that the sealing tip 400 extends away from lip 375. Also, the sealing tip 400 can extend radially. In use as described herein, compression or flexing of one or more the bulbous regions $340_{1-n}$ the radial direction can flex the sealing section 390 in the axial direction, allowing a volume of gas (e.g., air) to escape one or more of cavities $360_{1-n}$. Such an escape of air can provide a custom fit as described herein by an amount of air escaping directly correlated to the amount of force provided by the ear canal that compresses the eartip 300.

In some embodiments, the durometer of an eartip can vary between 2 Shore A to 90 Shore A. Exemplary dimensions of the thickness of the eartip in region of the lip or back ridge 375 and in sealing section 390 can be between approximately 0.001 mm to approximately 2 or more mm. The length (along the long axis) of an eartip can be from approximately 4 mm to approximately 25 mm or more depending upon the final usage. The outer diameter of the eartip can vary from approximately 3 mm to approximately 50 or more mm, typically approximately 8 mm to approximately 18 mm.

Figure 4A:
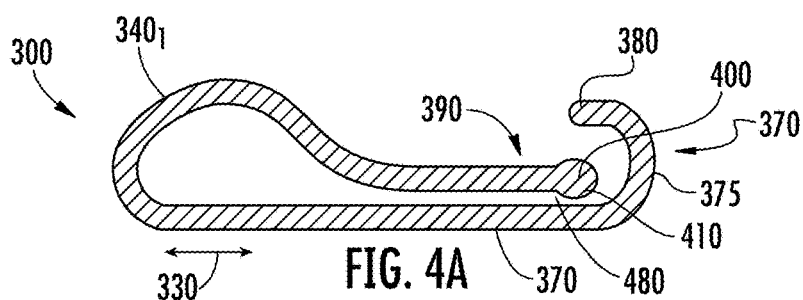
FIG. 4A illustrates a cross-sectional view of another embodiment of an eartip.

FIG. 4A illustrates an upper symmetric half of a cross section of another embodiment of an eartip 300 with a single bulbous region $340_1$ and a single cavity $360_1$. Although not noted throughout, many of the embodiments disclosed herein illustrate only an upper or lower symmetric half of a cross section of an eartip 300. Being symmetrical, the other half has the same features and structural arrangement. And, such cross sections are a cross section of an annular structures, many of which form a toroid or a semi toroid shape; however, such toroids or semi-toroids disclosed herein cannot be solid or solid.

In this embodiment, sealing section 390 can have a sealing tip 400 with a terminal protrusion 410 that aids in sealing against channel wall 370, and indirectly against a stent inserted into channel 330, and outermost tip or back retaining ridge 380. In this embodiment, the sealing section 390 can be approximately straight or parallel in an un-flexed state.

Figure 4B:
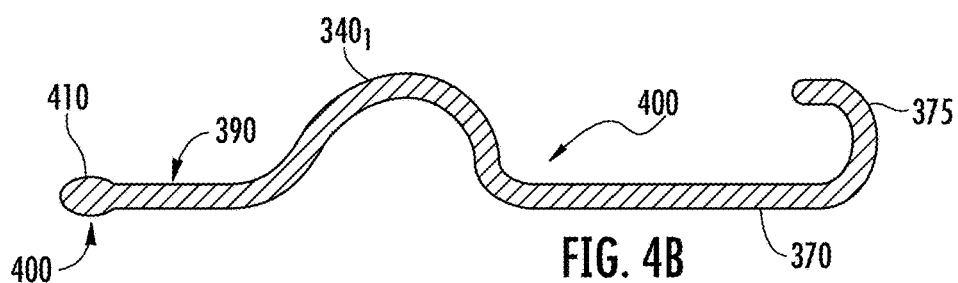
FIG. 4B illustrates a negative molded cross sectional portion corresponding to the cross section of FIG. 4A.

FIG. 4B illustrates a negative molded cross sectional portion corresponding to the cross section of FIG. 4A. An inverted shape mold, which is shown in an un-flexed state in FIG. 4B, is more moldable or flexible than the insertable eartip form that is insertable in the ear canal of a user. The inverted shape mold 300 illustrated in FIG. 4B folds to the eartip form 300 shown in FIG. 4A, which is in a flexed state even without interaction or manipulation unlike a foam tip that is not flexed when not interacting or being manipulated.

Figure 5A:
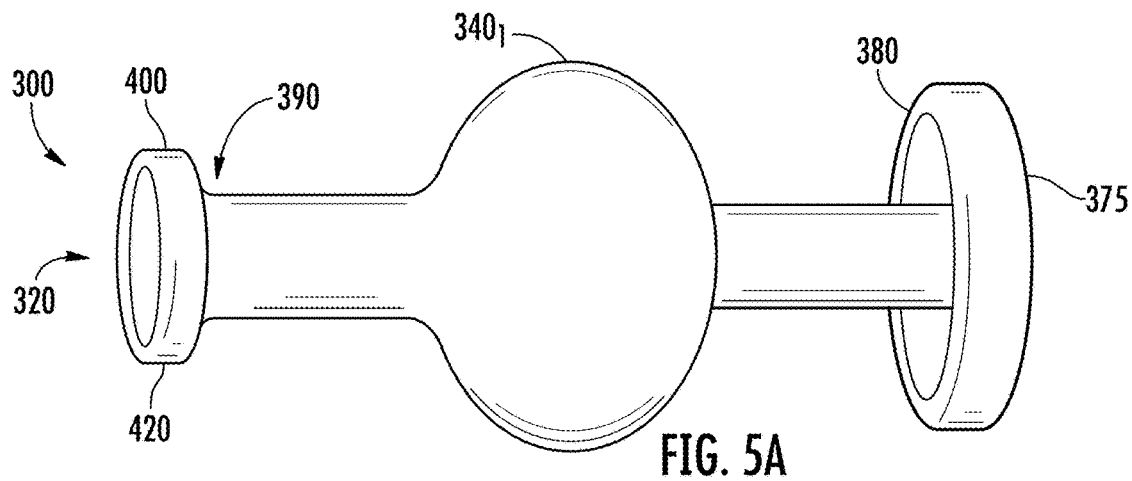
FIG. 5A illustrates one embodiment of an eartip in a negative molded form before being folded over on itself.
Figure 5B:
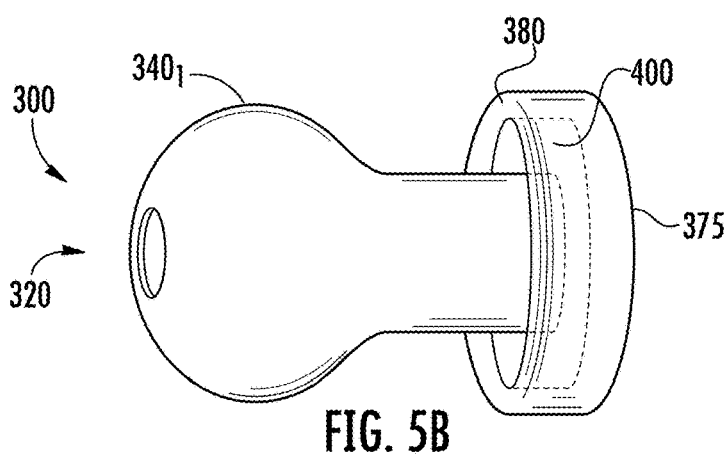
FIG. 5B illustrates the eartip of FIG. 5A folded over on itself.

FIG. 5A illustrates a three dimensional perspective view of another embodiment of an inverted molded eartip 300, which can be folded to obtain the insertable eartip form shown in FIG. 5B. However, an inverted shape mold is not needed as a positive final form or insertable form mold can also be used. In the embodiment shown in FIGS. 5A and 5B, the sealing tip 400 can form an annular ridge 420 that seats in lip 375. Also in the embodiment shown in FIGS. 5A and 5B, the bulbous region $340_1$ can have an outer diameter that is slightly less than the outer diameter of the lip 375.

Figure 6A:
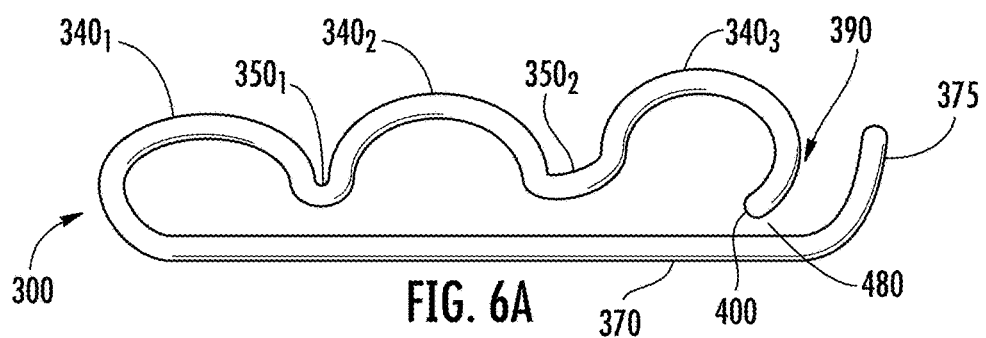
FIG. 6A illustrates a cross-sectional view of another embodiment of an eartip.
Figure 6B:
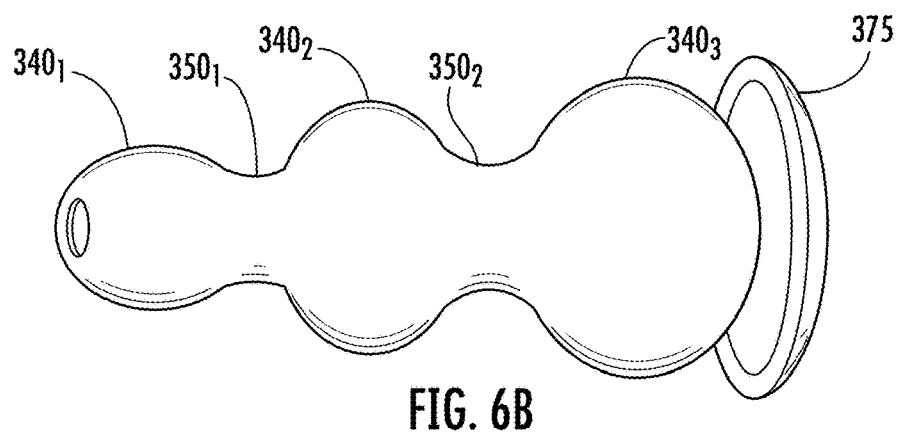
FIG. 6B illustrates a perspective view of the eartip of FIG. 6A.

FIG. 6A illustrates half of a cross section of another embodiment of an eartip designed for multiple size ear canals, and FIG. 6B illustrates a three dimensional view of the eartip 300 of FIG. 6A. The eartip 300 has three bulbous regions $340_{1-3}$ and the sealing section 390 can press against the channel wall 370, inserted stent of an earphone, or lip or back ridge 375 when one or more of the three bulbous regions $340_{1-3}$ are compressed. In this embodiment, the transition regions $350_1$ and $350_2$ can be different lengths. For example, the second transition region $350_2$ can be longer than the first transition region $350_1$. Also, the second transition region $350_2$ can feature a flat surface while first transition region $350_1$ can feature greater concavity than the second transition region $350_2$.

Figure 7A:
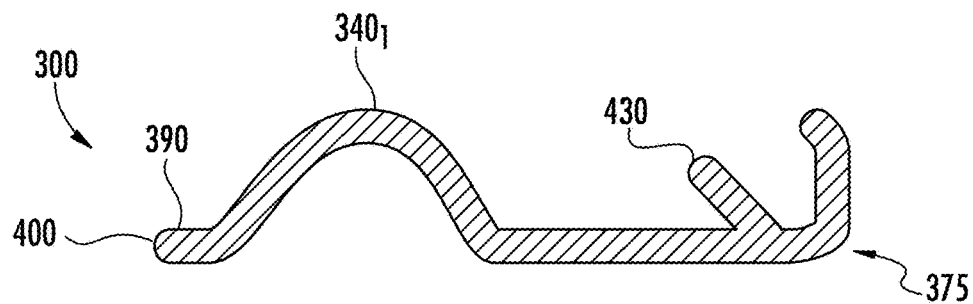
FIG. 7A illustrates one embodiment of a cross-sectional view of an eartip in a negative molded form before being folded over on itself.
Figure 7B:
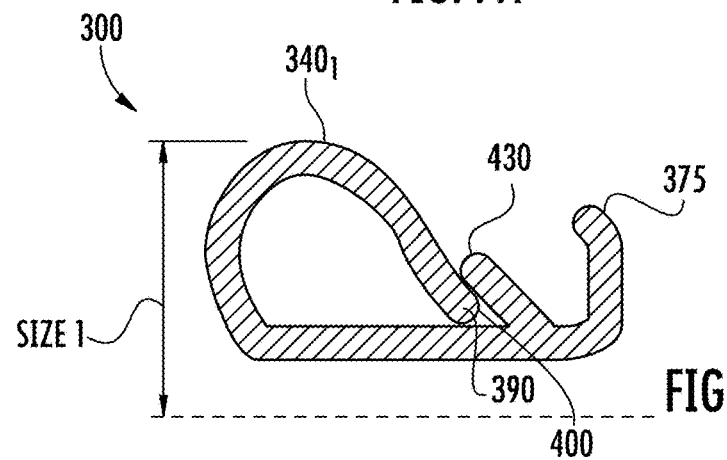
FIG. 7B illustrates the embodiment of the eartip of FIG. 7A folded over on itself for use as an exemplary first size.
Figure 7C:
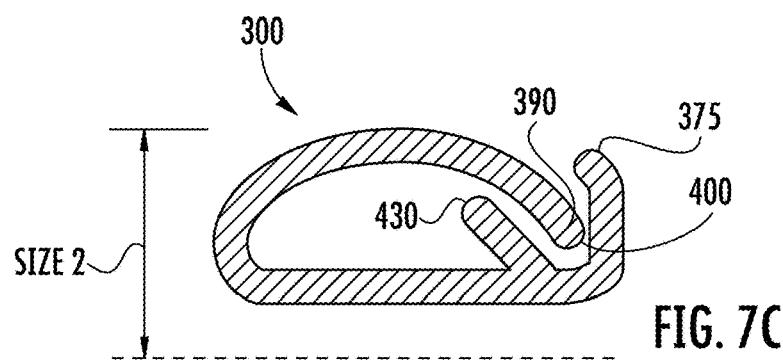
FIG. 7C illustrates the embodiment of the eartip of FIG. 7A folded over on itself for use as an exemplary second size.
Figure 7D:
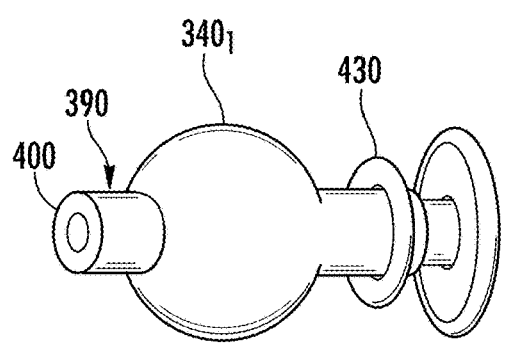
FIG. 7D illustrates the embodiment of the eartip of FIG. 7A in a negative molded form before being folded over on itself.

FIGS. 7A-D illustrate another embodiment of a multi-size eartip 300 in different configurations with internal sealing ridge 430, which can be a continuous or partial annular ridge. FIG. 7A illustrates an inverted half cross section of multi-size eartip 300, and FIGS. 7B and 7C are half cross sections of two different sizes when folded operationally. In the design shown in FIGS. 7A-D, the sealing tip 400, which is shown as cylindrical, is designed to contact internal sealing ridge 430 to provide a eartip size 1. When sealing tip 400 contacts lip or back ridge 375, the eartip 300 will have a size 2. Thus, when a user needs a smaller sized eartip 300, the user will can move sealing tip 400 to internal sealing ridge 430. However, when the user wants a larger size they will move sealing tip 400 to lip or back ridge 375.

Figure 8:
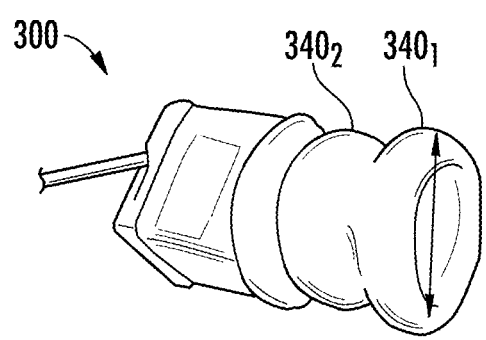
FIG. 8 illustrates another embodiment of an eartip.
Figure 9:
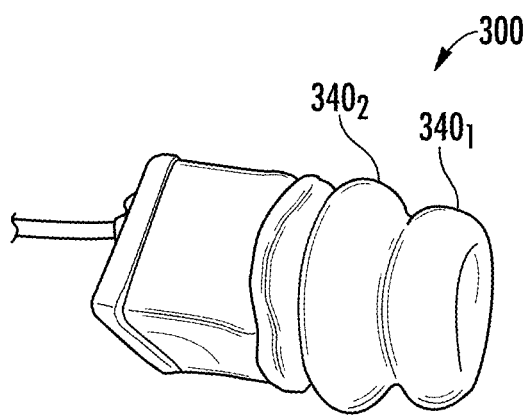
FIG. 9 illustrates another embodiment of an eartip.

FIGS. 8-10 illustrate alternative embodiments of multi-size eartips 300. FIG. 8 illustrates an eartip 300 with multiple bulbous regions $340_1$ and $340_2$, with first or front bulbous region $340_1$ having a larger outer diameter than second or rear bulbous region $340_2$ with respective exemplary measurements of approximately 12.5 mm and approximately 11.3 mm. Such an arrangement can provide stability if the first or front bulbous region $340_1$ can be compressed into an opening ear canal void. The embodiment shown in FIG. 8 can be useful if the larger diameter first or front bulbous region $340_1$ can be compressed past a bend then re-expanded providing stability. The thickness of the ridges can be from approximately 0.001 mm to approximately 1-2 mm or more. The length of an eartip can vary from approximately 5 mm to approximately 20 or more mm.

FIG. 9 illustrates an embodiment with multiple bulbous regions $340_1$ and $340_2$, with first or front bulbous region $340_1$ having a smaller outer diameter than second or rear bulbous region $340_2$. If the user's ear canal inner diameter is larger than first or front bulbous region $340_1$ then the eartip can be inserted further inward until the inner diameter or a turn in the ear canal contacts the outer diameter of either bulbous region $340_1$ and $340_2$.

Figure 10A:
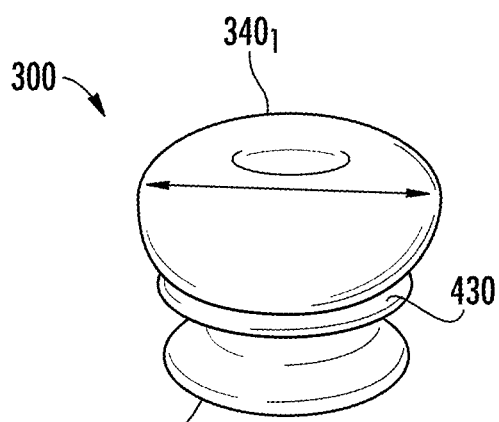
FIG. 10A illustrates another embodiment of an eartip.
Figure 10B:
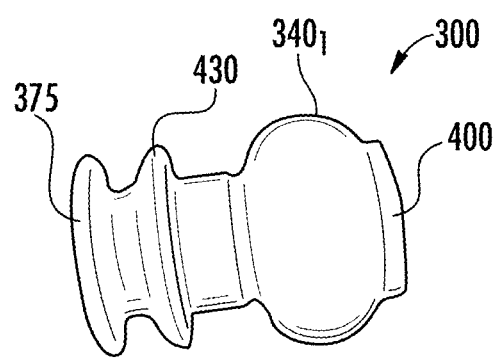
FIG. 10B illustrates a first configuration of the embodiment of the eartip of FIG. 10A.
Figure 10C:
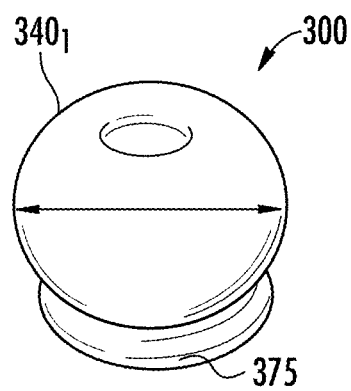
FIG. 10C illustrates a second configuration of the embodiment of the eartip of FIG. 10A.

FIGS. 10A-C illustrate another embodiment of a multi-size eartip 300 with single bulbous region $340_1$ and with FIG. 10B being the inverted mold inside of the eartip 300 of FIGS. 10A and 10C. For example, the sealing tip 400 can sit upon or seat in internal sealing ridge 430 resulting in an outer diameter of bulbous region $340_1$ that is larger than the outer diameter of bulbous region $340_1$ when the sealing tip 400 seats on lip or back ridge 375. A user can adjust the sealing tip 400 to adjust the size between a number of sizes equal to the number of ridges (e.g. 375, 430). Thus, an eartip can have one or more sizes. Exemplary dimensions of such an embodiment or others disclosed herein can be between approximately 0.001 mm to approximately 2 or more mm for the thickness of the membrane forming the bulbous regions $340_1$ and/or the ridges (e.g. 375, 430). Such an eartip can have a length of approximately 4 mm to approximately 25 mm or more depending upon the final usage. The outer diameter of the contact portion of the eartip can vary from approximately 6 mm to approximately 30 or more mm, typically approximately 8 mm to approximately 18 mm. The inner diameter of aperture 320 can vary depending upon the out diameter of the stent to which it is designed, for example from approximately 3 mm to approximately 7 mm.

FIGS. 11-18 illustrate various embodiments of eartips 300 that can be customized to particular functional needs and that show a cross section outline 450 of the eartip 300 in some illustrations. FIG. 11 illustrates a front view eartip 300 and FIG. 12 is the back view thereof with a conical surface that decreases as the aperture 320 transitions to the channel 330. The front view is the side that enters the ear canal first, while the back view is the side that receives stent of an earphone or otherwise couples to an earphone.

FIG. 13 illustrates an embodiment of eartip 300 with a channel protrusion 440, which can form a cylindrical extension that extends beyond the end of bulbous region $340_1$ in this embodiment. Also, the channel protrusion 440 can be formed when an inverted eartip is folded over on itself such that the component is an a flexed state. The cross sectional view 450 shows the underneath of bulbous region $340_1$ having an overhanging portion or that forms a cap that resembles a mushroom shape or a partial toroid.

FIG. 14 illustrates an embodiment of eartip 300 with three bulbous regions $340_{1-3}$, with the middle bulbous region $340_2$ having a larger diameter than the interior bulbous region $340_2$ and exterior bulbous region $340_1$. Additionally, channel protrusion 440, which is shown as a cylindrical extension, is recessed from the bulbous region $340_3$ such that the exterior bulbous region $340_3$ extends outward beyond the channel protrusion 440.

FIG. 15 illustrates an embodiment of eartip 300 with two bulbous regions $340_{1-2}$ where the channel 330 transitions directly into bulbous region $340_1$. In this embodiment, the eartip 300 can have transition region 350 that forms a annular transition between two bulbous regions $340_{1-2}$.

FIG. 16 illustrates an embodiment of eartip 300 with two bulbous regions $340_{1-2}$ without an elongated or flat transition region 350.

FIGS. 17 and 18 illustrate embodiments of eartip 300 with a single bulbous region $340_1$. The embodiment of FIG. 18 features a channel protrusion 440 that extends beyond the bulbous region $340_1$. FIGS. 16-18 show a portion of the membrane of elongated body 310 in cross section.

Figure 19:
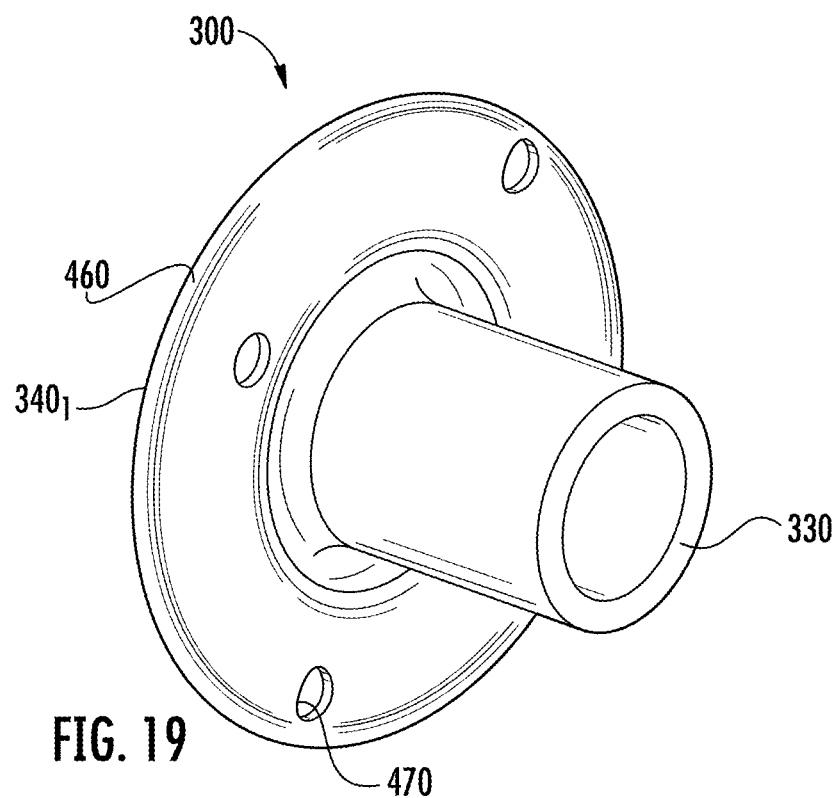
FIG. 19 illustrates an embodiment of an eartip formed by three dimensional printing.
Figure 20A:
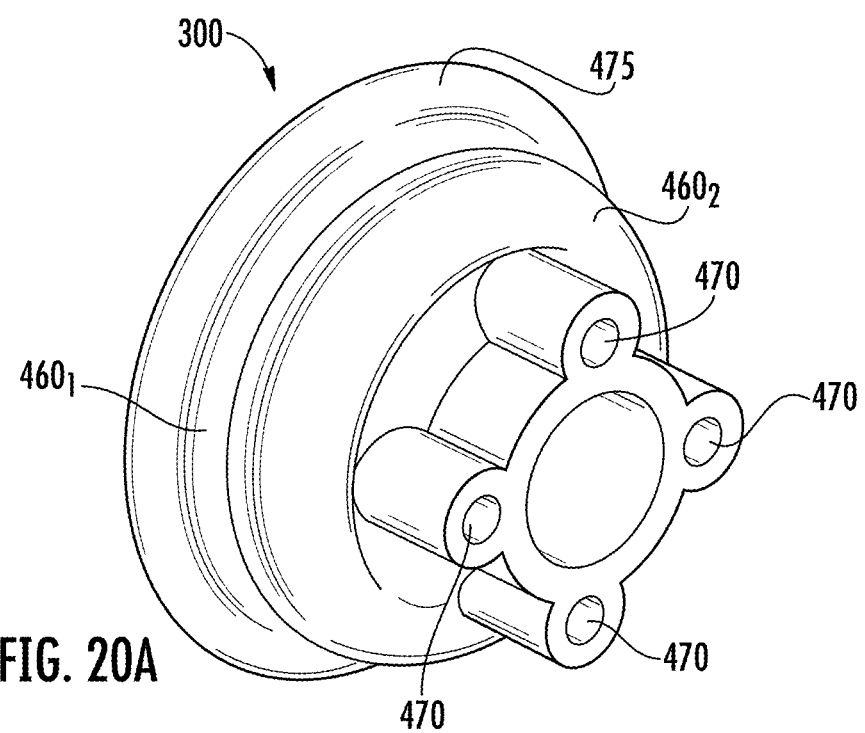
FIG. 20A illustrates another embodiment of an eartip formed by three dimensional printing.

FIGS. 19 and 20A and 20B and 20C illustrate two different embodiments of eartip 300 formed with three dimensional printing. However, any of the eartips disclosed herein can be formed with three dimensional printing. Such embodiments can include resin flow channels that can be sealed after printing if needed. FIG. 19 illustrates an eartip 300 that contains a single bulbous region $340_1$, which can contain a resin and be a sealed bladder 460. The single sealed bladder 460 can be sealed except for the resin flow holes 470, which can also be sealed if desired. A shaft or channel 330 can be designed to fit on a stent. FIG. 20A illustrates an eartip that includes a flange 475 that can be manipulated to press on a first bladder $460_1$ which then presses against a second bladder $460_2$. The channel 330 can fit on a stent, and when 3D printed a resin flow holes or exit portion 470 can be included.

Figure 20B:
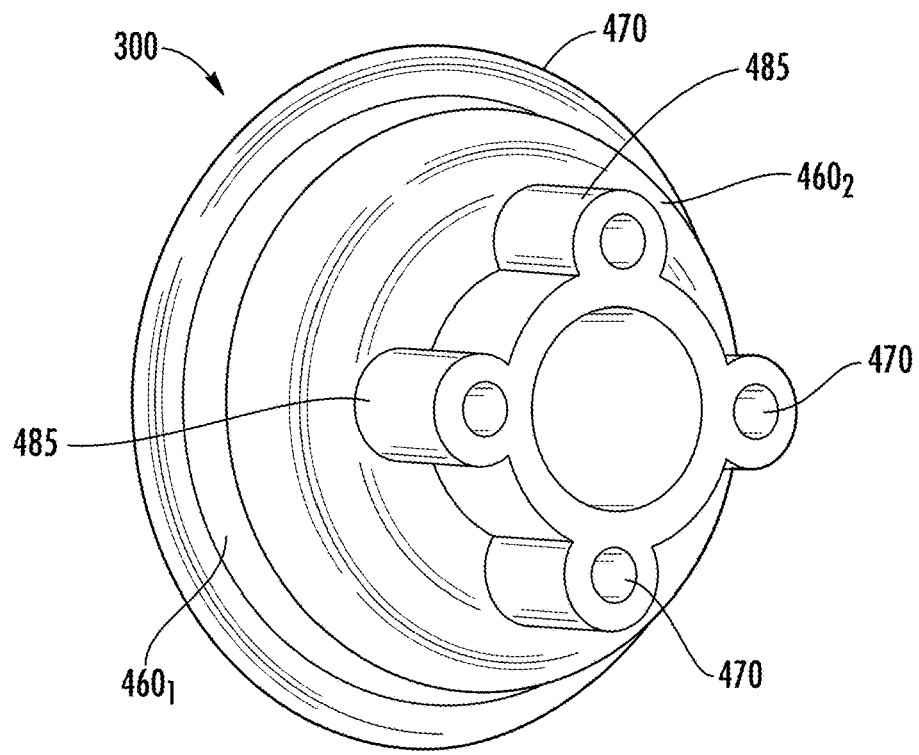
FIG. 20B illustrates another embodiment of an eartip formed by three dimensional printing.
Figure 20C:
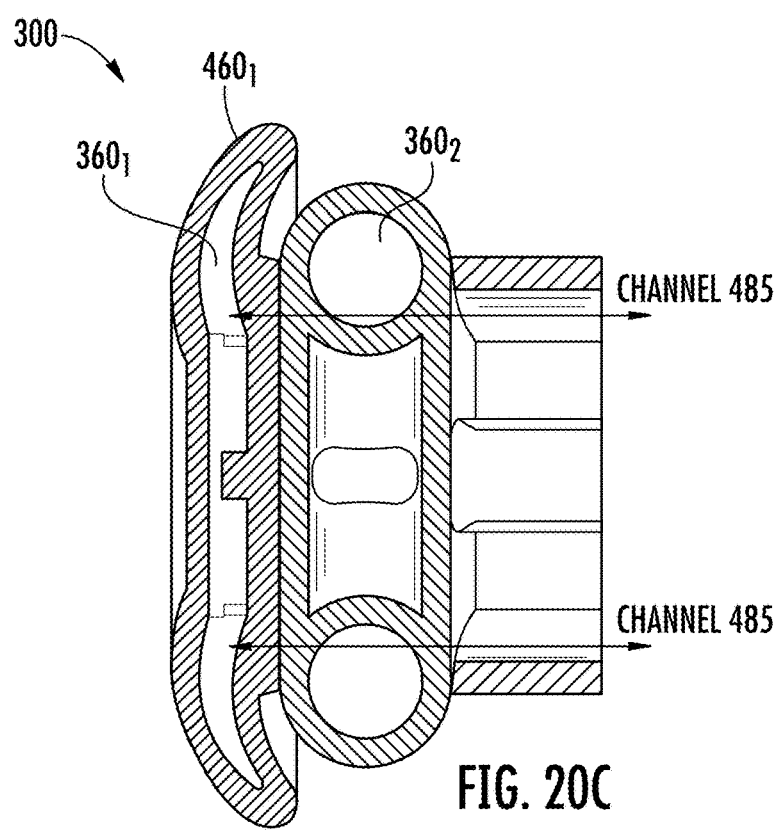
FIG. 20C illustrates a cross-sectional view of the embodiment of the eartip of FIG. 20B.

FIG. 20B illustrates multiple resin channels 485 that terminate in resin flow holes 470. FIG. 20C is a cross sectional view of an eartip 300 showing cavity $360_1$ and cavity $360_2$ and channels 485. The channels 485 allow drainage through the resin flow holes 470. Post processing can seal the channels 485 by sealing the resin flow holes 470, which can seal cavity $360_1$ and cavity $360_2$.

Figure 21:
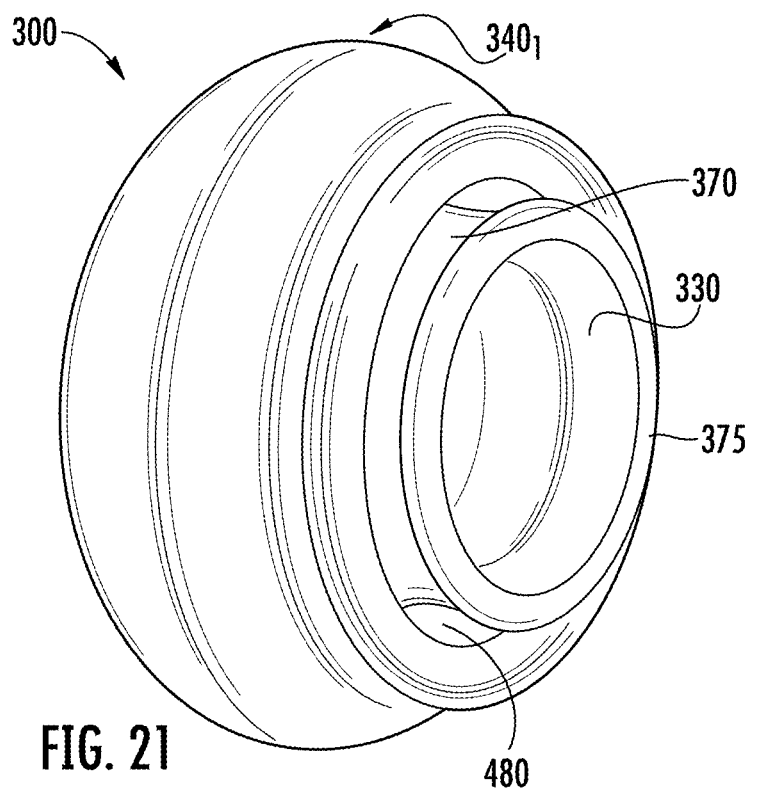
FIG. 21 illustrates a rear view of another embodiment of an eartip.
Figure 22:
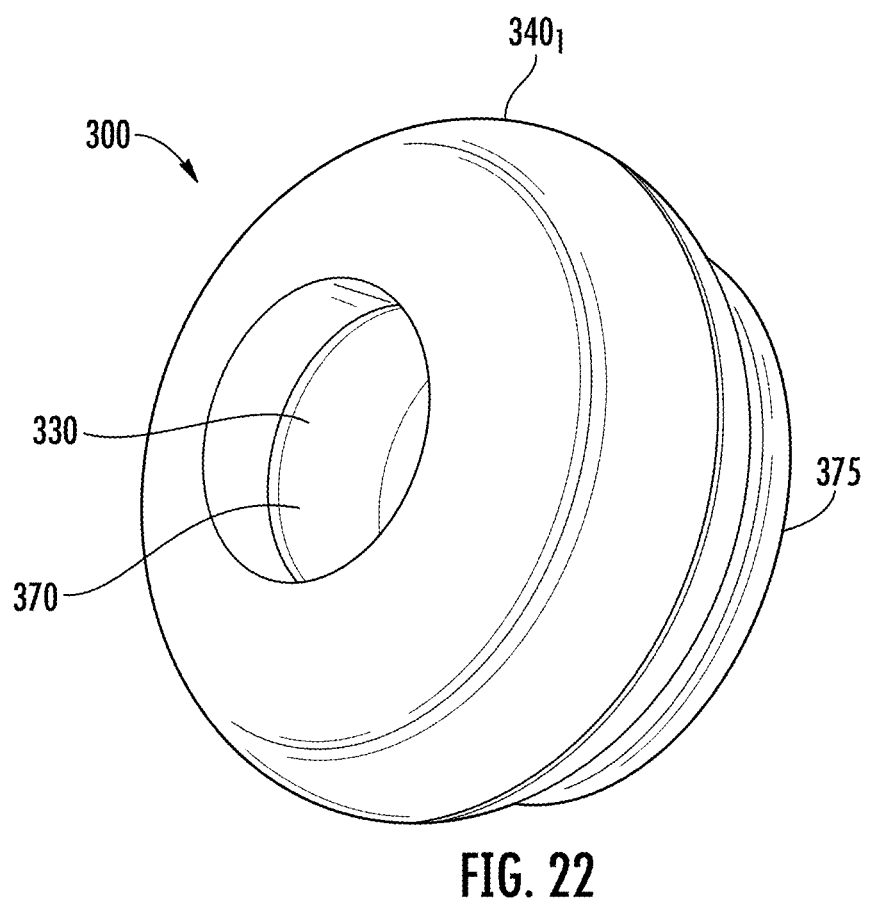
FIG. 22 illustrates a front view of another embodiment of an eartip.

FIGS. 21 and 22 illustrate two different embodiments of eartip 300. The outward portion of bulbous region $340_1$ contacts the ear canal wall when inserted into the ear canal. The inner portion contains a channel 330 that can fit on a stent. In this embodiment, channel 330 flares outward radially and axially to provide a stent insertion interface that is wider than channel 330 at the midpoint of channel such that the channel's diameter can increase at it extends longitudinally.

As explained with the other embodiments, prior to insertion into an ear canal the bulbous region $340_1$ and channel wall 370 encapsulate a medium (e.g., gas, fluid) that can have a release opening 480 aiding molding. Upon insertion onto a stent, the channel wall 370 can move flexibly outward decreasing the release opening 480, and/or upon inserting into an ear canal, the ear canal wall can press inward toward the stent moving the bulbous region $340_1$ inward, decreasing the release opening 480. As illustrated in other embodiments, the release opening 480 can be faced inward toward the ear canal or formed to face toward the ambient environment.

Figure 23A:
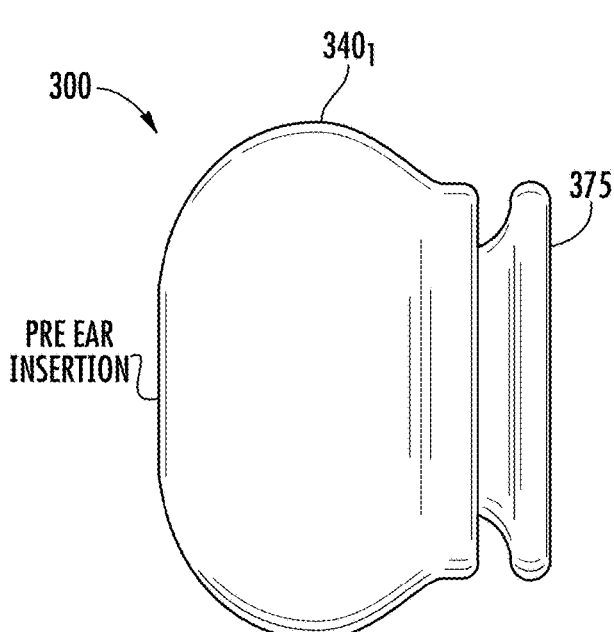
FIGS. 23A and 23B illustrate the operation of another embodiment of an eartip.
Figure 23B:
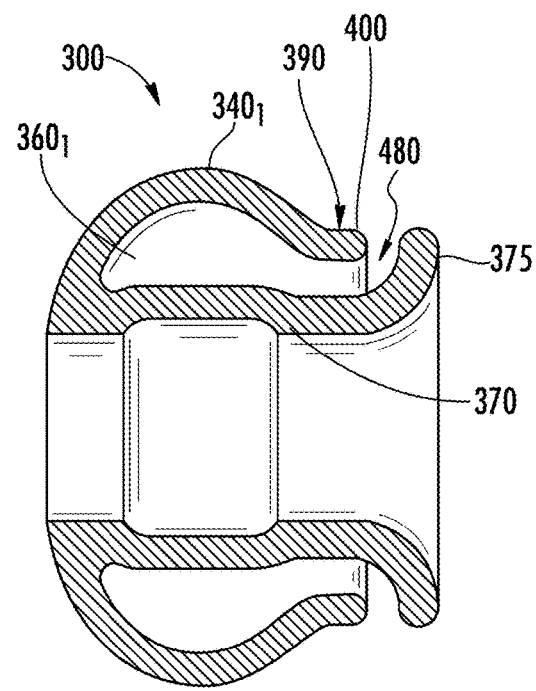
Figure 24A:
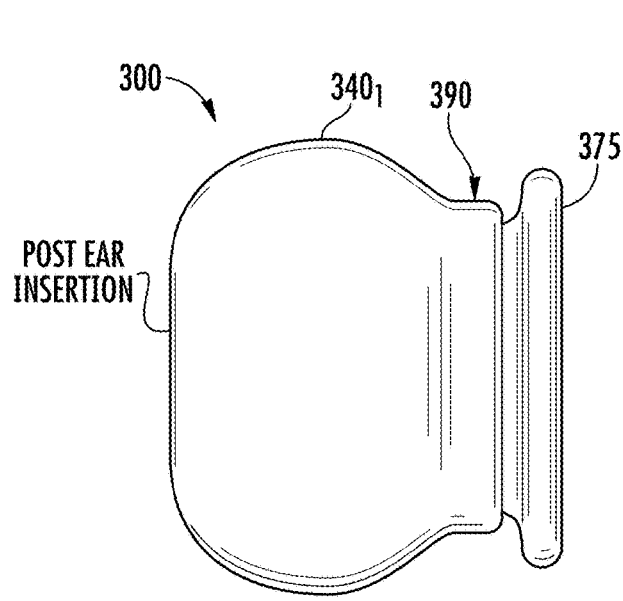
FIGS. 24A and 24B illustrate further operations of another embodiment of an eartip.
Figure 24B:
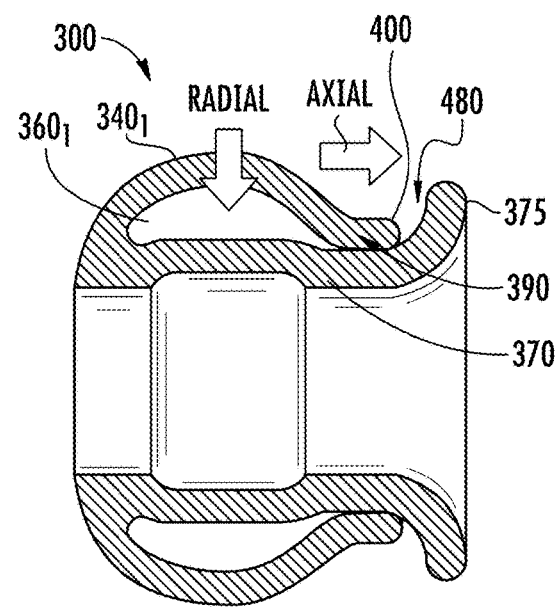

FIGS. 23A and B and FIGS. 24A and B illustrate the operation of an embodiment of the eartip 300. FIGS. 23A and B illustrate an open arrangement of an eartip 300 prior to insertion into an ear canal. The shape of the eartip 300 pre-ear canal insertion shown in FIG. 23A contains a bulbous region $340_1$, a sealing section 390, sealing tip 400, a lip or back ridge 375 and a gap or release opening 480 between sealing section 390 and sealing tip 400 and lip or back ridge 375, where the bulbous region $340_1$ and the lip or back ridge 375 encapsulate a volume or cavity $360_1$. In this arrangement, gas or air can flow in and out of volume or cavity $360_1$.

FIGS. 24A and B illustrate a closed arrangement of eartip 300 upon insertion into an ear canal and/or insertion onto a stent. After or post-insertion, either on a stent or into an ear canal, the bulbous region $340_1$, sealing section 390, sealing tip 400, lip or back ridge 375 can have been moved to decrease or close gap or release opening 480. For example upon insertion into an ear canal, the ear canal wall pressure on the bulbous region $340_1$ can move radially and axially as shown to relieve the pressure pressing against the ear canal wall. Similarly, the sealing section 390, and thus sealing tip 400, can also move radially and axially as shown to relieve the pressure pressing against the ear canal wall. This movement in two directions which are orthogonal to each other is in contrast to foam tips that will always press back radially dependent upon the amount of deformation of the foam. The combination of radial and axial movement of the bulbous region $340_1$ and/or sealing section 390, and thus sealing tip 400, helps decrease pressure on the ear canal wall and increase contact area of the bulbous region $340_1$ that also decreases pressure for a given retaining force. Additionally, by moving sealing section 390 with sealing tip 400 to come into contact with channel wall 370, sealing section 390 with sealing tip 400 can seal cavity $360_1$ to maintain a constant volume in cavity $360_1$.

Unlike traditional foam tips, the pressure releasing system disclosed herein reduces pressure against an ear canal or other structure. If an eartip 300 is inserted into an ear canal that compresses a bulbous region 340, release of gas from an enclosed volume of cavity 360 reduces the pressure or force exerted by the bulbous region 340 on the ear canal wall. Such a reduction in pressure provides for a comfortable, yet secure fit. And unlike a compressed foam tip that continuously exerts the same pressure or force on the ear canal wall in its compressed state, the release of gas or liquid from the cavity of 360 of eartip 300 reduces the force exerted on the ear canal. In this regard, the eartip 300 can exert an insertion force on the ear canal and a maintenance force on the ear canal where the maintenance force is less than the insertion force.

Figure 25A:
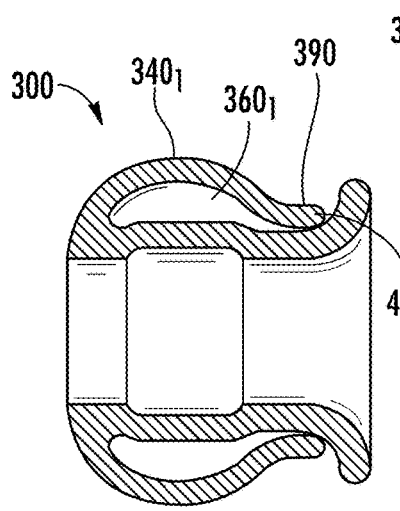
FIGS. 25A, 25B, and 25C illustrate further operations of another embodiment of an eartip.
Figure 25B:
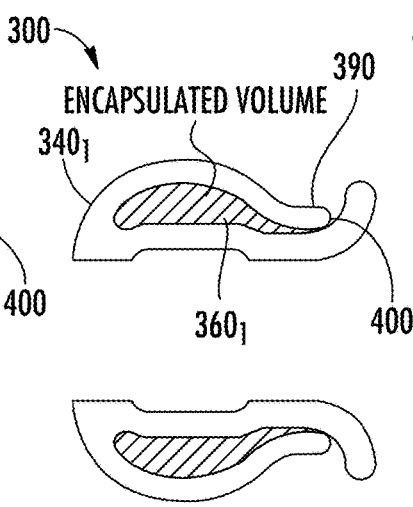
Figure 25C:
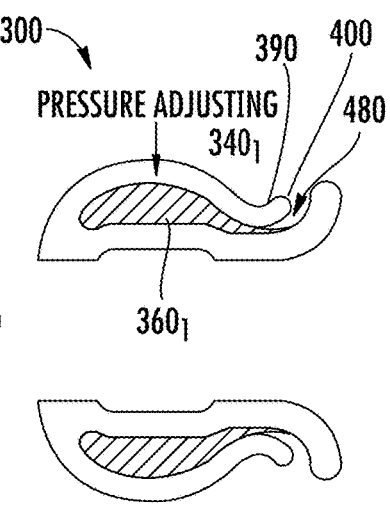

FIGS. 25A-C illustrate the pressure release arrangement of an eartip 300. When inserted into a user's ear canal, the bulbous region $340_1$ presses against the ear canal, which increases the pressure in cavity $360_1$. When increased pressure is exerted on the bulbous region $340_1$, the bulbous region $340_1$ moves radially pressing against the encapsulated volume of cavity $360_1$. If the pressure of the encapsulated volume increases, gas and/or fluid can escape, releasing pressure by leaving the closed interface between sealing section 390 with sealing tip 400 and inner channel wall 370 through gap or release opening 480. In other words, when pressure or force on the outer surface exceeds a threshold value, gas and/or fluid can escape, releasing pressure of the encapsulated volume. Further, the structural arrangement provides that if external air pressure increases, air can leak into the encapsulated volume, helping to maintain a constant pressure against the ear canal wall.

Figure 26A:
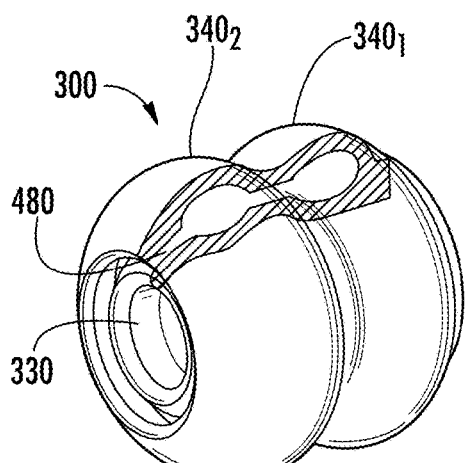
FIG. 26A illustrates another embodiment of an eartip in perspective view with a partial cross section thereof shown in the perspective view.
Figure 26B:
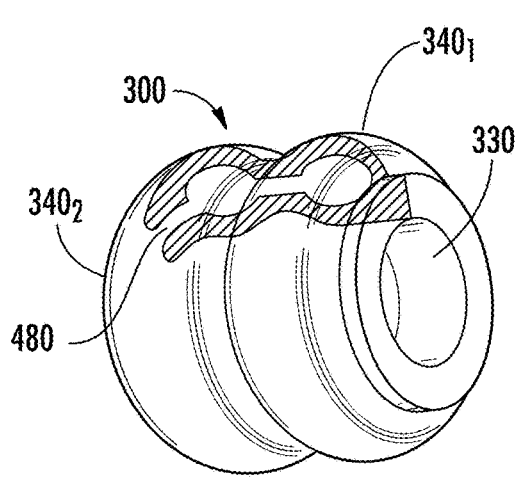
FIG. 26B illustrates another embodiment of an eartip in perspective view with a partial cross section thereof shown in the perspective view.
Figure 26C:
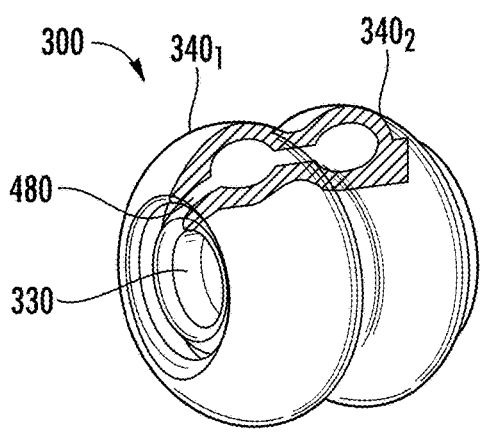
FIG. 26C illustrates another embodiment of an eartip in perspective view with a partial cross section thereof shown in the perspective view.

FIGS. 26A-C illustrate additional embodiments of the eartip 300 with a portion of each showing a cross section thereof. These embodiments illustrates an arrangement where the eartip 300 is open until a stent or an earphone or other device is received in the eartip 300. The channel 330 fits over, for example, a stent where the internal diameter of the channel 330 is smaller than exterior or circumferential diameter of the stent so that the channel 330 stretches until it touches the bulbous region $340_2$, sealing the interior of the eartip 300. In such an example, the internal portion of the eartip 300 can be stretched or flexed to come into contact with the outer portion of the eartip 300. The release opening 480, which is sealed when the bulbous region $340_1$ or $340_2$ contacts the channel 330, can be located in the ear canal direction or pointing outward from the ear canal. Additionally the bulbous region $340_1$ or $340_2$, or the outer shell of eartip 300, can be deformed inward when inserted into the ear canal, which will press the outer shell inward sealing the interior. Thus, the release opening 480 can be opened and closed by manipulating the eartip.

Figure 27A:
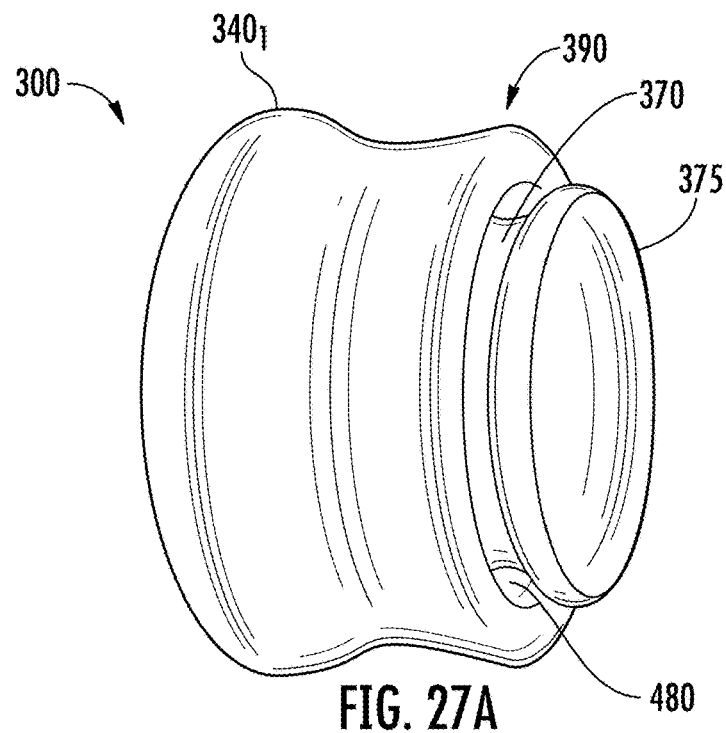
FIG. 27A illustrates a rear view of another embodiment of an eartip.
Figure 27B:
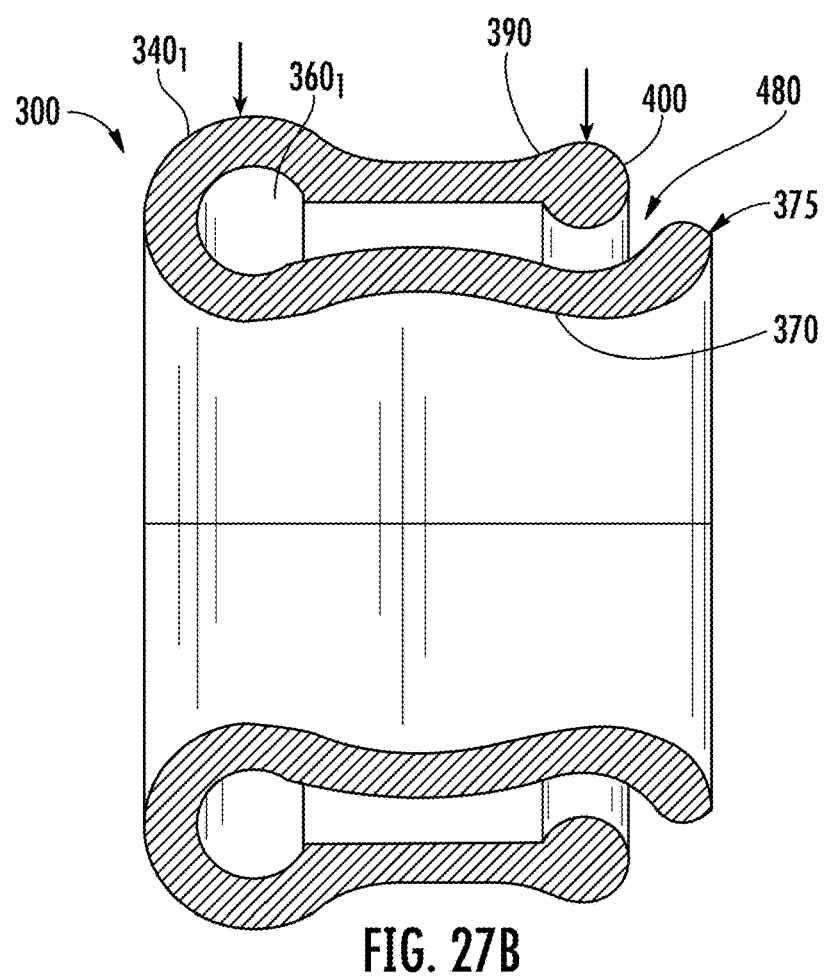
FIG. 27B illustrates a cross-sectional view of the eartip of FIG. 27A illustrating the operations of the eartip.

FIGS. 27A-B illustrate the operation of another embodiment of the eartip 300 with FIG. 27B being a cross sectional view of FIG. 27A. As shown with radially inward pointing arrows in FIG. 27B, the bulbous region $340_1$ can be pressed or flexed radially inward. Simultaneously, or independently, sealing section 390 with sealing tip 400 can also be pressed or flexed radially inward brining the sealing tip 400 into contact with the channel wall 370 and/or the lip or back ridge 375. Once the sealing tip 400 is seated, the cavity $360_1$ will be sealed.

Figure 28A:
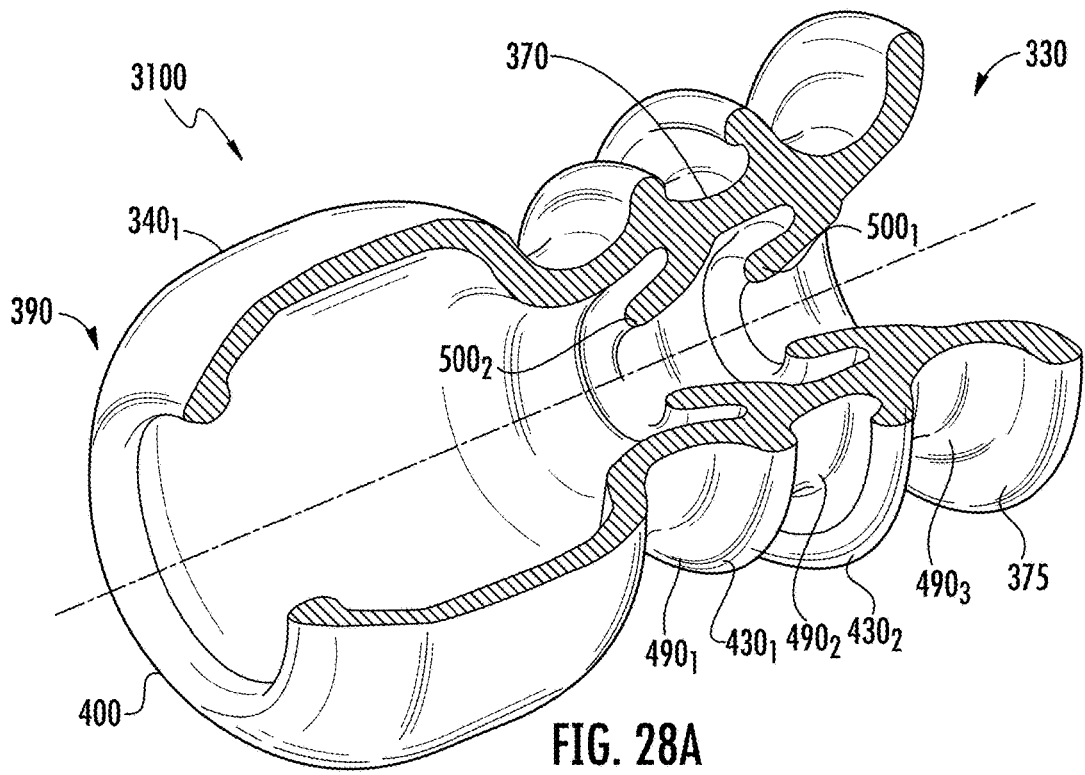
FIG. 28A illustrates a cutaway view of an embodiment of a molded eartip in an inverted flap manufactured form, prior to folding to form a final or insertion arrangement eartip.
Figures 28B, 28C, 28D, 28E:
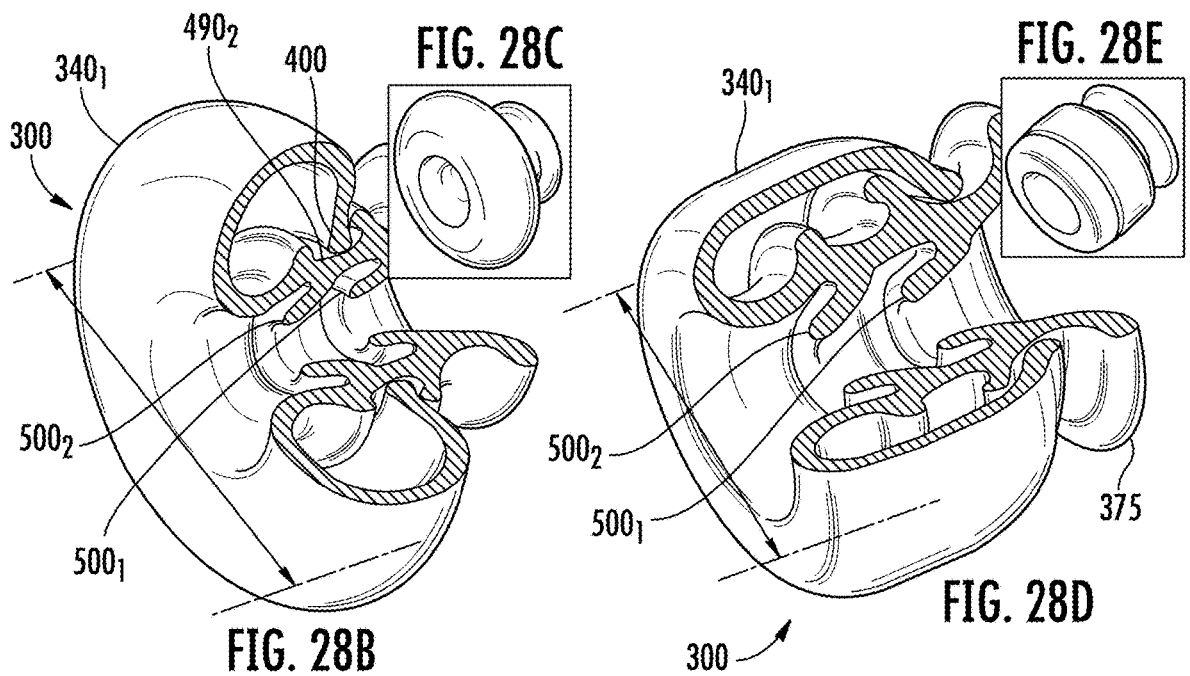
FIG. 28B illustrates a cutaway view of the embodiment of a molded eartip of FIG. 28A after folding to a first size for insertion in an ear canal.
FIG. 28C illustrates a perspective view of the embodiment of FIG. 28B.
FIG. 28D illustrates a cutaway view of the embodiment of a molded eartip of FIG. 28A after folding to a second size for insertion in an ear canal.
FIG. 28E illustrates a perspective view of the embodiment of FIG. 28D.

FIG. 28A illustrates a 270 degree cutaway view of an embodiment of a molded eartip 300 in an inverted flap manufactured form, prior to folding to form a final or insertion arrangement eartip 300. Such an embodiment is size adjustable, and designed to be used on multiple sized stents with different outer diameters. FIG. 28B illustrates a 270 degree cutaway view the eartip 300 of FIG. 28A in a first ear canal size configuration, while FIG. 28C illustrates a 360 degree view thereof. FIG. 28D illustrates a 270 degree cutaway view the eartip 300 of FIG. 1 in a second ear canal size configuration, while FIG. 28E illustrates a 360 degree view thereof.

To configure eartip 300 for use, sealing tip 400 of sealing section 390 is folded over itself so that the inside of bulbous region $340_1$ faces radially outward, as shown in FIGS. 28B-E, while the outside of bulbous region $340_1$ becomes the inside of the eartip 300 as shown in FIGS. 28B and D. The sealing section 390 with sealing tip 400 rests in a recess $490_1$ formed by internal sealing ridge $430_1$ to form eartip 300. As shown in FIG. 28A, the eartip 300 can have a plurality of internal sealing ridges $430_{1-n}$, here shown as two internal sealing ridges $430_{1-2}$. Internal sealing ridges $430_{1-2}$ helps to retain the sealing section 390 with sealing tip or lip 400 near recess $490_1$ to form an eartip 300 of a first size. To form a second size, the sealing section 390 with sealing tip or lip 400 is adjusted to rest in recess $490_3$ formed by lip or back ridge 375.

Figure 28F:
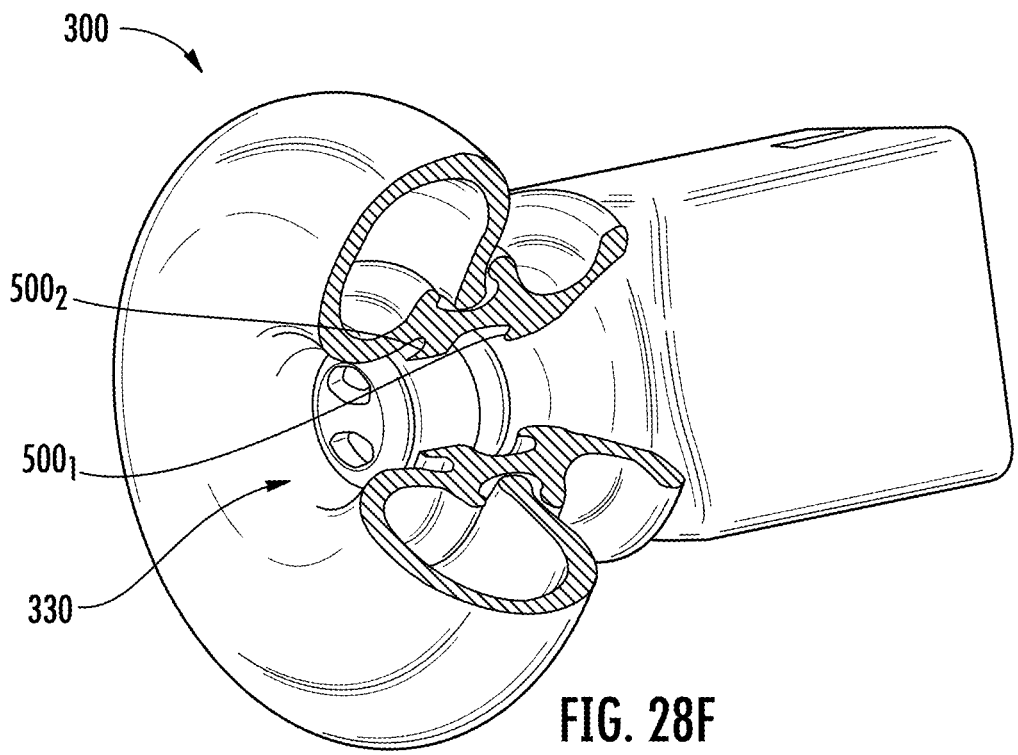
FIG. 28F illustrates a first sized stent coupled to the embodiment of FIG. 28B.
Figure 28G:
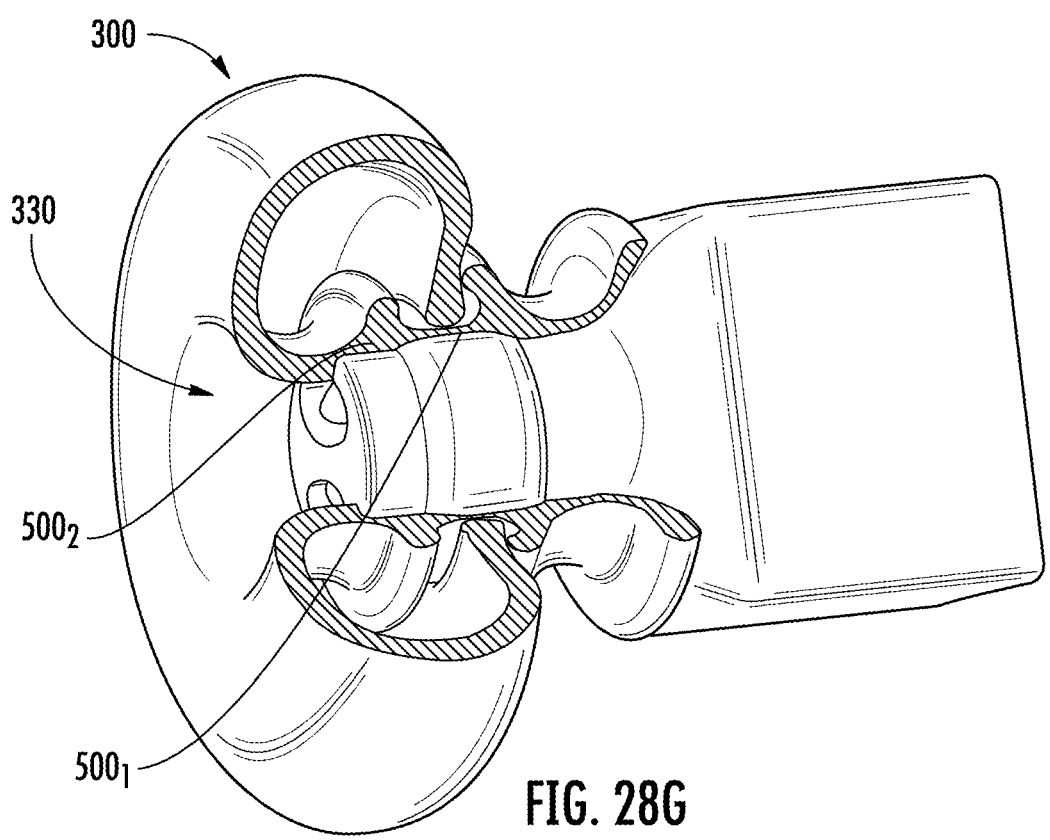
FIG. 28G illustrates a second sized stent coupled to the embodiment of FIG. 28B.

Further, the eartip 300 can include deformable, multi-stent structure(s) $500_{1-n}$, which flex or deform when various sized stents push past and deform the structures $500_1$ and $500_2$ shown in FIGS. 28A, 28B and 28D. Such multi-stent structure(s) $500_{1-n}$ can be angled in direction of stent insertion. Such arrangement allows the channel 330 to receive a stent easily with a wide opening while increasing pressure and grip on the stent as it passes the multi-stent structure(s) $500_{1-n}$. For example, FIG. 28F illustrates a smaller stent pushed into the channel or center core 330 of the embodiment of FIG. 28B with deforming structures $500_1$ and $500_2$ such that the stent is supported by the deformable, multi-stent structure $500_1$ and $500_2$. In another example, FIG. 28G illustrates a larger stent pushed into the channel or center core 330 of the same embodiment deforming the structures $500_1$ and $500_2$ also supporting the stent.

Figure 29:
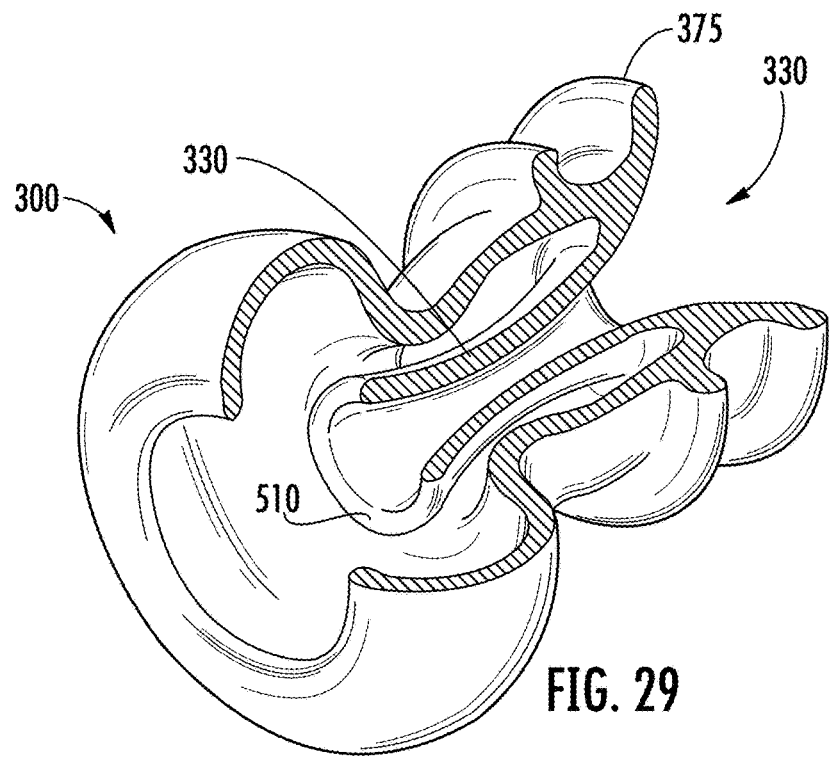
FIG. 29 illustrates a cutaway view of another embodiment of a molded eartip after folding to form a final or insertion arrangement eartip.
Figure 30:
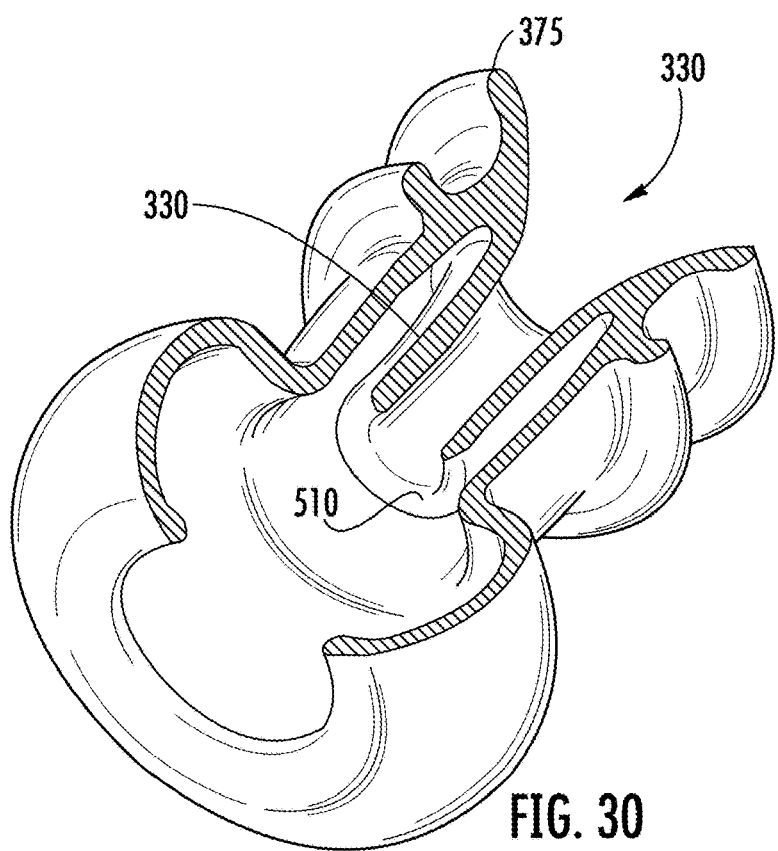
FIG. 30 illustrates a cutaway view of another embodiment of a molded eartip after folding to form a final or insertion arrangement eartip.

FIGS. 29-30 illustrate various additional non-limiting embodiments of eartip 300, including variations of the internal diameter of channel 330. For instance in FIG. 29, internal diameter of channel 330 increases distally and proximally from the midpoint of channel 330. Thus, the ends of channel 330 are both flared while the midpoint provides a flexible, narrow passage for receiving a stent. FIG. 30 illustrates a channel 330 that narrows travelling from the lip or back ridge 375. As shown in both embodiments of FIGS. 29-30, an additional sizing structure 510 can be provided. Here, the additional sizing structure is a reinforced annular ring to grip an inserted stent.

Figure 31:
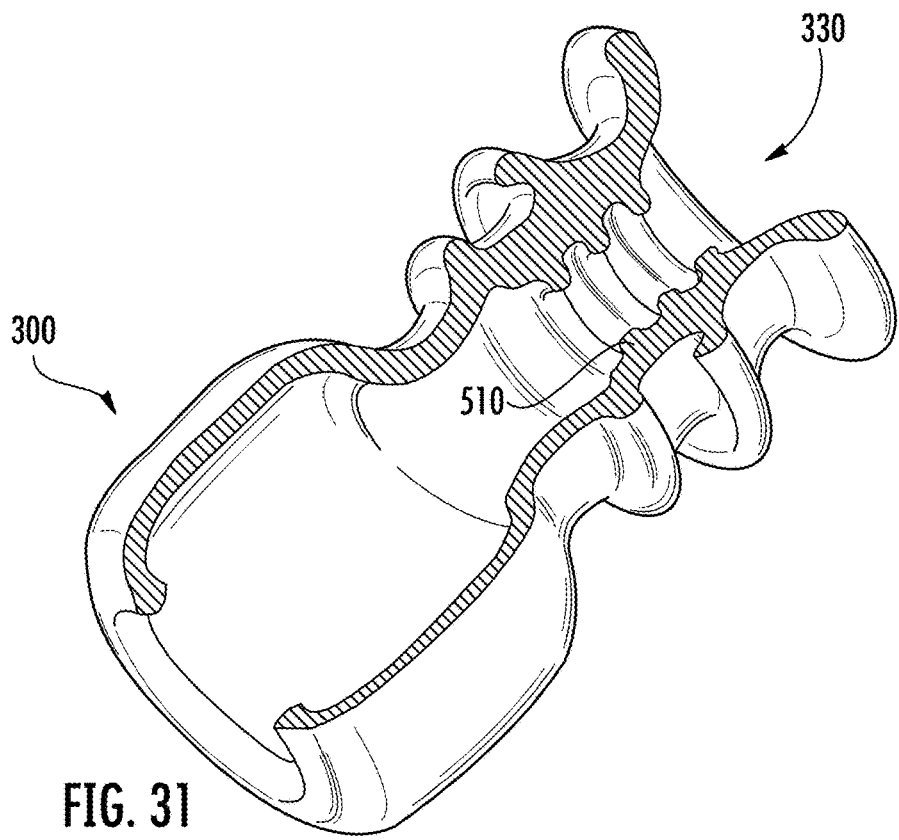
FIG. 31 illustrates a cutaway view of another embodiment of a molded eartip after folding to form a final or insertion arrangement eartip.
Figure 32:
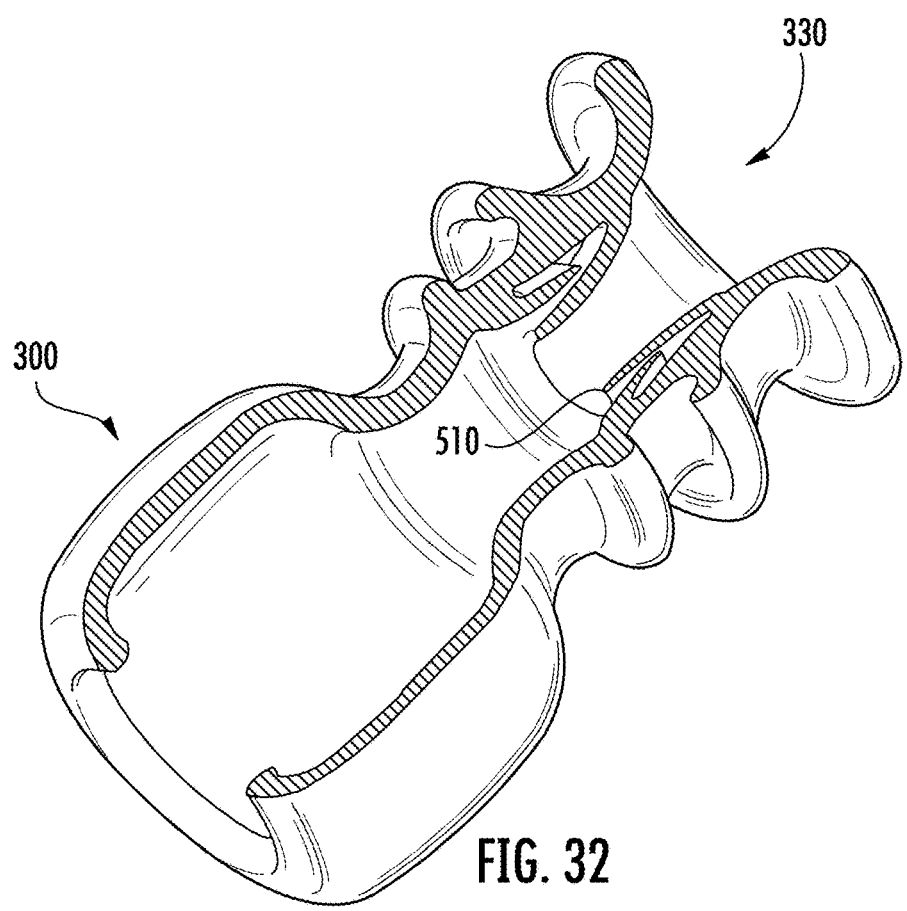
FIG. 32 illustrates a cutaway view of another embodiment of a molded eartip after folding to form a final or insertion arrangement eartip.

FIGS. 31-32 illustrate various additional non-limiting embodiments of eartip 300, including variations of the internal diameter of channel 330 and with additional sizing structures 510, which can provide a restricting force. As shown in FIG. 31, the additional sizing structures 510 can be channel ridges that can be annular. As shown in FIG. 31, the additional sizing structures 510 can be a leaf spring arrangement where portions of channel 330 are angled opposite to each other an arranged to compress upon insertion of a stent. The portions of channel 330 angled opposite to each other can be biased to resist radially outward movement until the force for of the angled portions is overcome to ensure a snug fit.

FIG. 33 illustrates a cross section of another embodiment of eartip 300 that is pluggable with an earplug structure 530 so eartip 300 becomes earplug 300. The earplug is plugged or sealed to attenuate sound distribution. Any of the eartips can function as an earplug if plugged with an earplug structure 530 or sealed or closed.

The eartip 300 includes bulbous region 340 formed of membrane with a sealing section, here a lip, 390 that contacts internal sealing ridge 430, encapsulating a volume in cavity 360. Note that the encapsulated volume need not be completely sealed, rather when viewed from the front or behind, no part of the gap or release opening 480 between the lip and any part of internal sealing ridge 430 is viewed. Thus, in at least one exemplary embodiment, an acoustic wave traveling from right to left will have an obstructed straight path to the encapsulated volume of cavity 360, so that the acoustic wave must bend to enter the volume of cavity 360. Therefore the sealing section or lip 390 need not contact the channel wall 370 or internal sealing ridge 430. When the eartip 300 is inserted onto a stent, for an earphone eartip, and/or into an ear canal, the ear canal wall will press the sealing section or lip 390 normally against the channel wall 370 or internal sealing ridge 430. However, this is not required for the eartip to distribute the contact force to enhance comfort. As long as the gap or release opening 480 is not viewed from the front (someone looking from the eartip 300 backward prior to insertion of an earplug) or back (someone looking into the ear at the earplug), the acoustic wave will not see the gap or release opening 480 without bending.

The eartip 300, because of its design, can be adjusted to several sizes (various outer diameters) as illustrated in the embodiments of FIGS. 34A and 34B. The dotted lines in FIG. 34A show how the eartip 300 can be manipulated to move sealing section 390 between two positions to provide different sizes as shown in a comparison of FIGS. 34A and 34B.

Additionally, an eartip 300 can be converted to an earplug, by plugging the channel or core 330 where an earphone stent would be inserted as shown in FIG. 35. In the embodiments illustrated at FIGS. 33-35, the eartip 300 size is the outer dimeter of the body 310 (e.g., S1, S2, S3, S4, and D, respectively. The internal sealing ridge 430 radial distance can be fabricated so as to retain the seal section or lip 390 against the internal sealing ridge or ledge 430 even when inserted such that there is an force in the axial direction along the channel or shaft 330 deforming or flexing the bulbous region 340 and/or sealing section 390, for example approximately 1-4 mm radially from the outside surface of the channel wall 370.

FIG. 34A illustrates a cross section of an earplug eartip. Two sizes are shown S3 and S4, dependent upon placement of the sealing section or lip 390 against internal sealing ridge or ledge 430 or lip or back ridge 375, respectively. Altering the internal sealing ridge or ledge 430 or lip or back ridge 375 location (e.g., d1 and d2) can also change the size of the eartip as well as changing length 'l' of sealing section or lip 390. Note that the thickness (t) of the body 310 can be varied along the length (l) to aid in deformation during folding (moving the sealing section or lip 390 backward toward tab 520. The tab 520 can be designed to aid in grasping during insertion an removal, for example it can extend approximately 3-20 mm out from the back of lip or back ridge 375.

FIG. 34B illustrates a cross section of an earplug eartip 300 in its smallest size S2. FIG. 35 illustrates a cross section of an earplug eartip 300, where the configuration shown has two internal sealing ridges $430_1$ and $430_2$ and lip or back ridge 375 allowing three sizes on a single eartip 300, noting that a single size can also be fabricated using a single ridge or ledge.

Figure 36:
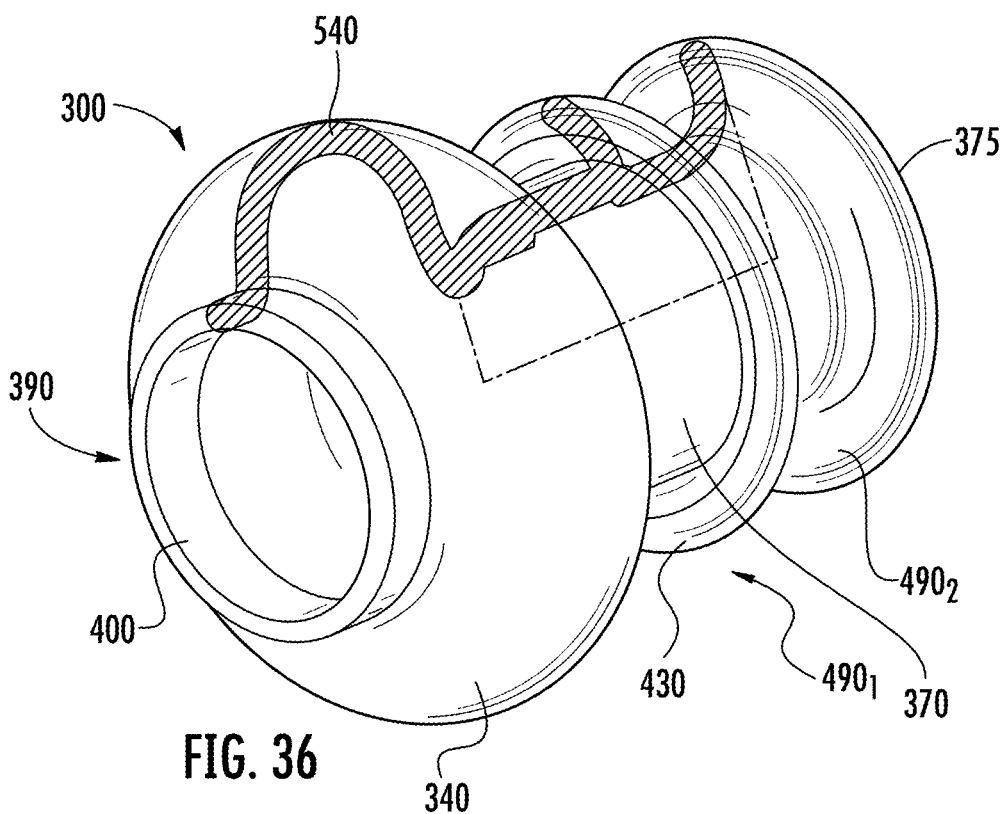
FIG. 36 illustrates a front view of another embodiment of an eartip in perspective view with a partial cross section thereof shown in the perspective view.
Figure 37:
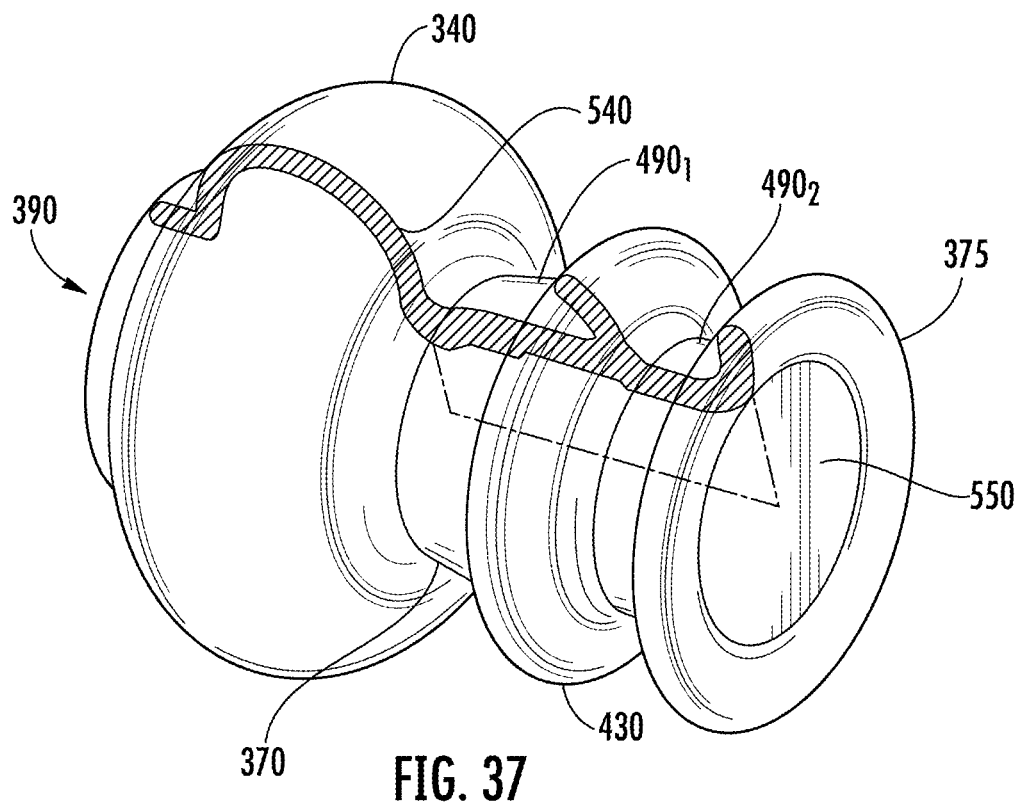
FIG. 37 illustrates a rear view of the eartip of FIG. 36.

FIG. 36 and FIG. 37 illustrate a front view (FIG. 36) and a rear view (FIG. 37) of one molding technique molding an inverse of the eartip bulbous region 340 that can form a flange. The bulbous region 340 is folded back upon a channel wall 370 that forms a longitudinally extending stent to configure the eartip in its usable form for use with an earphones or as earplugs. The sealing tip 400 of sealing section 390 when folded back can sit within recesses $490_1$ formed by internal sealing ridge $430_1$ and recess $490_2$ formed by lip or back ridge 375. FIG. 36 illustrates the cross section 540 of an earplug eartip 300 and illustrates the sealed core backing 550.

Figure 38A:
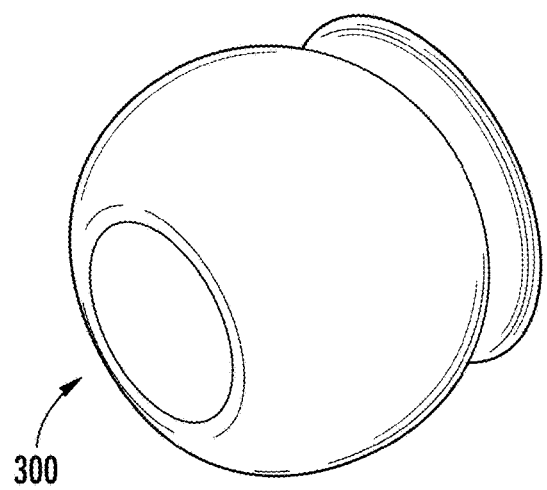
FIGS. 38A-D illustrate another embodiment of an earplug in different configurations.
Figure 38B:
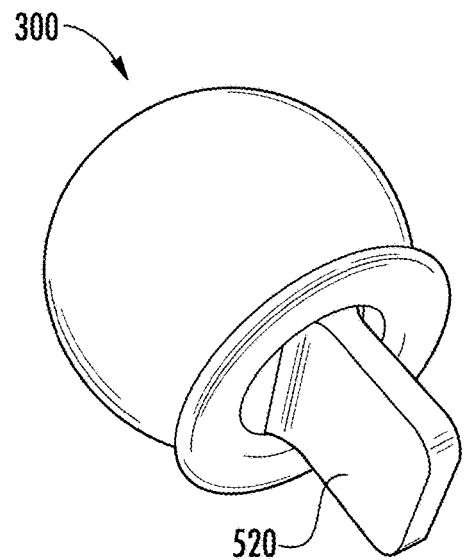
Figure 38C:
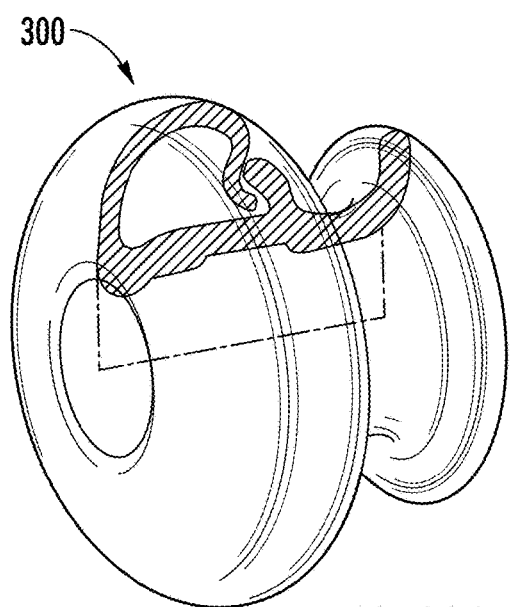
Figure 38D:
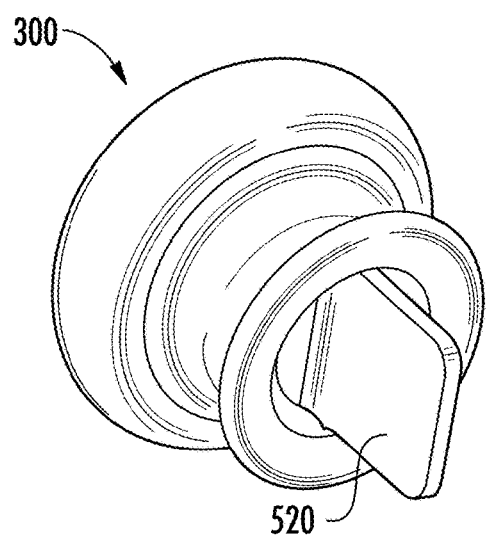

FIGS. 38A-D illustrate various views of embodiments of an adjustable earplug with two sizes due to two ledges or ridges as disclosed herein and tab 520. FIGS. 38A and 38B illustrate a smaller diameter version and FIGS. 38C and 38D illustrate a larger diameter version.

Figures 39A, 39B:
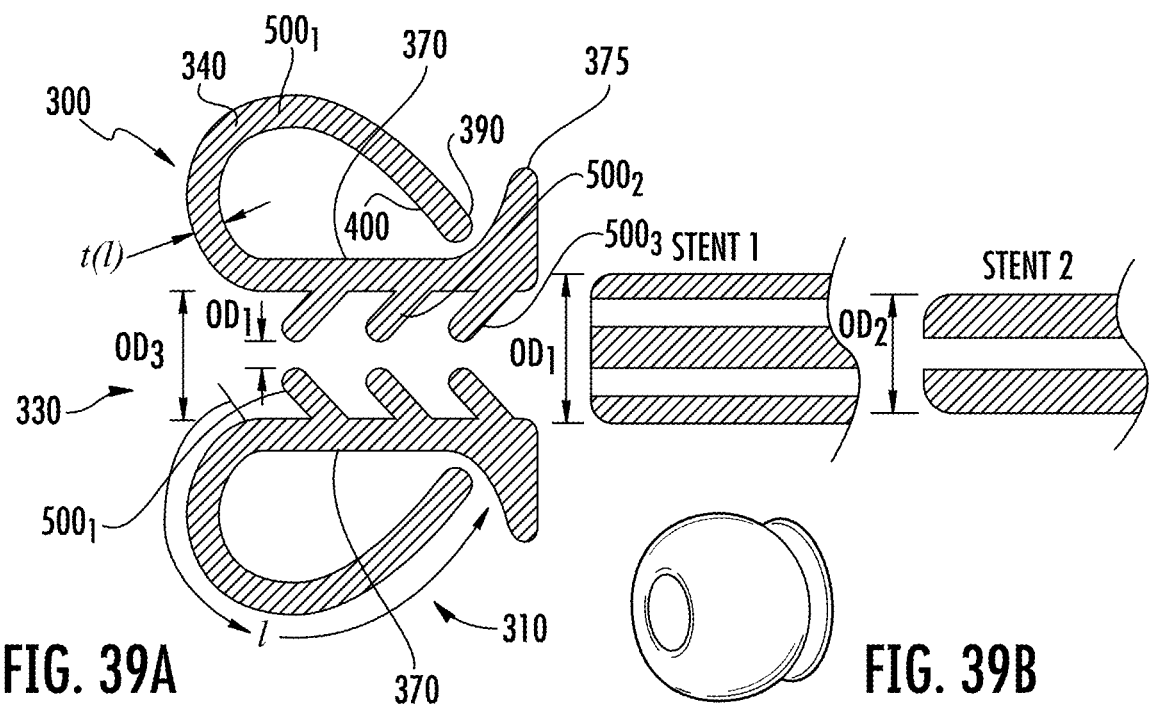
FIG. 39A illustrates a cross sectional view of another embodiment of an eartip.
FIG. 39B illustrates a perspective view of the embodiment of FIG. 39A.

FIGS. 39A and 39B illustrate a cross section of another embodiment of eartip 300, which can be configured to fit on an earphone allowing passage of acoustic content through a central tube, or as an earplug. In this example, eartip 300 can fit or receive multiple sized stents (e.g., stent 1 (OD1), which is shown with multiple lumens, stent 2 (OD2)). Flexible multi-stent structures (e.g., $500_1$, $500_2$, and $500_3$) have a base that is attached to, or protrude from the same membrane as, the inner core or channel wall 370 surface having an inner diameter OD3. The flexible multi-stent structures (e.g., $500_1$, $500_2$, and $500_3$) can extend radially inward forming a smallest inner diameter OD4. Hence, stents can have outer diameters >OD4 and less than about a OD3+threshold, where the threshold is chosen to take into account the flexibility of the eartip's 300 channel or core walls 370, for example 10% of OD1 or OD2. The elongated body 310 or regions thereof, such as bulbous region 340, can have thickness along the length (l) of the body 310 that can be varied for various purposes. For example, t(l) values in a range 1 min (e.g., approximately 3 mm) to 1 max (e.g., approximately 8 mm) can be thinner to reduce pressure on an ear canal wall. Size or max outer diameter of eartip 300 formed by the folded membrane that is bulbous region 340 is accomplished by the contact of the sealing section 390 with a sealing tip 400 on the retaining surface or lip or back ridge 375.

Figure 40:
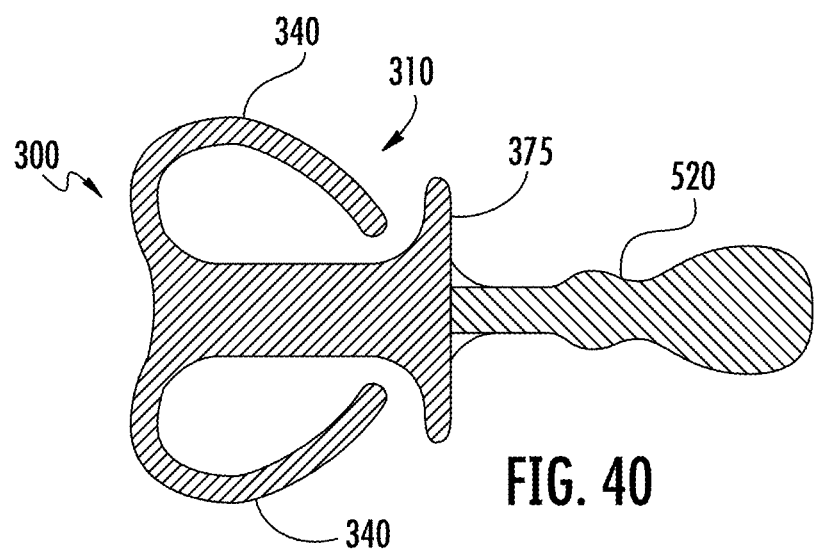
FIG. 40 illustrates a cross section of an eartip earplug shown in FIG. 39.

FIG. 40 illustrates a cross section of an eartip earplug shown in FIG. 39. In this example, the channel 330 is sealed or plugged.

Figure 41A:
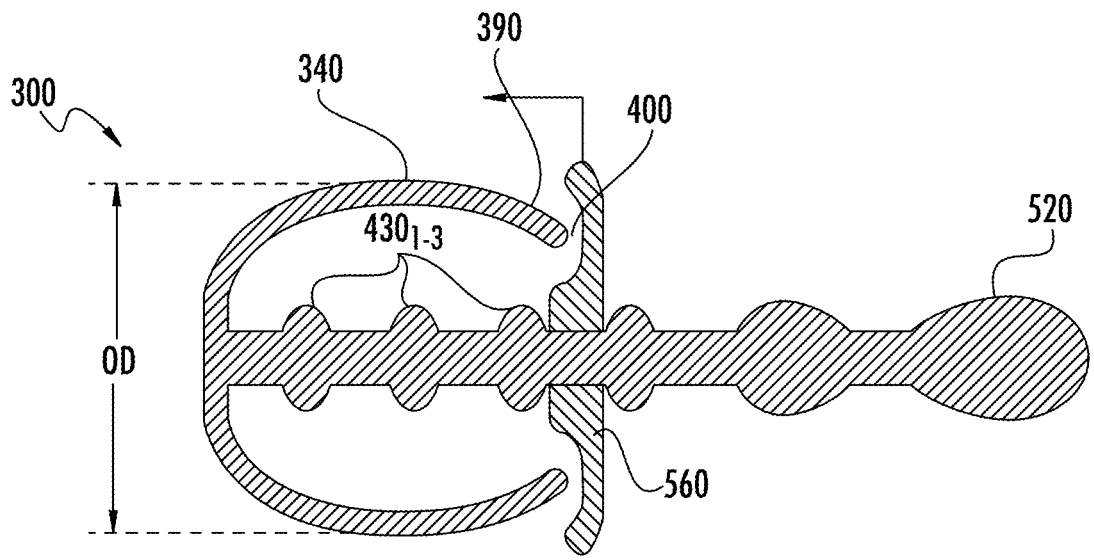
FIG. 41A illustrates a cross sectional view of another embodiment of an eartip.
Figure 41B:
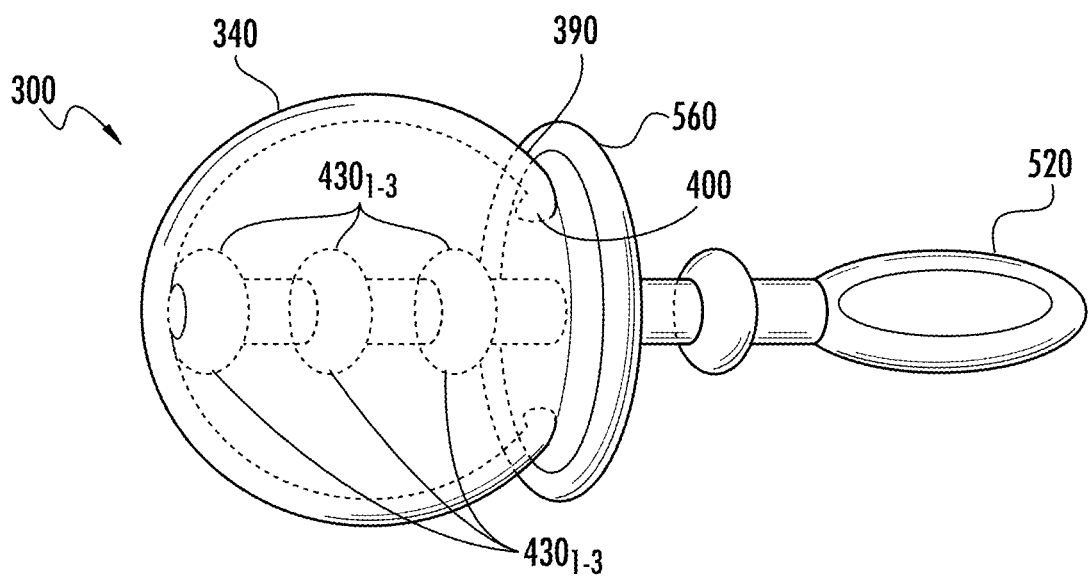
FIG. 41B illustrates the embodiment of FIG. 41A in a perspective view with portions illustrated as transparent.

In FIG. 41A, a cross section of an eartip earplug or earphone tip 300 is shown. In this example, movable ledge 560 is shown. Movement of the movable ledge 560 along the longitudinal axis of the eartip 300, in the direction of movement (dm), provides for discrete or incremental size adjustment. In this particular embodiment, the size OD is adjusted by moving the movable ledge 360 between internal seal ridges $430_{1-3}$, while a user grasps tab 520. In one arrangement, the movable ledge 560 spins in a corkscrew fashion to move back and forth along the longitudinal axis of eartip 300. FIG. 41B illustrates the embodiment of FIG. 41A in a perspective view with portions illustrated as transparent.

FIGS. 42 and 43 illustrate cross sections of an eartip 300 earplug or earphone tips, which can be discretely size adjusted by moving the contact position of the sealing section 390 in the direction of movement (dm) between internal sealing ridge $430_{1-2}$, while user grasps tab 520. The embodiment of FIG. 5 includes a terminal grip 570 with a concave end that receives and grips around an internal sealing ridge 430. Thus, terminal grip 570 grips and rests on an internal sealing ridge 430 rather than between internal sealing ridges 430. Note also that the internal sealing ridges 430 can have a non symmetric shape to facilitate a predominate direction of movement as shown in the breakout zoomed perspective of FIG. 43. Also, the embodiment of FIG. 43 illustrates an optional core channel 670 with an optional core vent 680. The core channel 670 and core vent 680 can provide a pathway for leakage of the enclosed volume.

Figure 44A:
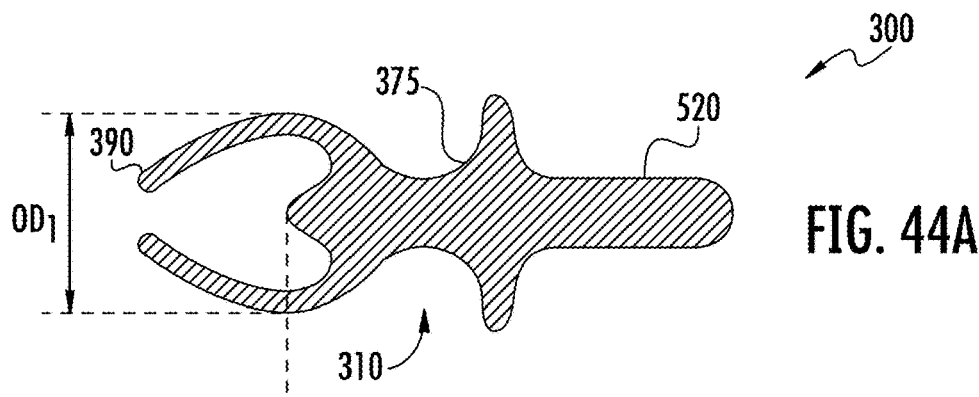
FIGS. 44A-44C illustrate a cross sectional view of varying embodiment of an eartip.
Figure 44B:
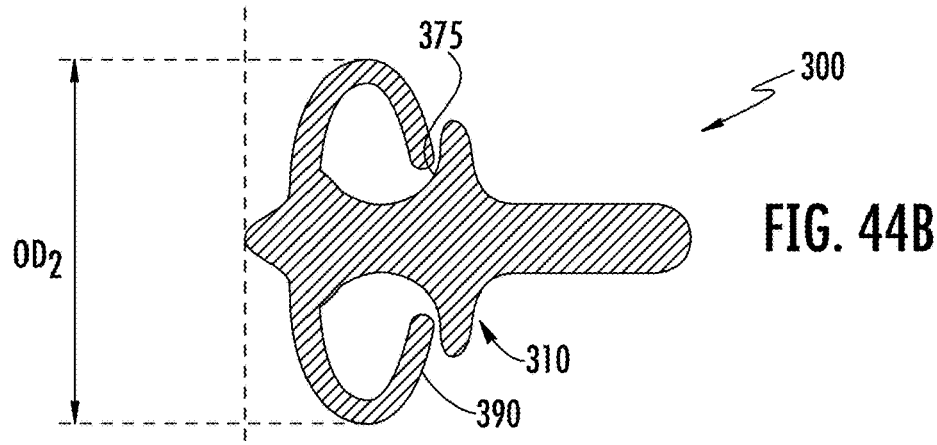
Figure 44C:
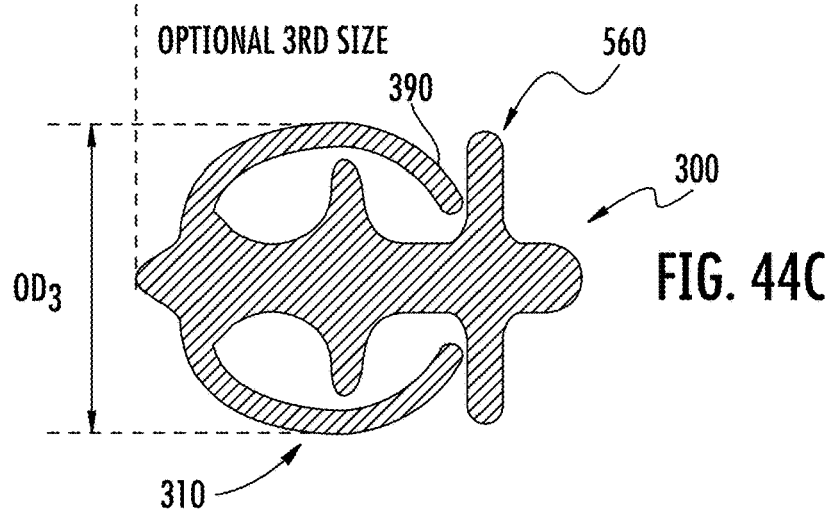

FIG. 44A-C illustrate a cross section of embodiments of an eartip or earplug 300, which can be size adjusted by folding the membranes of the elongated body 310 moving the sealing section 390 to various contact positions (e.g., lip or back ridge 375 and optional and movable ledge 560, meaning the optional and movable ledge 560 can added or removed to eartip 300 as needed. As discussed previously, the eartip 300 of FIG. 44 is shown with a configuration out of a negative mold, the membrane thereof can be folded as shown in FIGS. 44B and 44C.

Figure 45:
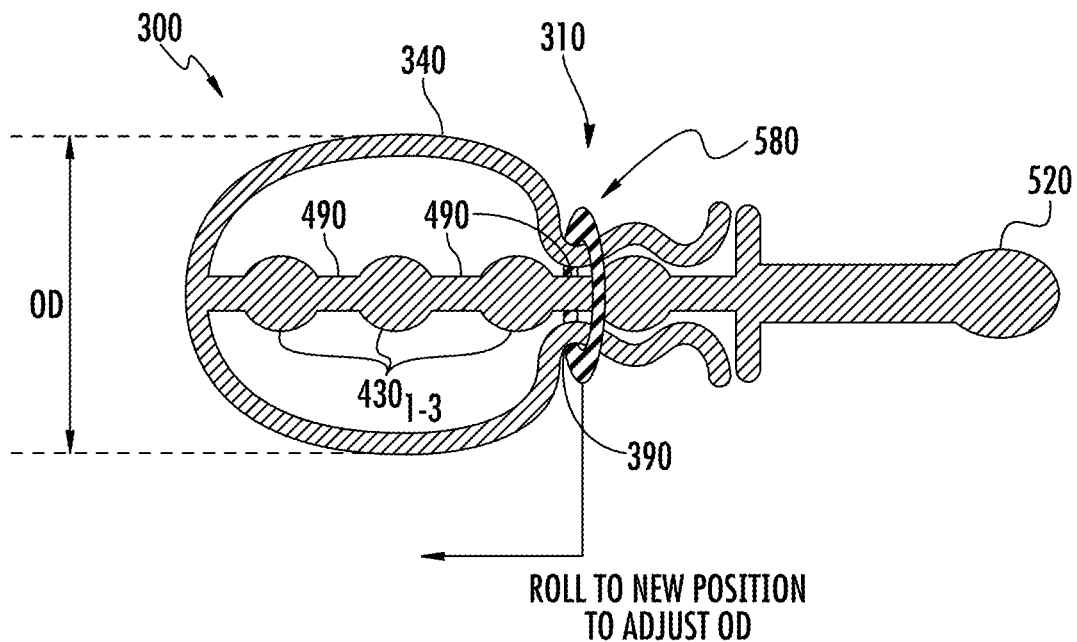
FIG. 45 illustrates a cross sectional view of another embodiment of an eartip.

In FIG. 45, another embodiment of an eartip or earplug 300 is illustrated that features discretely size adjustment by moving a flexible compressing member 580, such as grommet. The flexible compressing member 580 compresses a portion of the elongated body 310 to form the sealing section 390 where the flexible compressing member 580 is located. For example, the sealing section 390 can seat in recess 490. In one embodiment, size manipulation does not depend on axial movement of bulbous region 340 or sealing section 390. Instead, constricting the bulbous region 340 or sealing section 390 is achieved as the as the flexible compressing member 580 is moved.

Figure 46:
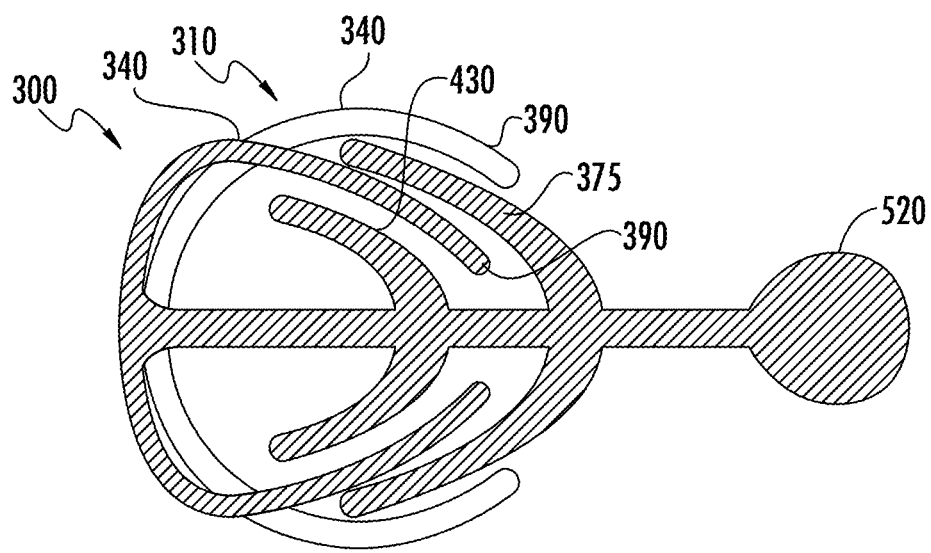
FIG. 46 illustrates a cross sectional view of another embodiment of an eartip.

In FIG. 46, an eartip or earplug 300 can be discretely size adjusted by moving the contact position of the sealing section 390 to different resting positions, noting that the term discretely herein refers to a range of size about a position, the range due to the contact point moving slightly between retaining structures and the flexibility of the membrane of the elongated body 310.

Figure 47A:
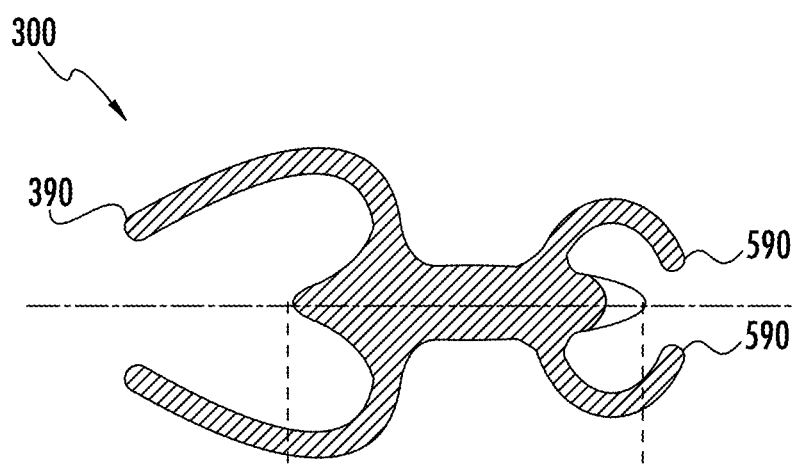
FIGS. 47A-C illustrate different configurations of a cross sectional view of another embodiment of an eartip.
Figure 47B:
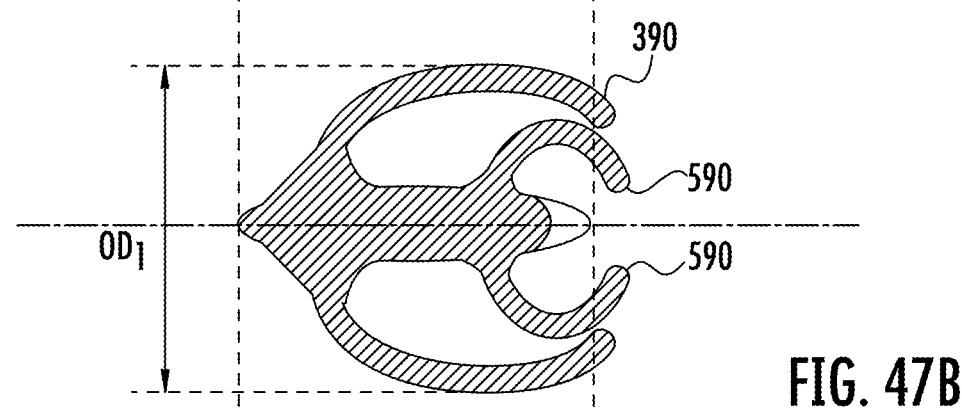
Figure 47C:
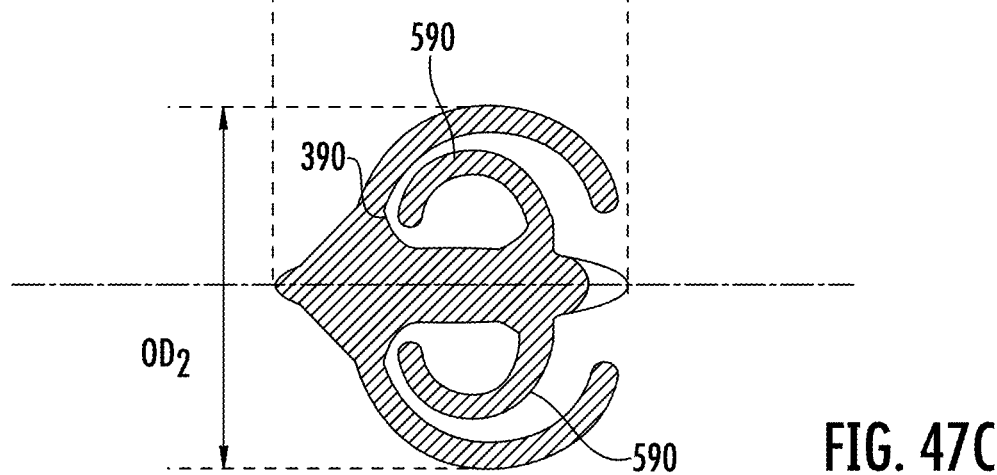

In FIGS. 47A-C, an embodiment of the eartip or earplug 300 that can be discretely size adjusted by folding an invertible arm 590, which can be an annular flange. Inverting the invertible arm 590 between a first position and a second position changes the contact position of the sealing section 390. In FIG. 47B, the size of the eartip 300 (e.g. OD1) is formed by folding the membrane of elongated body 310 over the invertible arm 590. In FIG. 47C, the size of the eartip 300 (e.g. OD2) is formed by folding the membrane of elongated body 310 over the inverted invertible arm 590.

Figure 48A:
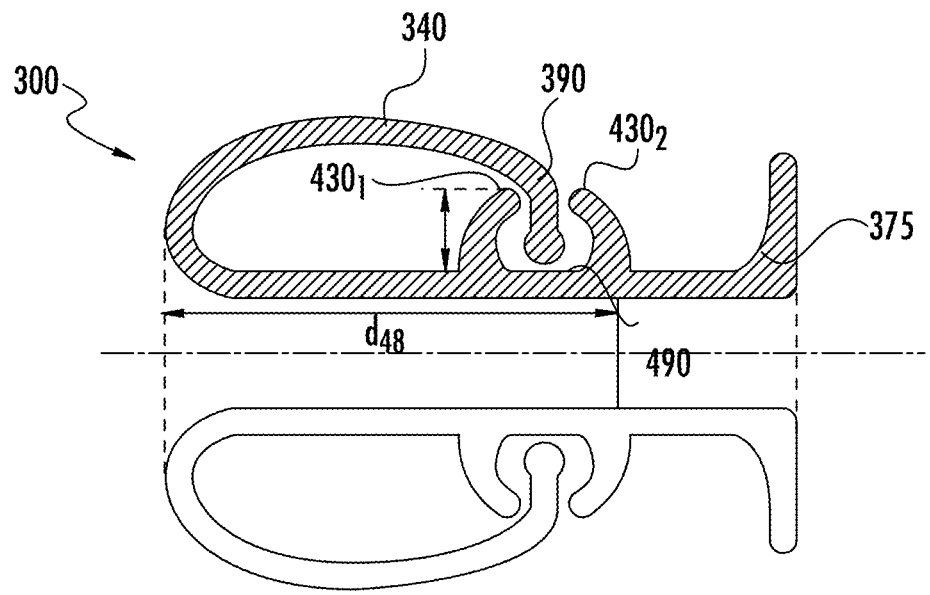
FIGS. 48A and 48B illustrate different configurations of a cross sectional view of an embodiment of an eartip.
Figure 48B:
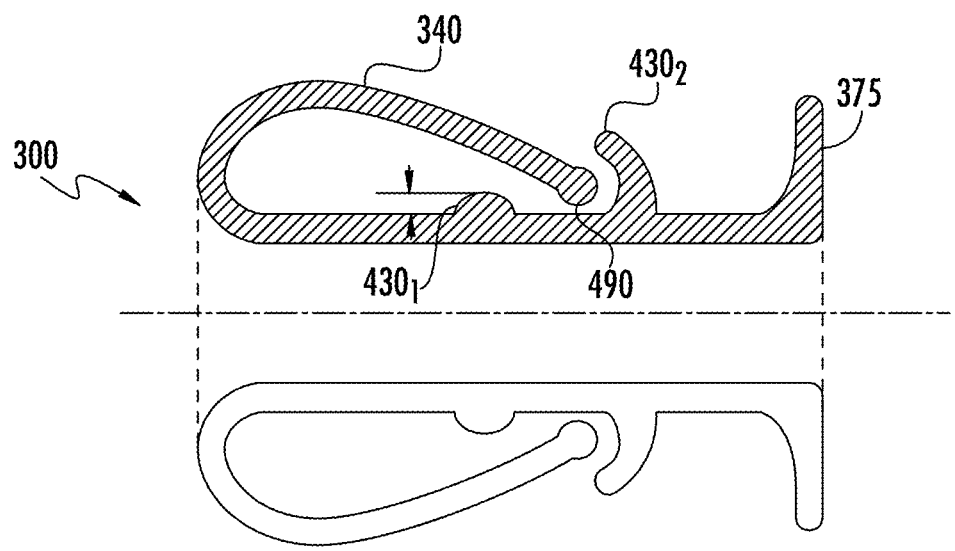

FIGS. 48A and 48B illustrate different configurations of a cross sectional view of embodiments of an eartip or earplug 300, which can be shape adjusted. As shown in FIG. 48A, internal sealing ridge $430_1$ is orientated and curved towards second internal sealing ridge $430_2$ (which could also be lip or back ridge 375 in some arrangements). In FIG. 48A, the sealing section contacts in recess 490. The sealing ridge $430_1$ forces the bulbous region 340 to have an relatively increased diameter. However, the sealing ridge $430_1$ can be moved along the longitudinal axis of eartip 300 to change the size or diameter of bulbous region 340. Further, sealing ridge $430_1$ with height (slh) can be flexible or compressible so that it can be collapsed or reduced in size, and/or changed its orientation from being orientated toward sealing ridge $430_2$ to being orientated away from sealing ridge $430_2$ as shown in FIG. 48B to reduce the size of bulbous region 340.

Figure 49A:
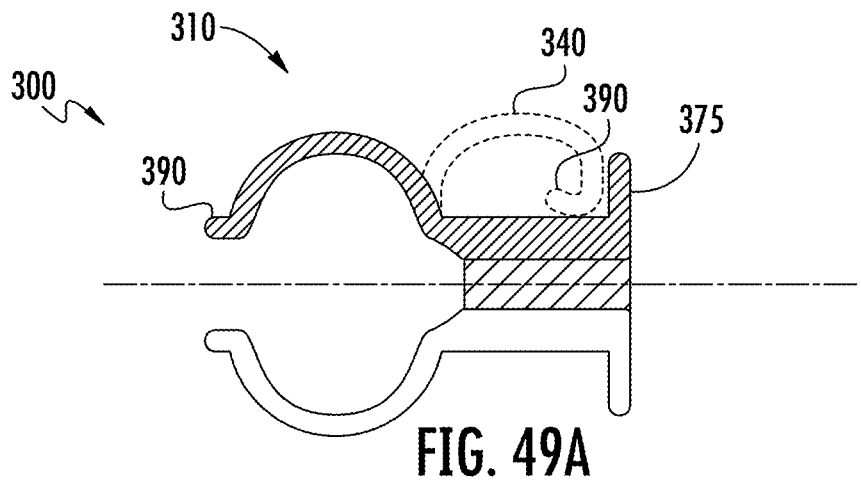
FIGS. 49A and 49B illustrate different configurations of a cross sectional view of an embodiment of an eartip.
Figure 49B:
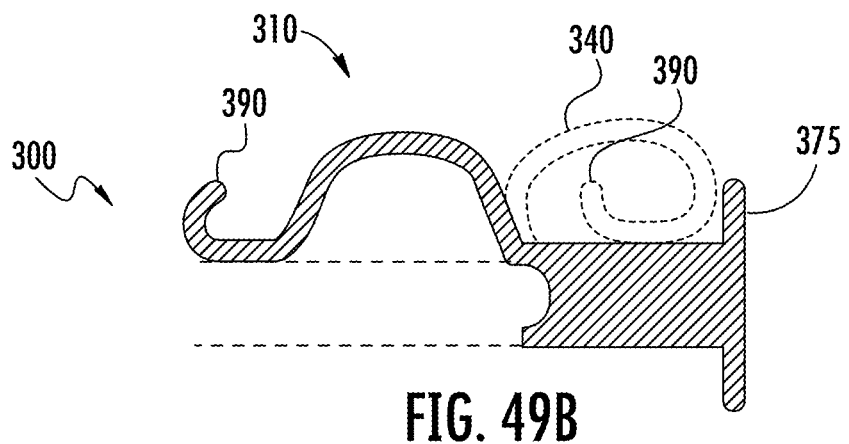

FIGS. 49A-49B illustrate a cross section of an eartip or earplug 300 where various shapes of the membrane of the elongated body 310 can be constructed to modify the final folded shape, enhance sealing and control feedback pressure. For example sealing section 390 can be formed in the negative mold stage and then folded to (as in FIG. 49B) to provide additional radial resistance.

Figure 49C:
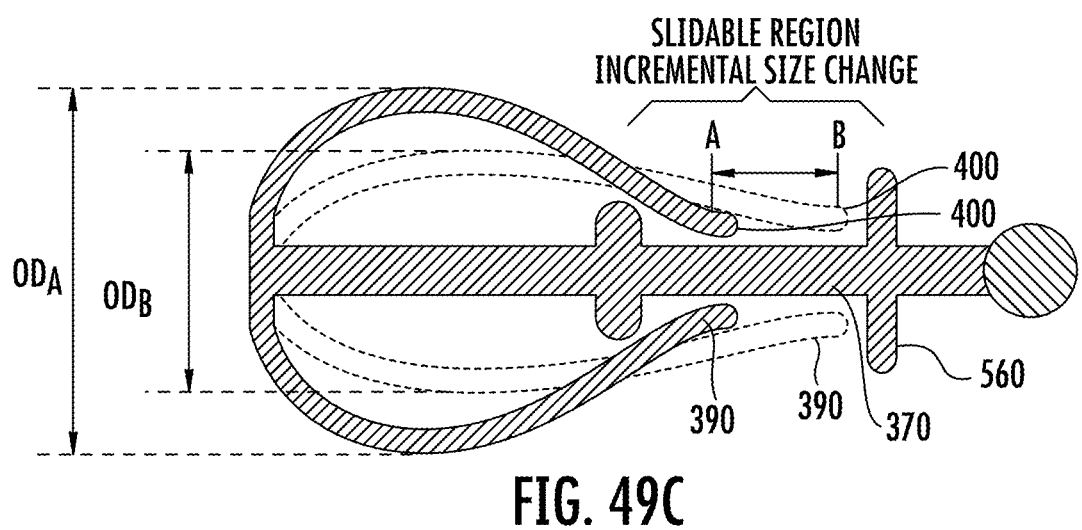
FIG. 49C illustrates a cross sectional view of another embodiment of an eartip with a sealed core that functions as an earplug.

FIG. 49C illustrates an eartip or earplug with a sealed core (or an earphone (open acoustic channel)) that can be continuously sized by the contact of the membrane of body 310 between an initial position (A) related to the configuration prior to insertion and a retaining ridge (B) related to a smaller size, whereupon insertion the sealing section 390 will slide along the shaft or closed channel wall 370, adjusting size, between the two positions (A to B). In this embodiment, size can advantageously be adjusted through a range rather than having discrete steps. For example the movable ledge 560 (near position B) can be removed resulting in an even smaller size being available. The sealing tip 400 can be designed to facilitate sliding, and the surface can be low friction as well (e.g., permeated with mineral oil).

Figure 50:
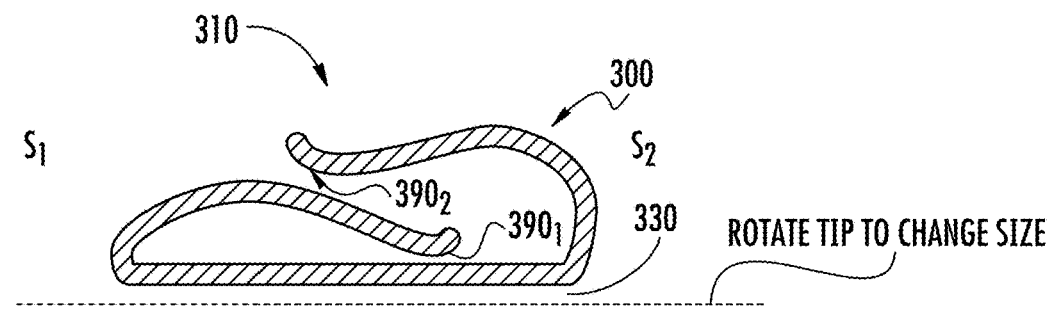
FIG. 50 illustrates a cross section of a multi-size eartip and FIG. 51 illustrates another embodiment of an eartip.

FIG. 50 illustrates a cross section of a multi-size eartip 300, which can be configured to fit on an earphone allowing passage of acoustic content through a central tube or channel 330, or as an earplug 300. The eartip 300 can be rotated to change which end inserts in the ear, effectively changing the size of the eartip 300 from a first size $S_1$, such as medium, to a second size $S_2$, such as large. Note that sealing sections $390_1$ and $390_2$ can be designed such that they assist sliding and/or deformation of the membranes of body 310. Alternatively, the eartip 300 can be rotated about its longitudinal axis to chance the size.

Figure 51:
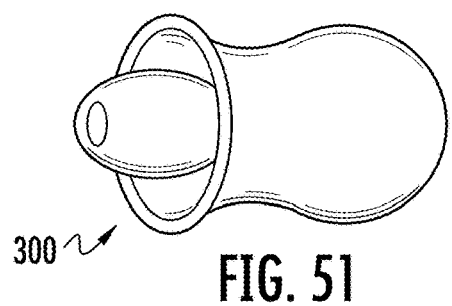

FIG. 51 illustrates a perspective view of a bell shaped eartip 300.

Figure 52:
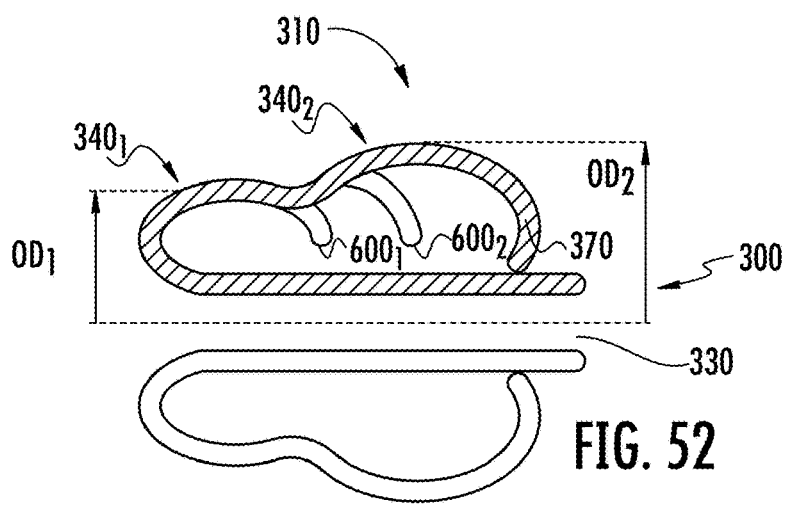
FIG. 52 illustrates a cross sectional view of another embodiment of an eartip.

FIG. 52 illustrates a cross section of a multi-size eartip 300 or earplug 300. Internal projections $600_1$, (here shown as $600_1$ and $600_2$), which can be ridge shaped, can contact and seal various regions upon deformation of bulbous regions $340_{1-2}$. Internal projections $600_{1-n}$ can extend downward from bulbous regions $340_{1-n}$. In the particular embodiment illustrated two bulbous regions $340_1$ and $340_2$ are designed to accommodate two sizes as shown with the arrows, respectively.

Figure 53:
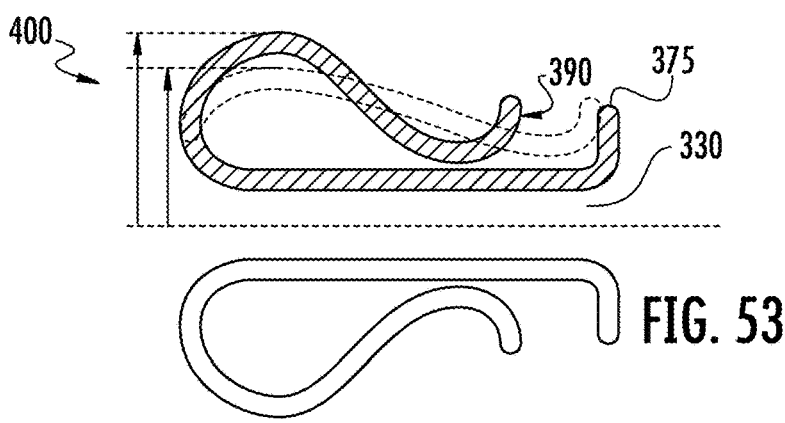
FIG. 53 illustrates another embodiment of an eartip.

FIG. 53 illustrates a variable size eartip 300 where the size is continuously adjustable as inserted as shown in example size (s1) and example size (s2). As the eartip 300 is inserted into an orifice such as an ear canal, the internal size of the orifice will press and deform the original outside diameter eartip 300, sliding the sealing section 390 towards lip or back ridge 375, changing the eartip 300 size to accommodate the size of the orifice as shown with the difference between the arrows on the left and the outline in dotted lines. Still further, since the materials are designed to slide, variable sizes can be accommodated. There is a tendency or bias for the system to return to its original shape so that if the eartip passes through a smaller region of an orifice it will re-expand to fit a larger size of the orifice.

Figure 54:
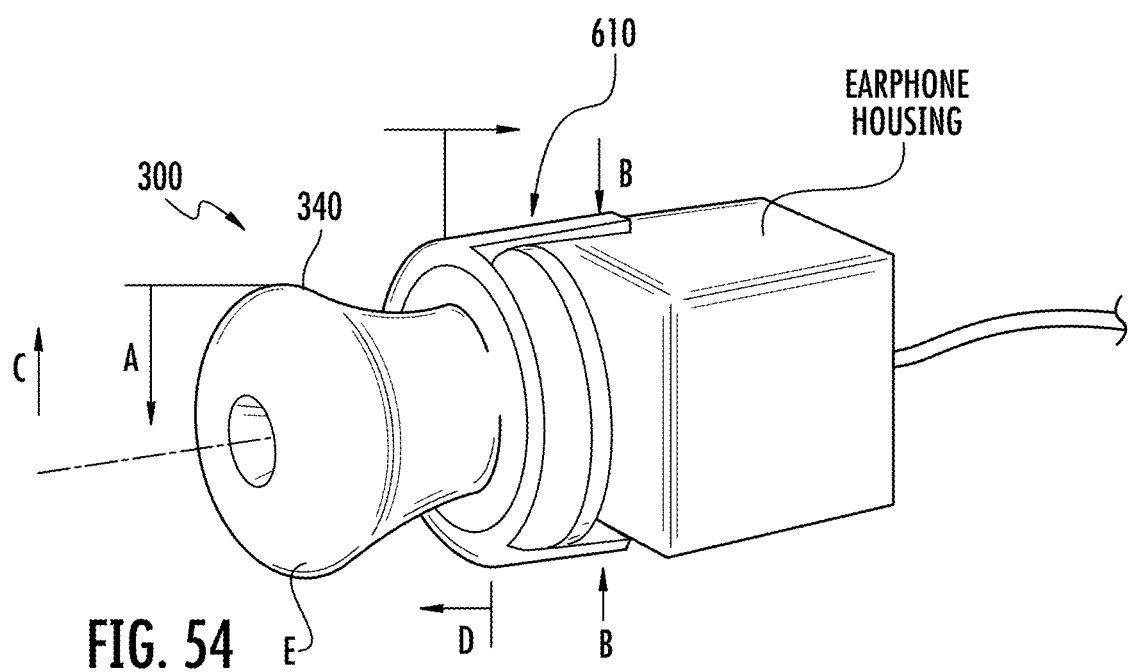
FIG. 54 illustrates another embodiment of an eartip coupled to a housing.

FIG. 54 illustrates another embodiment of a variable size eartip 300 coupled to a device housing. The eartip 300 including an adapter 610, which can be an insertion assist tab or an insertion sleeve. The adapter 610 can be used (e.g., pulled) to deform the eartip 300 for insertion. Such pulling can change the eartip size as shown with arrows A and C, and arrow D indicating a recoil upon release to expand so that the eartip outer surface E expands to contact the orifice wall (e.g., ear canal wall). In operation, a user can press as indicated by arrows B to hold the adapter 610 during insertion of eartip 300 into an ear canal. Once inserted, the adapter 610 can be released by the user resulting in the bulbous region 340 of eartip 300 expanding until it contacts the ear canal wall.

Figure 55:
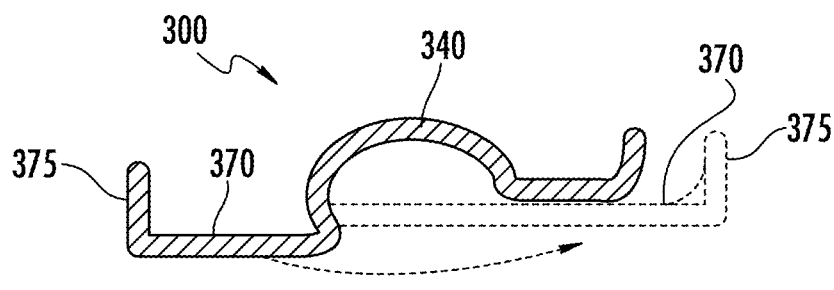
FIG. 55 illustrates a cross section view of an another embodiment of eartip.

FIG. 55 illustrates a cross section view of an another embodiment of eartip 300 where the channel wall 370 and lip or back ridge 375 is molded inverted, while the bulbous region 340 is molded for use without inversion.

Figure 56A:
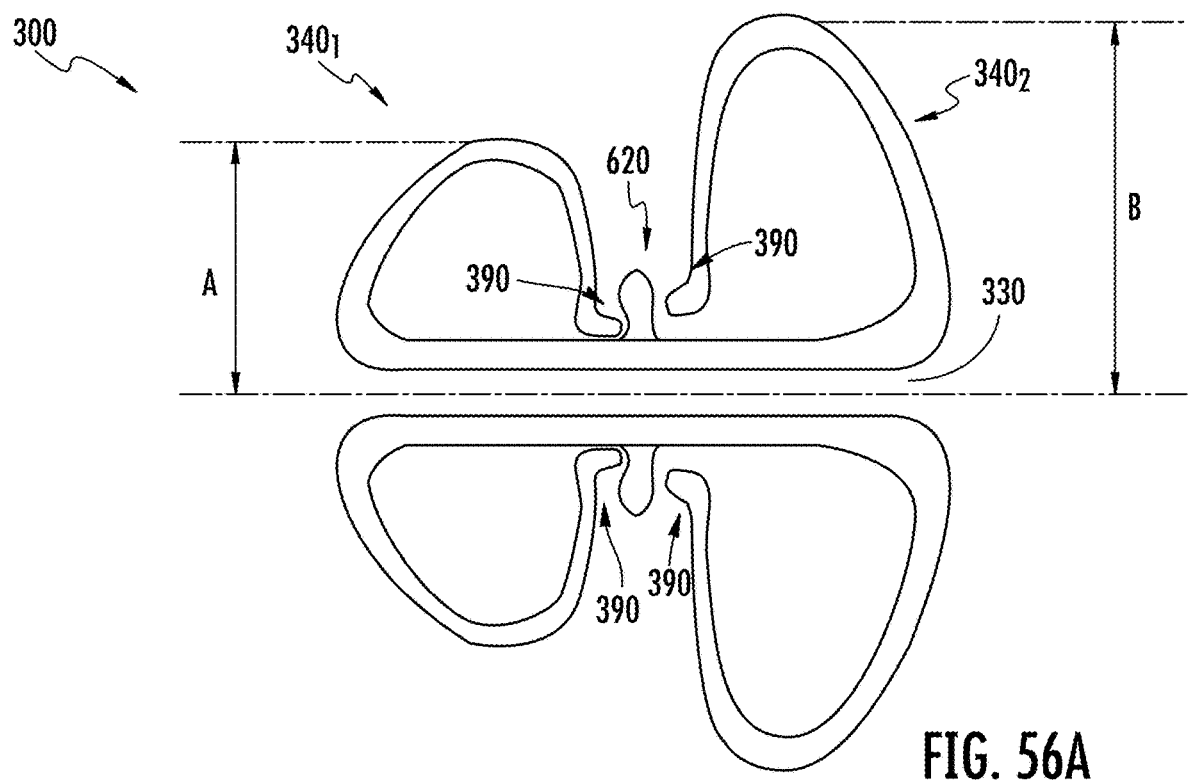
FIG. 56A illustrates a cross sectional view of another embodiment of an eartip.
Figure 56B:
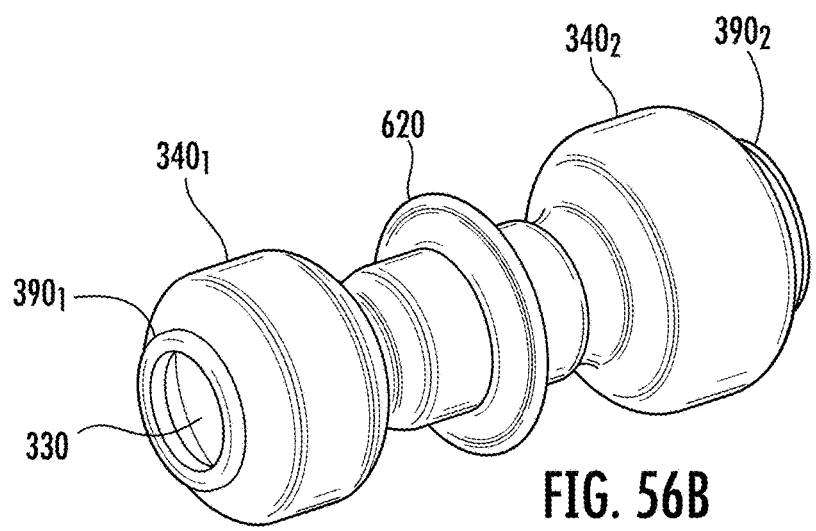
FIG. 56B illustrates a perspective view of the embodiment of FIG. 56A.

FIG. 56A illustrates a dual size (A and B), single ledge 620 rotatable size eartip 300. For the various sizes, the bulbous regions 340$_1$ and 340$_2$, which here form a toroid with a protruding ridge, of molded eartip 300 are folded to contact the single ledge 620. Depending upon the size desired, the eartip 300 is rotated. In some designs, it is possible to get four sizes by unfolding one of the sides, so that the one sealing section 390$_1$,390$_2$ can be adjusted to two sizes, one by contacting the ledge 620 or and the other by contacting the back of the other membrane of the bulbous region 340 or sealing section 390$_1$,390$_2$. For the final third and fourth size, the eartip 300 is rotated and the previous folded membrane of bulbous region 340$_1$, for example, is unfolded and the previous unfolded membrane of bulbous region 340$_2$, for example, is folded to two positions. Such varied arrangements provide a total of four sizes. FIG. 56B illustrates a perspective view of the eartip of 56A.

FIGS. 57-60A and 60B illustrate an occlusion effect eartip 300, that can have a port 630 open on the ear canal side and which allows passage under the eartip outer bulb and out near an ambient side of the eartip 300. The eartip 300 can also include an ear canal channel 640 that channels sound and/or air. Still further, the eartip 300 can also include an ear canal opening 635, an ambient side opening 650 and an ambient ledge 660 that maintains the ambient side opening 650 in an open state.

Note that the durometer of the eartips can vary between 2 Shore A to 90 Shore A. Typical dimensions of the thickness of the membrane ending in the sealing section 390 and lip or back ridge 375 can be between approximately 0.001 mm to approximately 2 or more mm. The length (along the long axis) of an eartip 300 can be from approximately 4 mm to approximately 25 mm or more depending upon the final usage. The outer diameter of contact portions of the eartip, such as sealing section 90, can vary from approximately 3 mm to approximately 50 or more mm, typically approximately 8 mm to approximately 18 mm. Note also that the thickness of the membrane of the body 310 can be varied along the longitudinal length. For example the portion anticipated to contact the ear canal can be thinner, while the end of the membrane near the tip can be thicker to maintain restoring pressure.

The outer portion of an Eartip (e.g. a ridge) contacts the ear canal wall when inserted into the ear canal. The inner portion contains a core that can fit on a stent (earphone eartip), while a wider portion aids in insertion onto a stent, or if used as an earplug the core will be filled in. Prior to insertion into an ear canal the outer portion and inner portion encapsulate (Eartip membrane contacts a structure (e.g., stent part, ledge-movable or part of stent), when inserted or as presented (final form after folded from a negative mold)) a medium (e.g., gas, fluid) that can have an opening aiding molding. Note that the opening can be faced inward toward the ear canal or formed to face toward the ambient environment. Note that the stent can be fabricated from various materials (e.g., silicon, urethane, rubber) and can include internal channel (tubes). The stent can also be a multi-lumen (i.e., multi-passageway) stent where the channels/tubes are various lumens of the multi-lumen stent, or solid (e.g., earplug stent). Note that the material of the membrane can have different properties from eth stent. Upon insertion into an ear canal the ear canal wall pressure on the outer portion of a ridge and the outer portion can move radially and axially to relieve the pressure pressing against the ear canal wall. This is in contrast to foam tips that will always press back radially dependent upon the amount of deformation of the foam. The combination of radial and axial movement of the outer section helps decrease pressure on the ear canal wall and increase contact area also decreasing pressure for a given retaining force.

The lip can be designed to facilitate sliding, and the surface can be low friction as well (e.g., permeated with mineral oil).

Additionally although description herein may refer to eartip as referring to a eartip version that can be fitted upon an earphone housing, the discussion should also be interpreted as also referring to an earplug version where any central core is filled to act as an earplug or the central core is fitted with designed channels to suppress specific acoustic bands.

Earphone Devices

Figure 61:
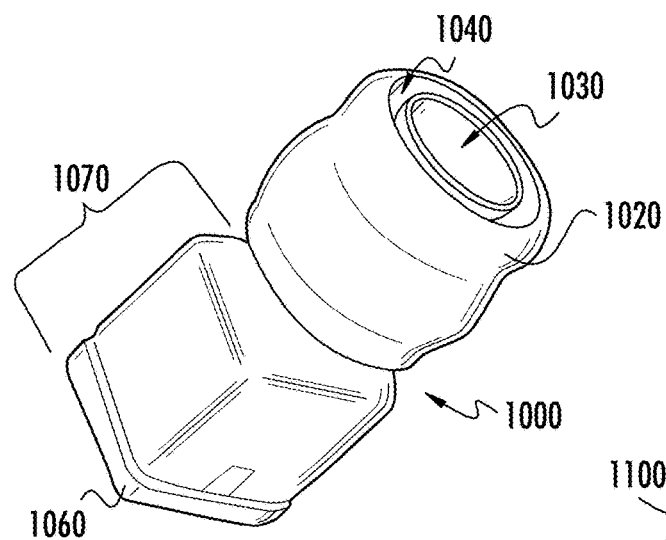
FIG. 61 illustrates an angled view of an earphone device including an eartip according to an embodiment of the present disclosure.

FIG. 61 illustrates an earphone device 1000 (also referred to as a HearBud earphone in the present disclosure), including an eartip 1020 (e.g., an Eartip), an earphone housing (EH) 1070 and cap 1060 which form the hearbud housing device (HH) 1100. The eartip 1020 illustrated in FIG. 60z may be configured and/or designed to include an acoustic opening 1030 to allow acoustic energy to enter and leave acoustic channels connected to electrical components (e.g., microphones, transceivers, processors, memories, and speakers) in the electronics package (EP) 1090 that sit within the electronic package housing 1050 that is connected to the stents and acoustic channels of the HH 1100. The electronics package 1090 may be configured to include, but is not limited to including, a processor, a memory, a transceiver, an ear canal microphone, an ambient sound microphone, any integrated circuits, a RFID chip, a NFC chip, a short-range wireless protocol and/or long-range wireless protocol chip, any other desired electronics, or any combination thereof. As shown in FIG. 60z, a space 1040 may exist between a portion of the eartip 1020 that forms the acoustic opening 1030 and the body of the eartip 1020.

Figure 62:
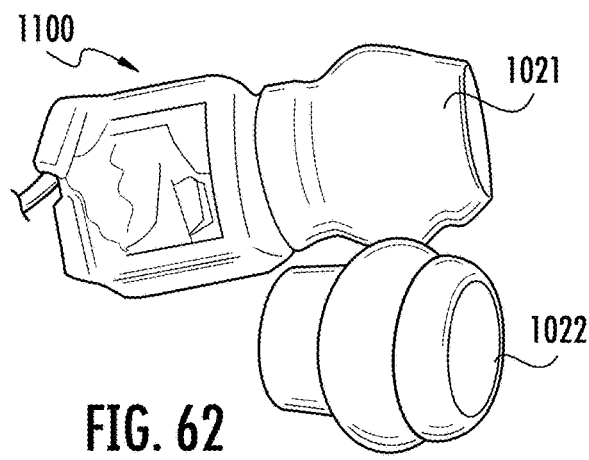
FIG. 62 illustrates a side view illustrating a comparison of different types of eartips that may be utilized with an earphone device according to an embodiment of the present disclosure.

FIG. 62 illustrates a comparison between different types of eartips provided in the present disclosure. In particular, FIG. 61z illustrates a molded eartip 1021 and a 3D-printed eartip 1022, which are configured to fit upon a hearbud housing device 1100 of the earphone device 1000. In certain embodiments, the molded Eartip 410 can be formed of various flexible materials including, but not limited to, silicone, rubber (including high strength rubber, urethane, synthetic rubber, nitrile rubber, chloroprene rubber, EVA rubber, Quartz fibre, any other suitable material, or a combination thereof.

Figure 63:
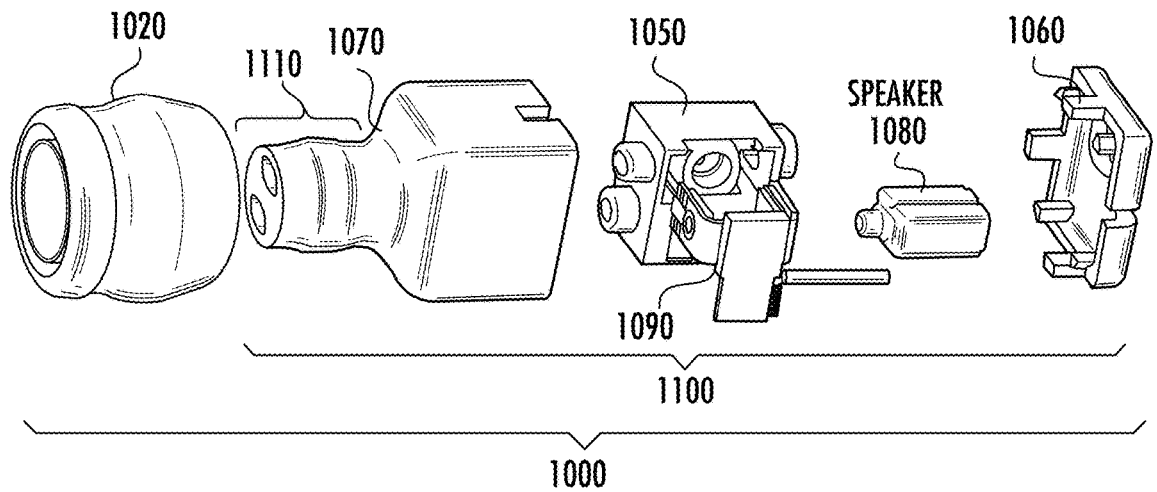
FIG. 63 is an exploded view of an earphone device illustrating various components of the earphone device according to an embodiment of the present disclosure.

FIG. 63 illustrates an exploded view of an earphone device 1000 (which can include or not include an eartip 1020) showing the components of the earphone device 1000. The components of the earphone device 1000 includes a earphone housing 1070 including a stent 1110, a cap 1060, electronics package housing 1050, an EP 1090, and an eartip 1020. In certain embodiments, the EP 1090 may include a flexible circuit, to which ambient sound microphones, ear canal microphones, ear canal receivers (e.g. speaker 1080), processors, and/or memories may be affixed. Note that the stent can be fabricated from various materials (e.g., silicon, urethane, rubber) and can include internal channel (tubes). The stent can also be a multi-lumen (i.e., multi-passageway) stent where the channels/tubes are various lumens of the multi-lumen stent.

FIG. 64 illustrates an earphone device 1000 using a foam tip 1023 that fits upon the stent 1110 of the hearbud housing device 1100. In certain embodiments, the foam tip 1023 can be any conventional foam tip, for example Comply Comfort Tips.

FIG. 65 illustrates a earphone device 1000 using an eartip 1020 that is configured to fit on a stent 1110 on the hearbud housing device 1100.

FIG. 66 illustrates an additional exploded view of a hearbud housing device 1100 with various components labelled and which are configured to be housed within the hearbud housing device 1100. For example, in certain embodiments, the components of the earphone device 1000 can include the hearbud housing device 1100, an earphone housing 1070, a cap 1060, and an electronic package housing 1050, which houses the electronics package (EP) 1090 that can include a speaker (SPKR or ECR) 1080, ambient sound microphone (ASM) 1120, an ear canal microphone (ECM) 1130, and supporting electronics that may form a part of the EP 1090. Note that any microphone that can be used in an earphone can be used for the ASM 1120 and ECM 1130. Additionally, any speaker that can be used in earphones can be used for the SPKR 1080 in the earphone device 1000.

Figure 67:
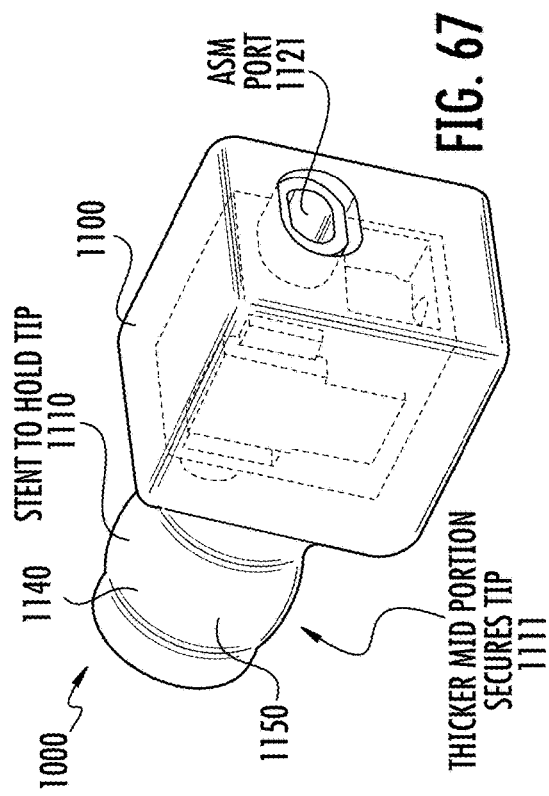
FIG. 67 illustrates a rear angled view of an earphone device including a stent and an ambient sound microphone port according to an embodiment of the present disclosure.

FIG. 67 illustrates a back of an earphone device 1000 without an eartip 1020. The hearbud housing device 1100 of the earphone device 1000 can include acoustic channels 1140 and 1150 that can be connected to components of the EPH 1070, which fits inside the earphone housing 1070 of the hearbud housing device 1100 using a keyed recess 1160, for example the SPKR 1080 and ECM 1130. The cap 1060 can include a port 1121 (e.g. an ASM port) to allow sound from the ambient environment to reach the ASM 1120. The stent 1110 of the hearbud housing device 1100 can be designed to help retain any tip inserted thereupon, for example, the stent 1110 can include a smaller end 1112 (e.g. 5.5 mm diameter) to allow ease of insertion of a tip onto the stent 1110, and a thicker mid stent diameter 1111 (e.g., 6.1 mm diameter) to facilitate a tight fit after tip insertion.

Figure 68:
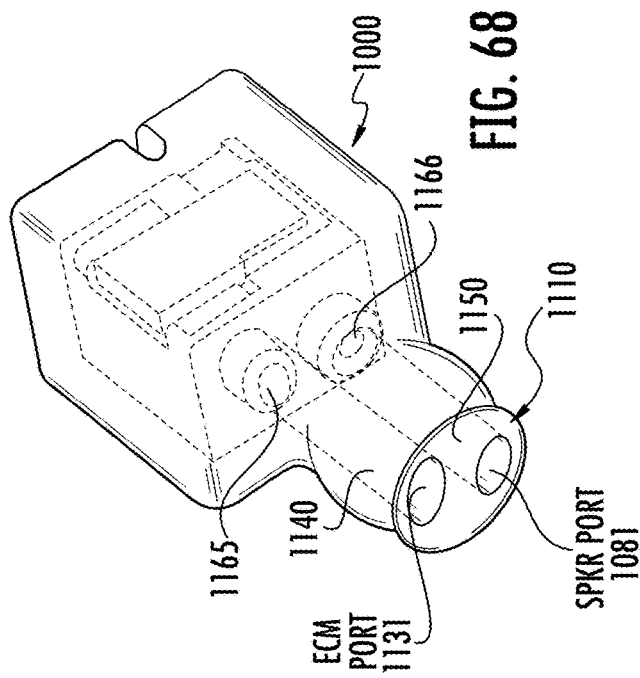
FIG. 68 illustrates a front view of an earphone device that includes an ear canal microphone port and a speaker port according to an embodiment of the present disclosure.

FIG. 68 illustrates a front view of an earphone device 1000, without an eartip 1020 that illustrates an acoustic channel 1140 to an ECM 1130 connected at a port 1165, an acoustic channel 1150 to a SPKR 1080 connected at a port 1166. The acoustic channel 1150 can run from the SPKR 1080 at the connection to the port 1166 to a SPKR port 1081. The acoustic channel 1140 can run from the ECM 1130 at the connection to the port 1165 to the ECM port 1131.

Figure 69:
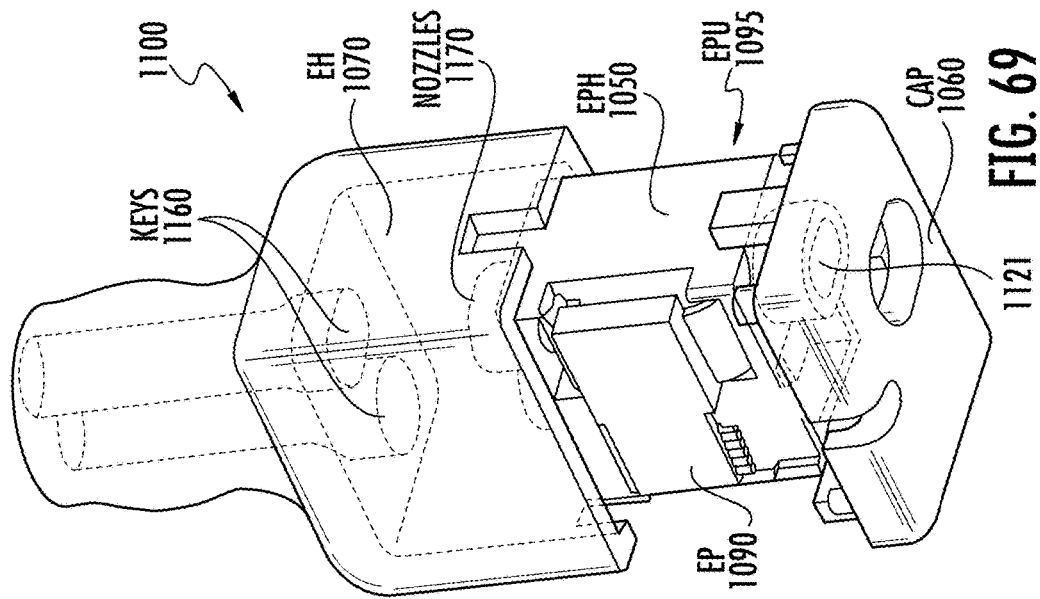
FIG. 69 is an exploded view of an earphone device that illustrates how the various components of the earphone device and hearbud housing device secure together according to an embodiment of the present disclosure.

FIG. 69 illustrates how parts fit within a earphone housing 1070 of hearbud housing device 1100 of an earphone device 1000. A set of keys 1160 (e.g., recessed or raise keys) in the earphone housing 1070 allow the earphone housing 1070 to connect with nozzles 1170 of the EPH 1050. Thus, the electronics packaging unit (EPU) 1095 can be standardized while the earphone housing 1070 design can be varied provided the keys 1160 of the earphone housing 1070 remain the same. The EPU 1095 may include the EPH 1050 that contains the EP 1090. The ASM port/nozzle 1121 connects the ambient environment to an ASM 1120 in the EPU 1095. A cap 1060 may fit over the back of the earphone housing 1070 and the back of the EPU 1095 when inserted into the earphone housing 1070 of the hearbud housing device 1100 of the earphone device 1000.

Figure 70:
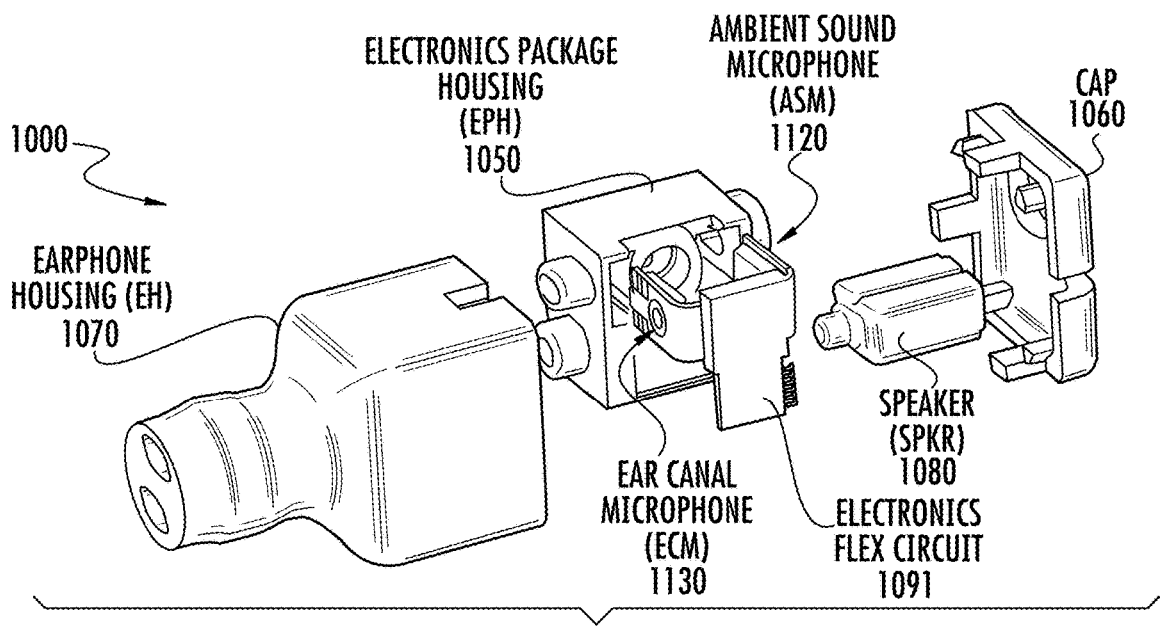
FIG. 70 is an angled exploded view of an earphone device illustrating how various parts of the earphone device secure together according to an embodiment of the present disclosure.

FIG. 70 illustrates various parts that fit within a earphone housing 1070 of a hearbud housing device 1100 that form an earphone device 1000. The parts that fit within the earphone housing 1070 can include an ASM 1120, an ECM 1130, an EPH 1050, a flexible circuit 1091 of an EP 1090, the EP 1090 itself, a SPKR 1080, and a cap 1060.

Figure 71:
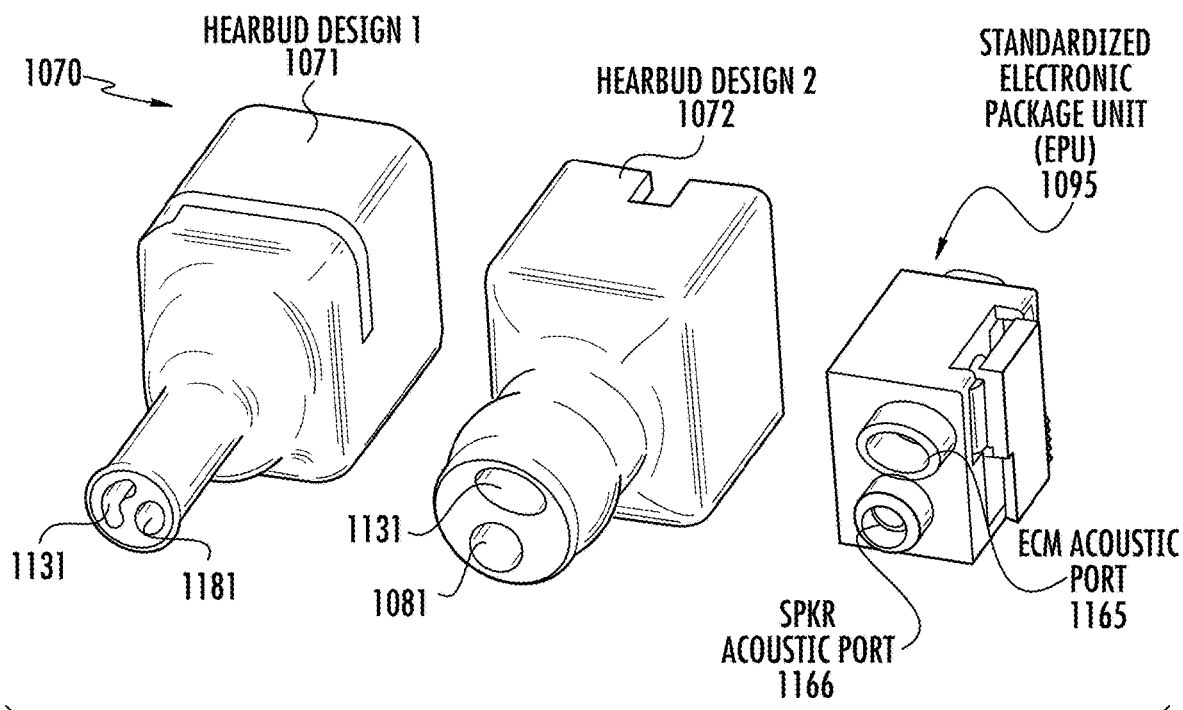
FIG. 71 illustrates various earphone housing designs and an electronic package unit design that may be utilized with an earphone device according to embodiments of the present disclosure.
Figure 72:
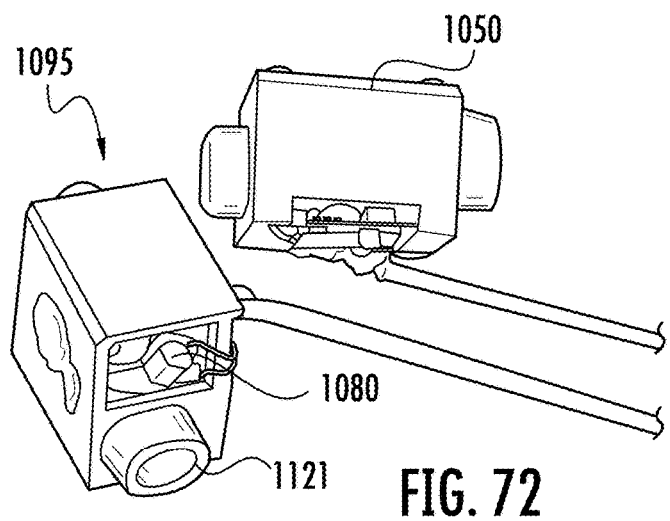
FIG. 72 illustrates an angled rear view of an electronics packaging unit and a side view of an of an electronics package housing of an earphone device according to an embodiment of the present disclosure.
Figure 73:
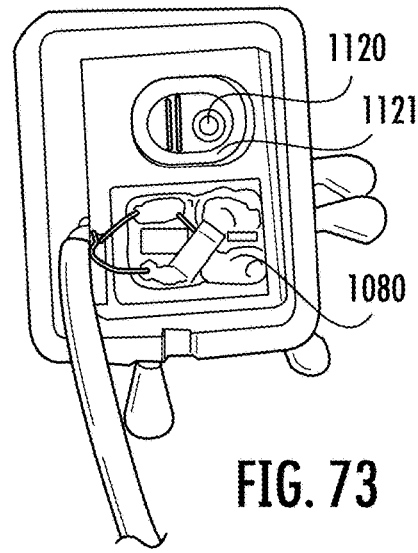
FIG. 73 illustrates a rear view of an electronics packaging unit of an earphone device according to an embodiment of the present disclosure.
Figure 74:
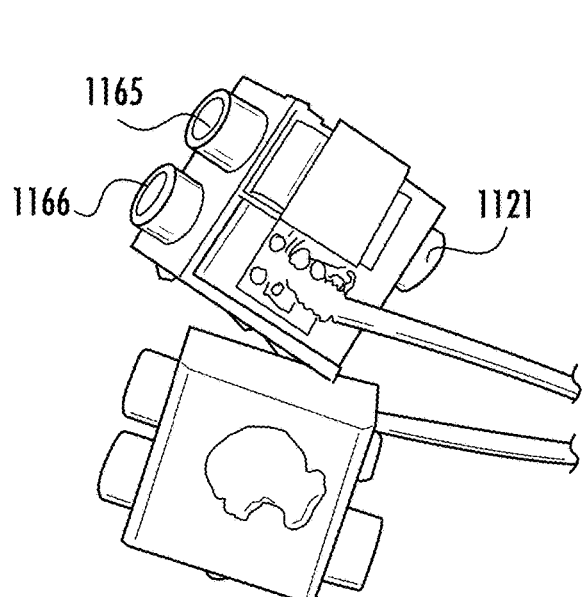
FIG. 74 illustrates various views of an electronics packaging unit of an earphone device according to an embodiment of the present disclosure.
Figure 75:
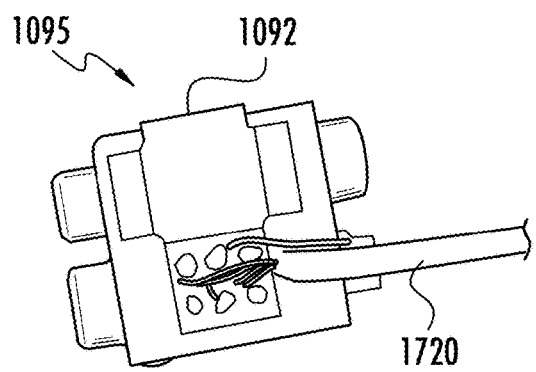
FIG. 75 illustrates an additional view of an electronics packaging unit of an earphone device according to an embodiment of the present disclosure.

FIG. 71 illustrates the various earphone housing designs 1071, 1072 and that can be used with a standardized electronics packaging unit 1095. The keyed regions within 1071 and 1072 fit the EPU ports for the ECM 1130 and SPKR 1080 as discussed above. Additionally, FIG. 70z illustrates various cross-sectional shapes and areas of the ECM and SPKR ports 1131 and 1081, whose cross sectional areas depend upon acoustic needs. For example, in order to avoid clipping in digital microphones, the largest ECM ports 1131 possible are needed, for example, which are greater than 1 mm^2.

FIGS. 72, 73, 74, and 75 illustrates various views of the EPU 1095 and various components that fit within the EPU 1095. The EPU 1095 includes a EPH 1050, SPKR 1080 with associated port/nozzles 1161, an ASM 1120 with associated ports/nozzles 1121, an ECM 1130 with associated ECM port/nozzle 1165, supporting electronics 1092, with optional wire 1171. Notably, the EPU 1095 can contain a wireless chip and battery negating the need for a wire 1171.

FIG. 76 illustrates a comparison between a typical design dependent component layout 1800 with a standardized EPU design 1095. The advantage of standardizing the form factor of the EPU 1095 is that once optimized multiple earphone housing 1070 designs can be formed that fit the same EPU 1095. In certain embodiments, the form-specific component layout 1800 would have to be changed every time the earphone housing 1070 is changed.

FIG. 77 illustrates the front of an EPU 1095. FIG. 78 illustrates a comparison of a typical earphone device 1000 with specific component orientation based upon design and three various earphone housing designs 2010, 2020, 2030 using one EPU 1095 design. As can be seen, various earphone housings 1070 can be varied to fit the same EPU 1095.

Figure 79:
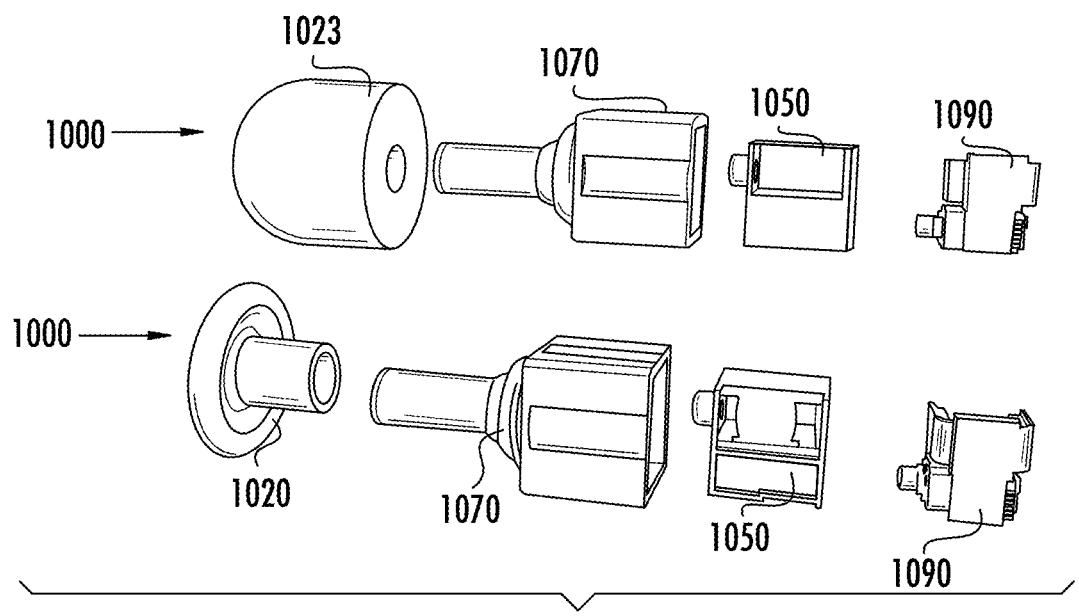
FIG. 79 illustrates a comparison of components of earphone devices with a foam tips and eartips according to an embodiment of the present disclosure.

FIG. 79 illustrates a comparison of the components of earphone devices 1000 with foam tip 1023 and eartip 1020 variants, including earphone housings 1070, electronics package housings 1050, and EPs 1090.

Figure 80:
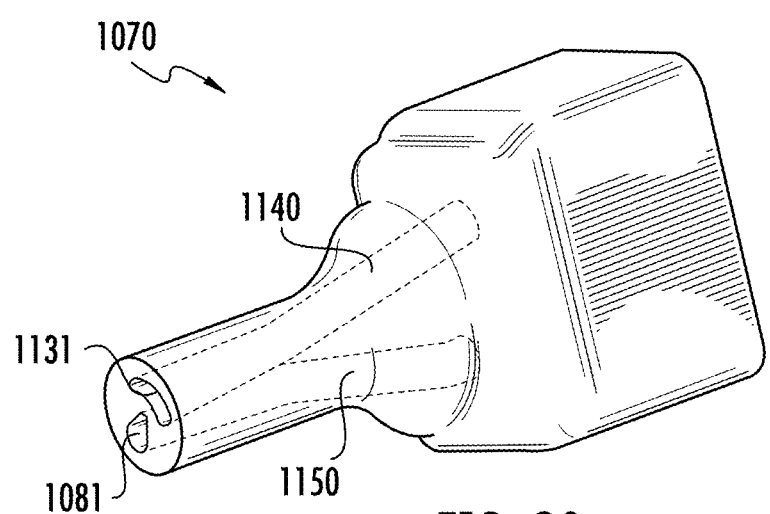
FIG. 80 illustrates a front view of an earphone housing for use with an earphone device according to an embodiment of the present disclosure.

FIG. 80 illustrates a front of a earphone housing 1070 showing various acoustic channels 1140, 1150, porting acoustic energy to and from components, exiting in ports 1131 and 1081.

Figure 81:
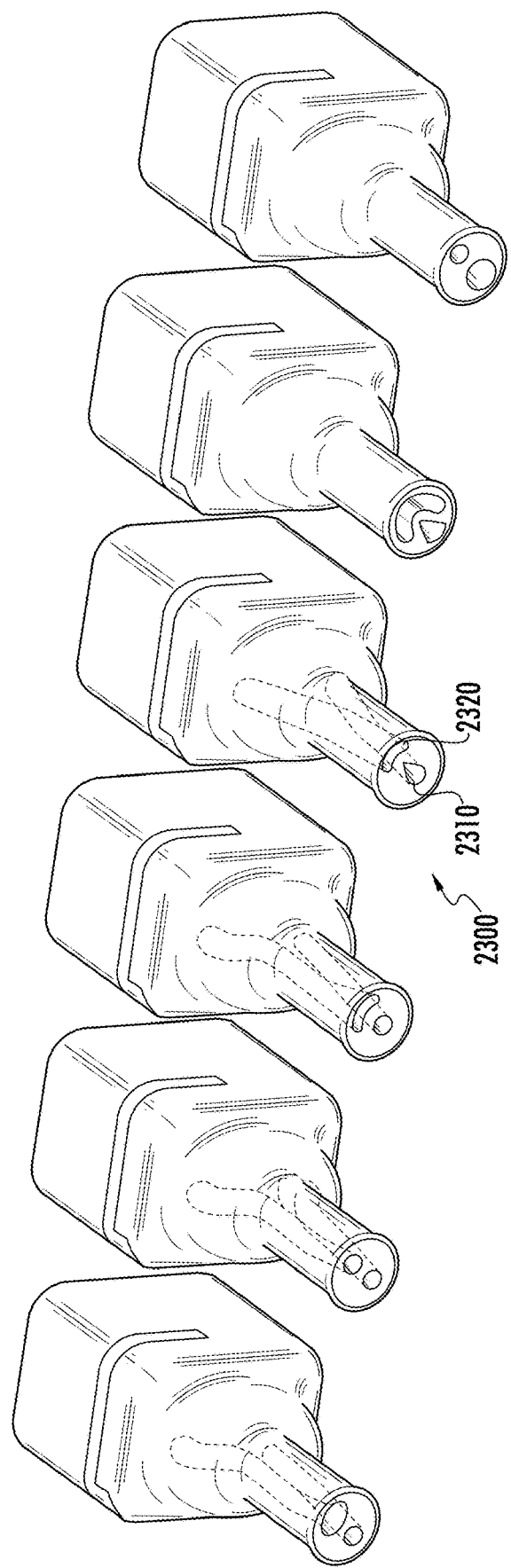
FIG. 81 illustrates various acoustic channel shapes for use with earphone housings of an earphone device according to embodiments of the present disclosure.

FIG. 81 illustrates various acoustic channel shapes 2310 and 2320 associated with similar earphone housings 1070. Since the earphone housing 1070 can be molded or 3D printed, various acoustic channels can be formed, for example, many complicated channels can be formed from 3D printing that cannot be molded.

FIGS. 82-84 illustrate various earphone devices 1000 with different eartip designs, 3600, 3700 and 3800 for eartips 1020 attached to earphone housings 1070. Various shapes for the eartip 1020 can occur, for example, a dual chamber embodiment for the eartip 1020 is illustrated in FIG. 84, a single chamber embodiment is illustrated in FIG. 83, and a combination of a flange and single chamber embodiment of the eartip 1020 is illustrated in FIG. 82. FIG. 85 illustrates an earphone device 1000 using a conventional foam tip 1023.

Figure 86:
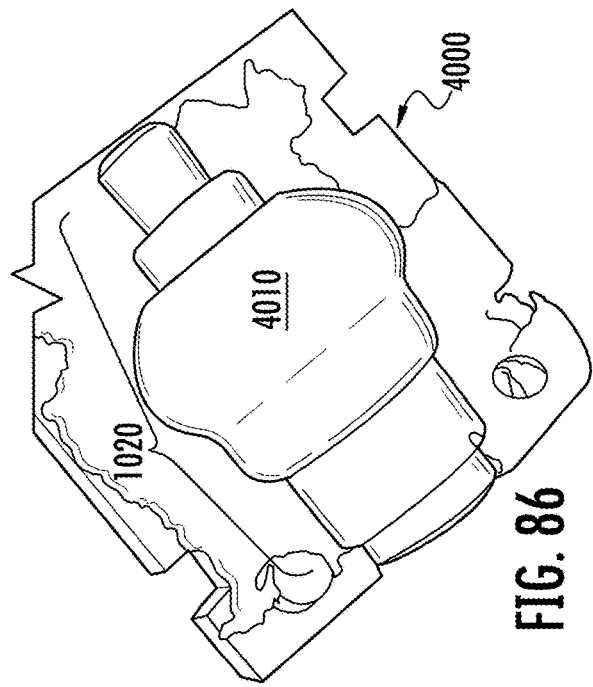
FIG. 86 illustrates a positive molding technique for an eartip where the final shape is molded directly according to an embodiment of the present disclosure.

FIG. 86 illustrates a positive molding technique for the eartip 1020 where the final shape is molded directly. The mold 4000 of the eartip 1020 includes a core pin and outer shell with a space between that is filled with flexible resin forming the eartip shape 4010, that is then removed, and cleaned (e.g., flash removed). Although the eartip 1020 shown in FIG. 86 may be molded using highly flexible rubber and a 3D printed mold, commercially such molds can be difficult due to undercuts.

Figure 87:
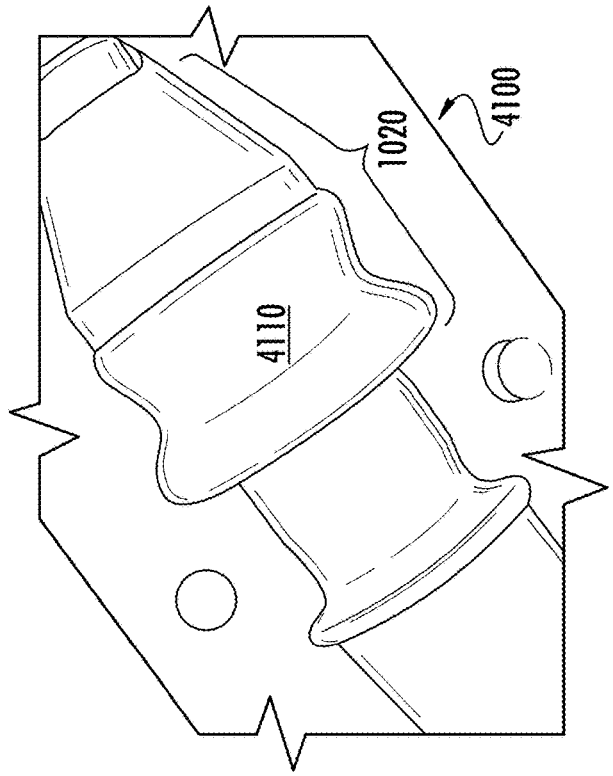
FIG. 87 illustrates a negative molding technique for an eartip where the final eartip shape is obtained after the molded shape is folded according to an embodiment of the present disclosure.
Figure 88:
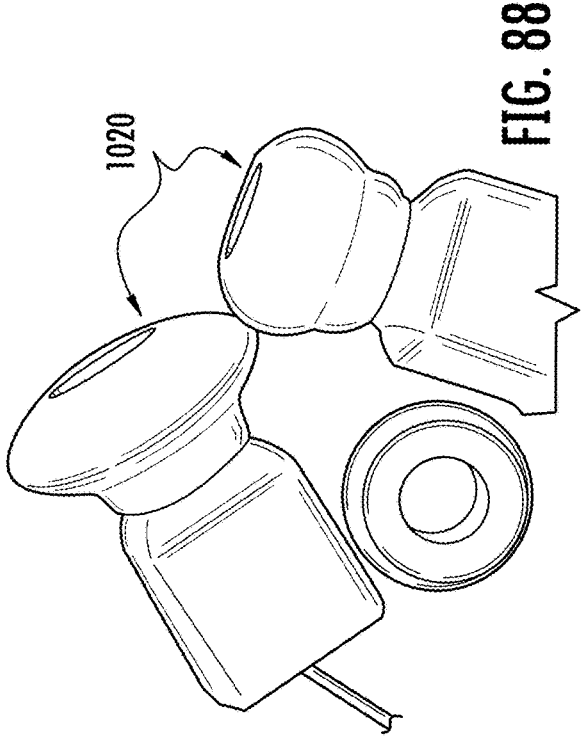
FIG. 88 illustrates a pair of molded eartips of different sizes according to embodiments of the present disclosure.

FIG. 87 illustrates a negative molding technique for the eartip 1020 where the final eartip shape is obtained after the molded shape is folded, facilitating moldability. The mold 4100 of the eartip 1020 can be 3D printed, as shown, or commercially molded since the undercuts may be substantially reduced as compared to the mold in FIG. 86. The inverted mold 4110 that is formed can be extracted and folded to form the eartips 1020, as shown in FIG. 88, which shows two molded eartips 1020 of different sizes.

Figure 89:
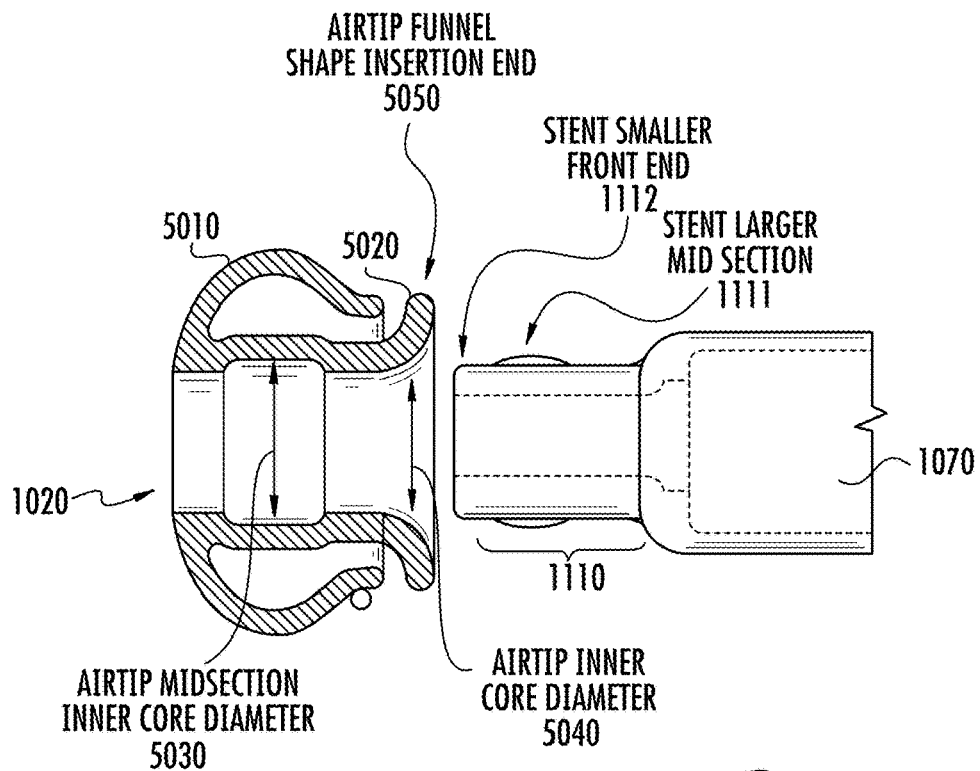
FIG. 89 illustrates the retention and ease of insertion features of an eartip for use with an earphone device according to an embodiment of the present disclosure.

FIG. 89 illustrates the retention and ease of insertion features of the eartip 1020. A funnel portion 5050 of the eartip 1020 is designed to aid insertion of the tip of a earphone housing's 1070 stent's 1110 smaller front end 1112. As the smaller end 1112 of the stent 1110 is inserted, the funnel 5050 is spread stretching the inner core diameter 5040, allowing further insertion. A larger midsection inner core diameter 5030 matches the stent's 1110 larger midsection 1111 allowing the stretched inner core to lock and be secure upon the stent 1110 minimizing slippage and axial movement of the inner portion upon insertion.

Figure 90:
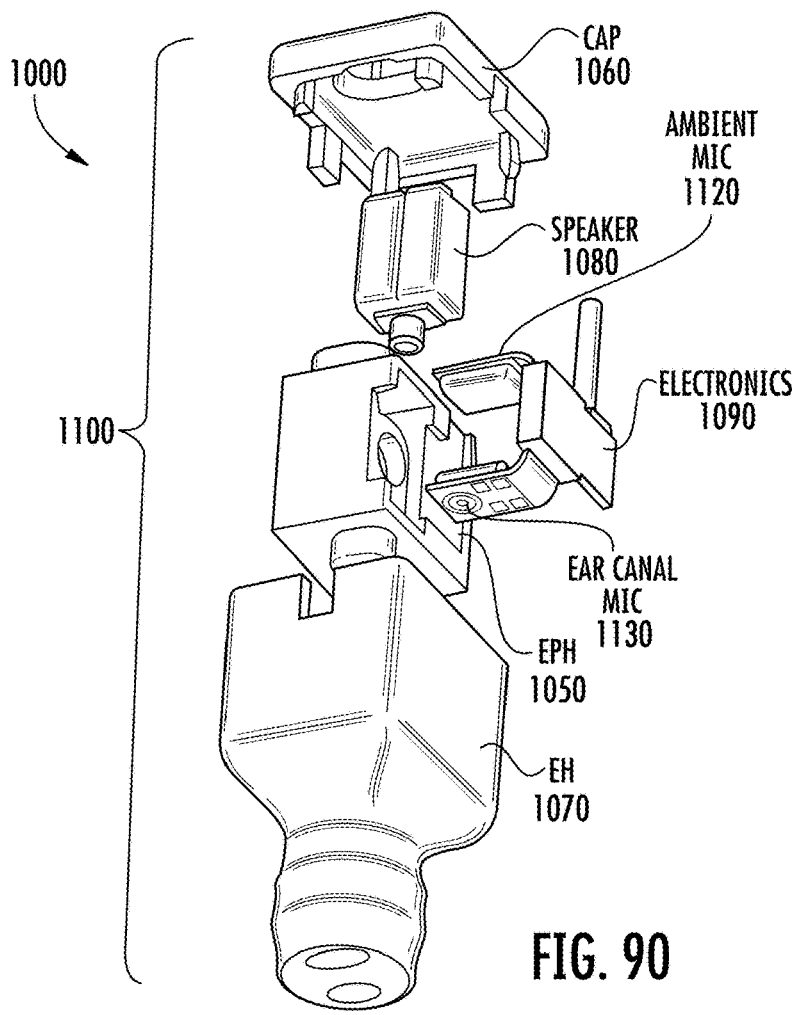
FIG. 90 is an exploded view of an earphone device according to an embodiment of the present disclosure.

FIG. 90 illustrates an exploded view of an earphone device 1000 including a hearbud housing device 1100, which houses various components of the earphone device 1000. As is described elsewhere in the present disclosure, the earphone device 1000 may include an earphone housing 1070 that includes keys 1160 (i.e. keyed recesses), which may connect with nozzles 1170 (which may correspond to ports 1165 and 1166) of an earphone package housing 1050 to secure the earphone housing 1070 to the earphone package housing 1050. The earphone package housing 1050 may house an electronics package 1090 that may include an ear canal microphone 1130 and/or an ambient sound microphone 1120. The electronics package 1090 may be inserted into the earphone package housing 1050 to form an electronics packaging unit. The earphone device 100 may also include a speaker 1080 and a cap 1060, which when placed on the bottom of the earphone device 1000 may be configured to seal the components of the earphone device 1000 together in a secure fashion.

Figure 91:
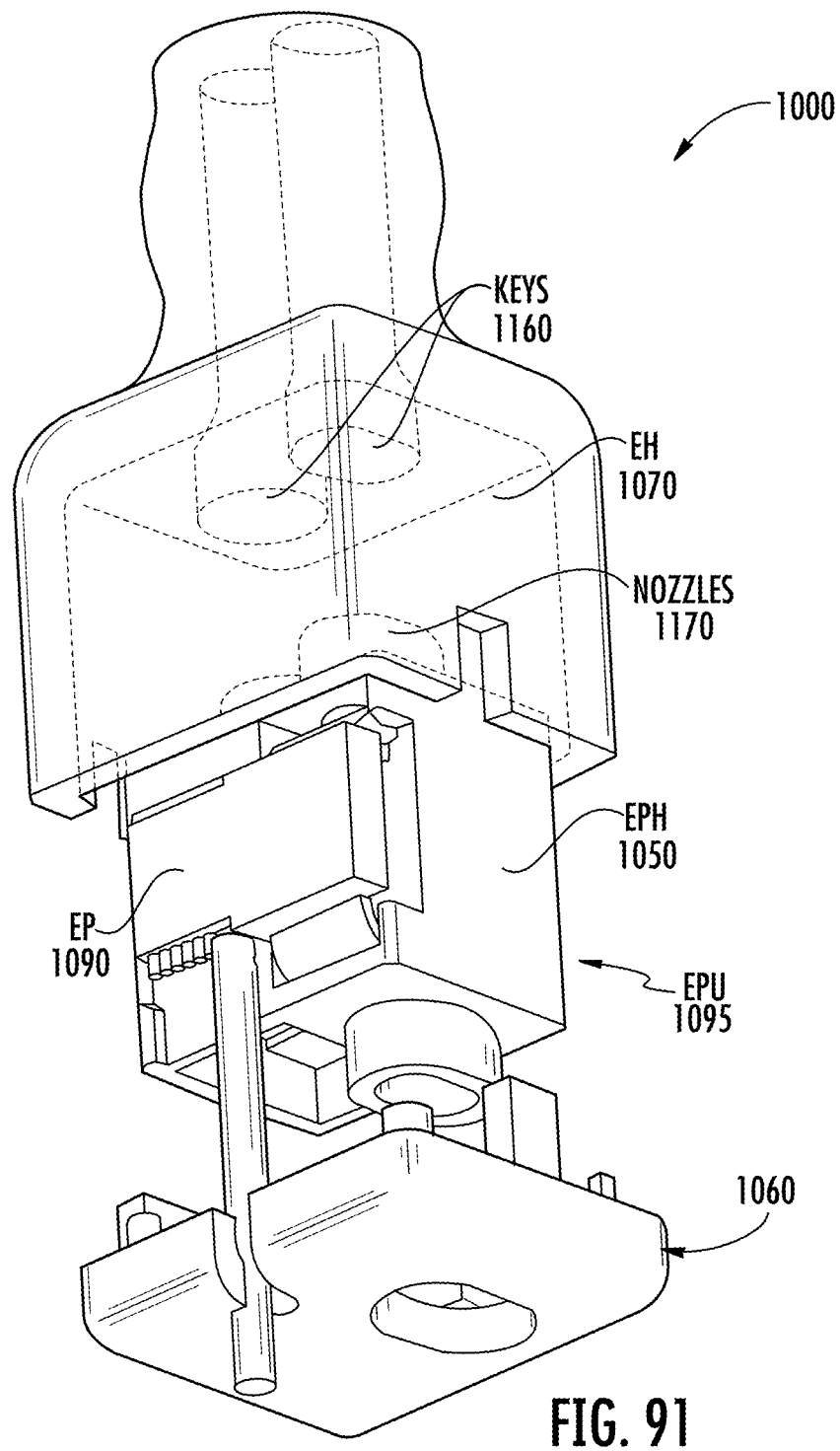
FIG. 91 is another exploded view of an earphone device according to an embodiment of the present disclosure.

FIG. 91 illustrates another exploded view of an earphone device 1000, which illustrates how the various components of the earphone device 1000 are secured to one another. As illustrated, earphone device 1000 may include an earphone housing 1070, which may include a pair of keys 1160 (i.e. keyed recesses), which may be configured form an interference fit with nozzles 1170 (which may correspond to ports 1165 and 1166) of the earphone package housing 1050. The electronics package 1090 may be inserted into the earphone package housing 1050 to form the electronics packaging unit 1095. The cap 1060 may be secured to the base of the electronics packaging unit 1095 to seal the components of the earphone device 1000 together.

Figure 92:
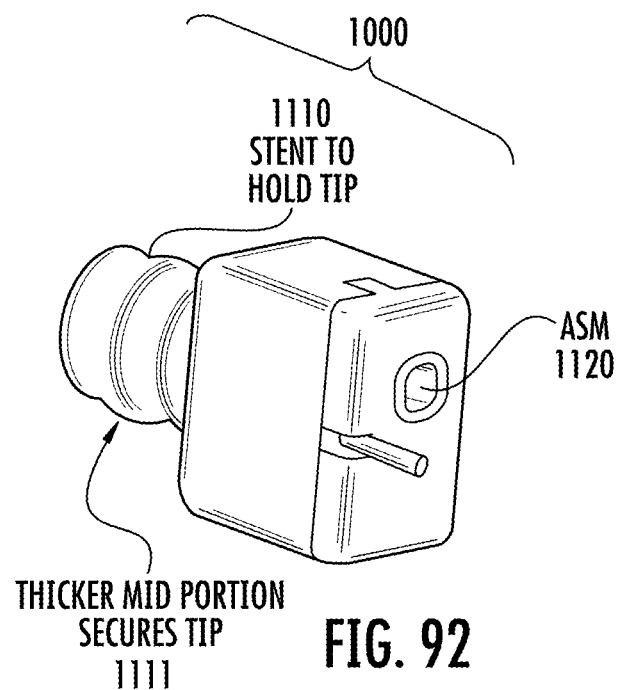
FIG. 92 is an angled back view of a portion of an earphone device according to an embodiment of the present disclosure.

FIG. 92 illustrates an angled back view of a portion of an earphone device 1000. The earphone device may include a stent 1110 that includes a ticker mid portion 1111, which may be utilized to secure an eartip 1020, a foam tip, a flange, any type of tip, or a combination thereof. The earphone device 1000 may further include an ambient sound microphone 1120 that may be configured to measure sounds occurring in an ambient environment in proximity to and/or surrounding the earphone device 1000.

Figure 93:
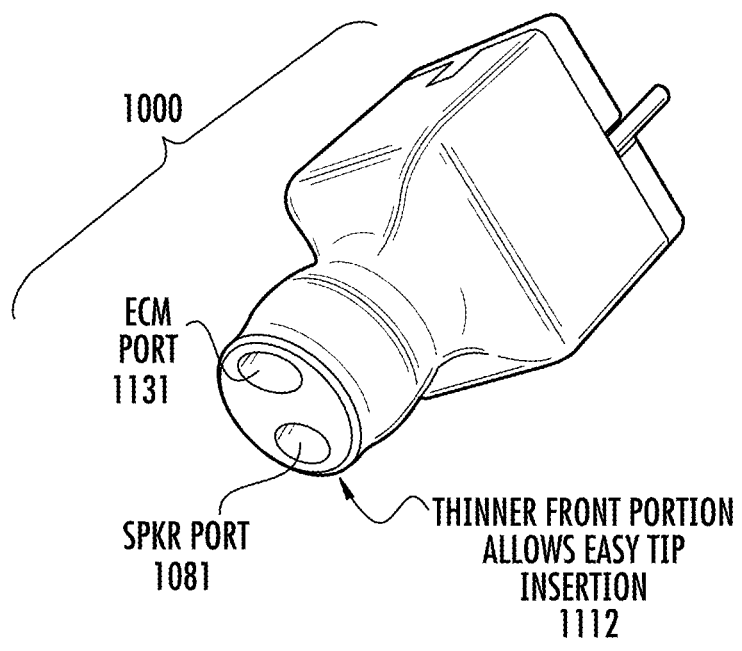
FIG. 93 is an angled front view of a portion of an earphone device according to an embodiment of the present disclosure.

FIG. 93 illustrates an angled front view of a portion of an earphone device 1000, which illustrates ports 1131, 1081 bored through a stent 1112 of the earphone device 1000. A first port may be an ECM port 1131, which may be a tunnel in the stent 1112 that connects to an ear canal microphone 1130 of the earphone device 1000. The ear canal microphone 1130 may be configured to measure sounds occurring within a user's ear canal when the earphone device 1000 resides in the user's ear canal. If the user's ear is occluded (i.e. sealed using a tip), the ear canal microphone 1130 can pick up sound leaking into the ear canal. For example, the ear canal microphone 1130 may pick up sound from the wearer's voice via bone conduction through the wearer's head. A second port may be a speaker port 1081, which may be a tunnel in the stent 1112 that connects to a speaker 1080 of the earphone device 1000. The speaker 1080 may deliver sound through the speaker port 1081 to the tympanic membrane at the end of the ear canal of a user's ear.

Figure 94:
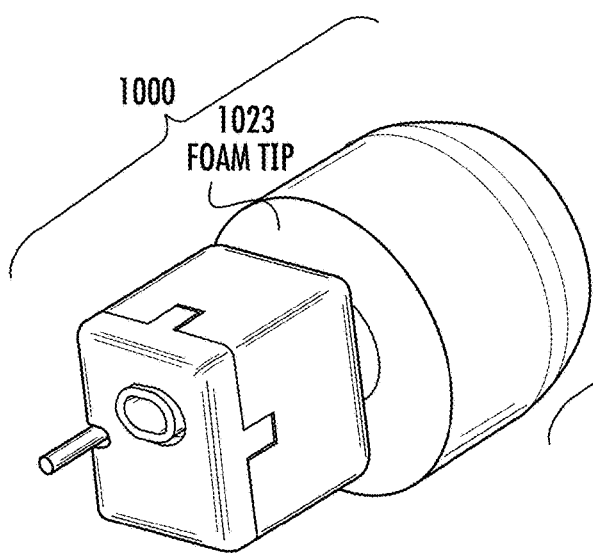
FIG. 94 is an angled back view of an earphone device including a traditional foam tip according to an embodiment of the present disclosure.
Figure 95:
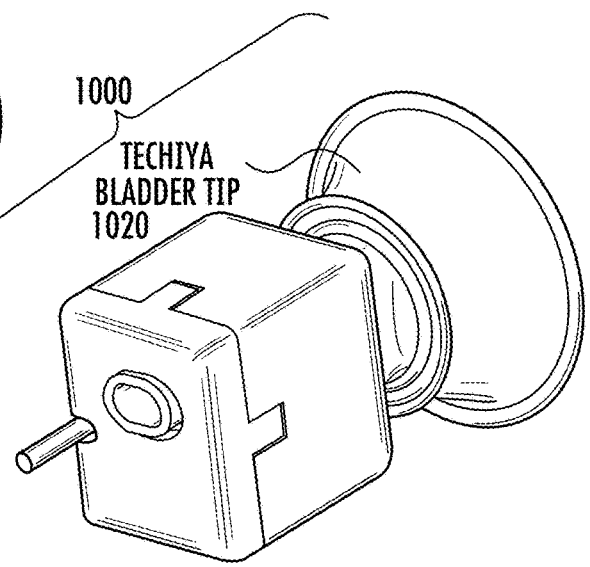
Figure 96:
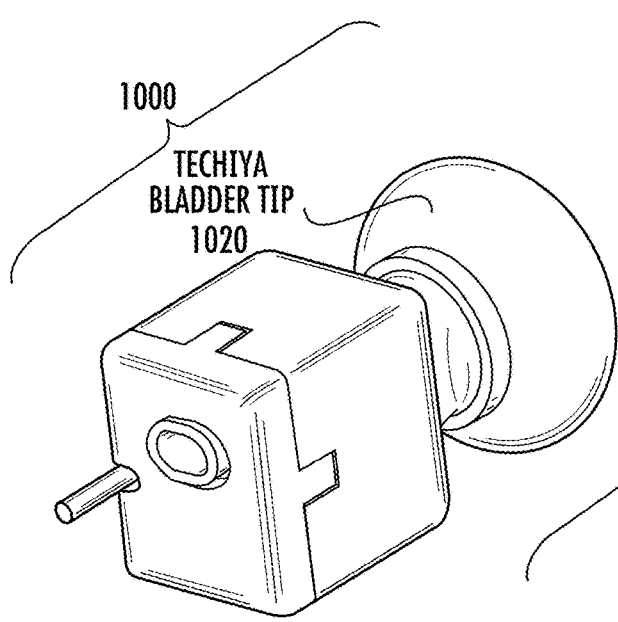
Figure 97:
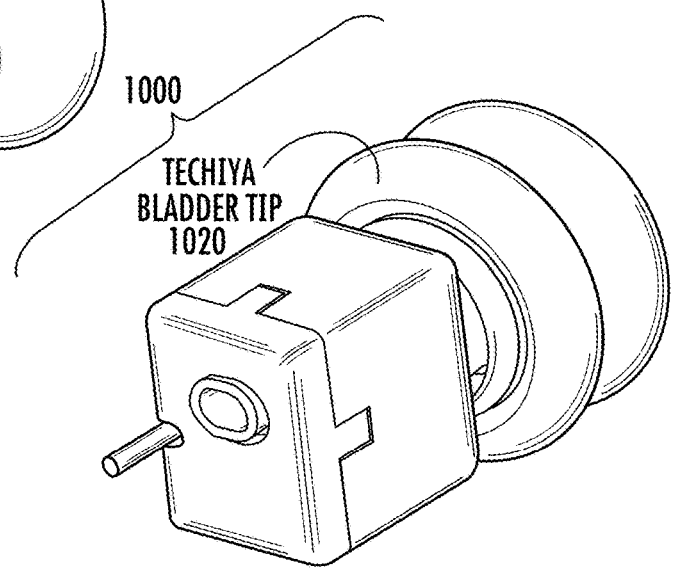

FIG. 94 illustrates an angled back view of an earphone device 1000 including a traditional foam tip 1023. In certain embodiments, instead of a foam tip 1023, the earphone device 1000 of FIG. 94 may utilize a flange tip as well. FIG. 95 illustrates an angled back view of an earphone device 1000 including an embodiment of an eartip 1020 that is designed to fit on the same stent 1110 as commercial foam and/or flange tips. FIG. 96 illustrates another angled back view of an earphone device 1000 including a different embodiment of an eartip 1020 that is also designed to fit on a stent 1110 and which includes a single chamber. FIG. 97 illustrates another angled back view of an earphone device 100 including a further embodiment of an eartip 1020 that includes dual chambers.

FIG. 98 illustrates an exploded view of an earphone device 1000. The earphone device 1000 of FIG. 98 may include an eartip 1020, which may be balloon/bladder tip, which may be position onto a stent 1110 of an earphone housing 1070. The earphone housing 1070 may connect with an electronic package housing 1050, which may house an electronic package 1090. The components of the earphone device 1000 may sealed and/or secured together using the cap 1060.

FIG. 99 illustrates a side exploded view of an earphone device 1000. The earphone device 1000 may include an eartip 1020, which may be secured onto an earphone housing 1070, such as via a stent of the earphone housing 1070. The earphone housing 1070 may house and connect to an electronic package 1090. The earphone device 1000 may also include a speaker for outputting sound into a user's ear. The earphone device 1000 may also include a cap 1060 to secure the components of the earphone device 1000 together.

FIG. 100 illustrates another side exploded view of an earphone device 1000. The earphone device 1000 may include an eartip 1020, which may be secured onto an earphone housing 1070, such as via a stent of the earphone housing 1070. The earphone housing 1070 may house and connect to an electronic package housing 1050, which may house an electronics package 1090 including an ear canal microphone and an ambient sound microphone. The earphone device 1000 may also include a speaker 1080 for outputting sound and a cap 1060 for securing the components of the earphone device 1000 together.

Figure 101:
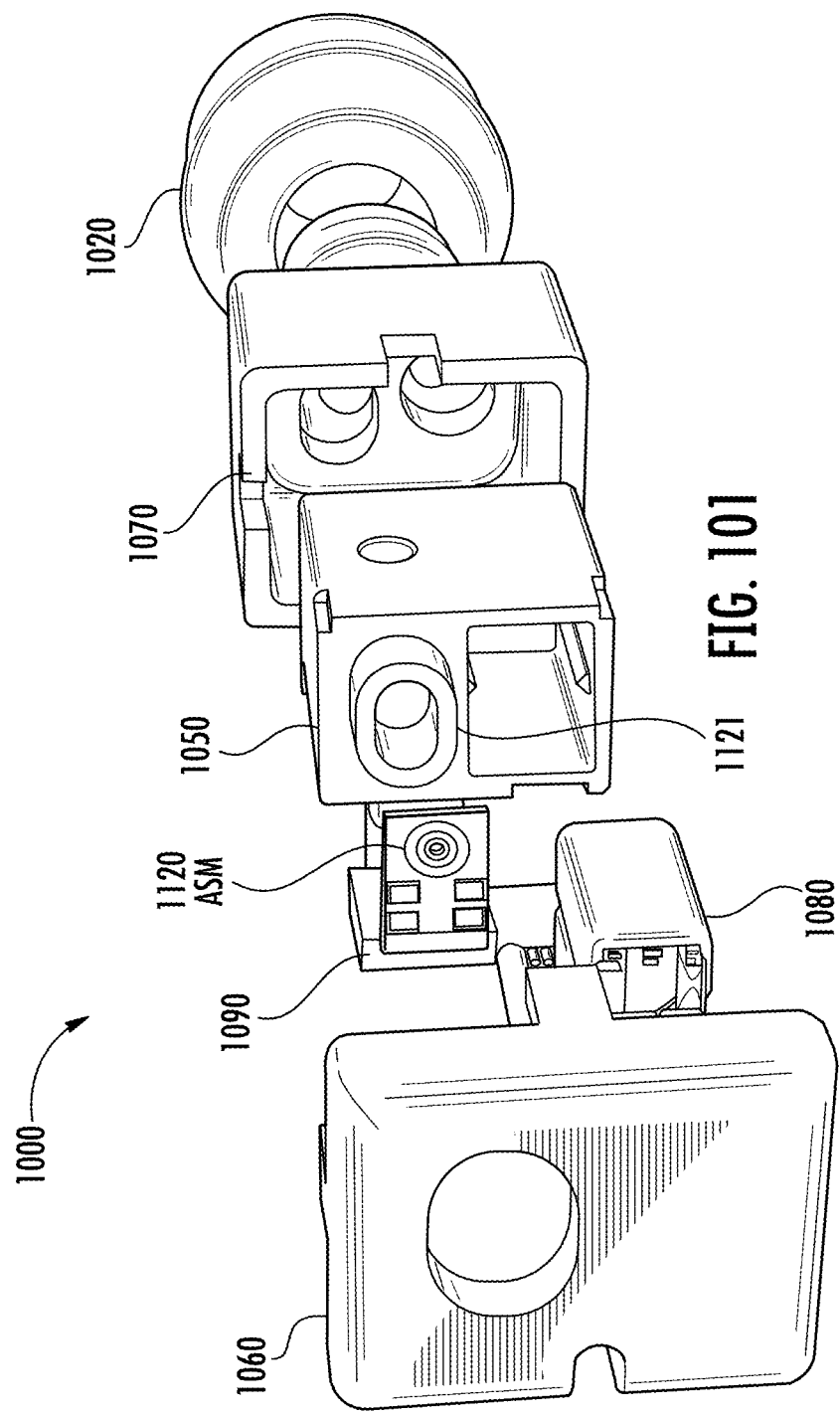

FIG. 101 illustrates an angled back exploded view of an earphone device 1000, which may be configured to include a cap 1060, which may connect with an ambient sound microphone port 1121 of an electronic package housing 1050 of the earphone device 1000. The electronic package housing 1050 may house an electronics package 1090 including an ambient sound microphone 1120 and an ear canal microphone. The electronic package housing 1050 may be inserted into an earphone housing 1070 of the earphone device. An eartip 1020 may be positioned onto a stent of the earphone housing 1070. Each of these components combined together can form the earphone device 1000.

Figure 102:
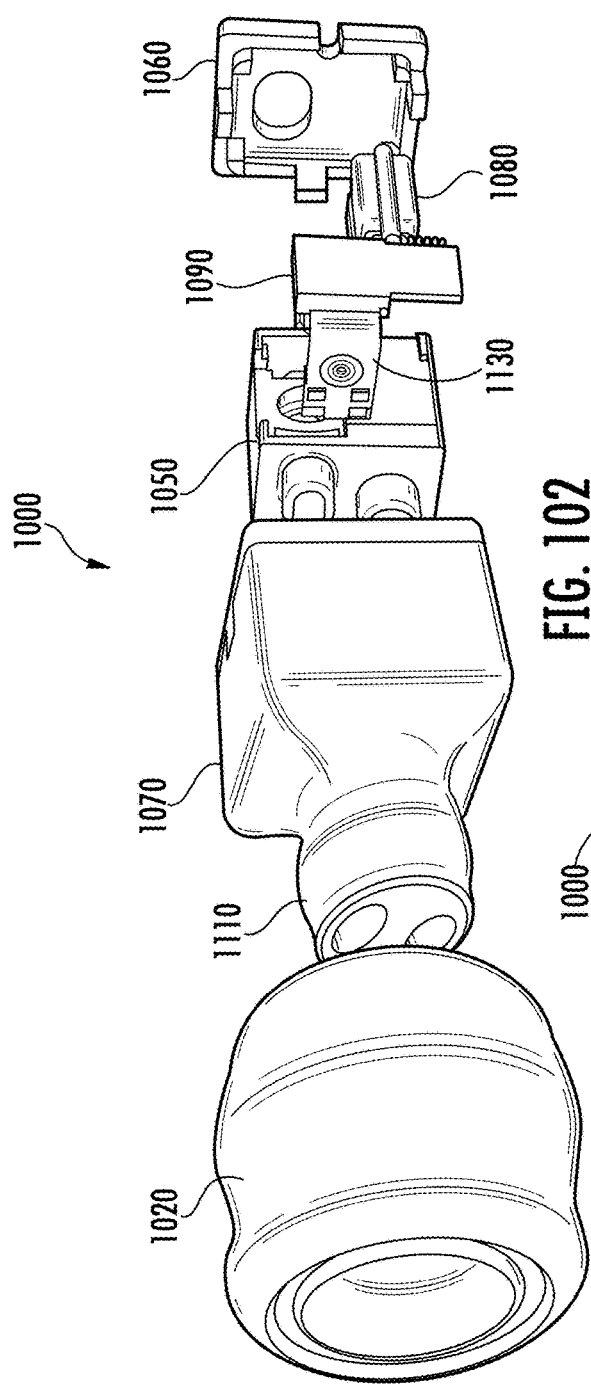

FIG. 102 illustrates an angled front exploded view of an earphone device 1000, which may be configured to include an eartip 1020 that may affix to a stent 1110 of an earphone housing 1070 of the earphone device 1000. The earphone housing 1070 may house an electronic package housing 1050, which may house an electronics package 1090 including an ear canal microphone 1130 and an ambient sound microphone 1120. The earphone device 1000 may further include a speaker 1080, and a cap 1060 for securing the components of the earphone device 1000 together.

Figure 103:
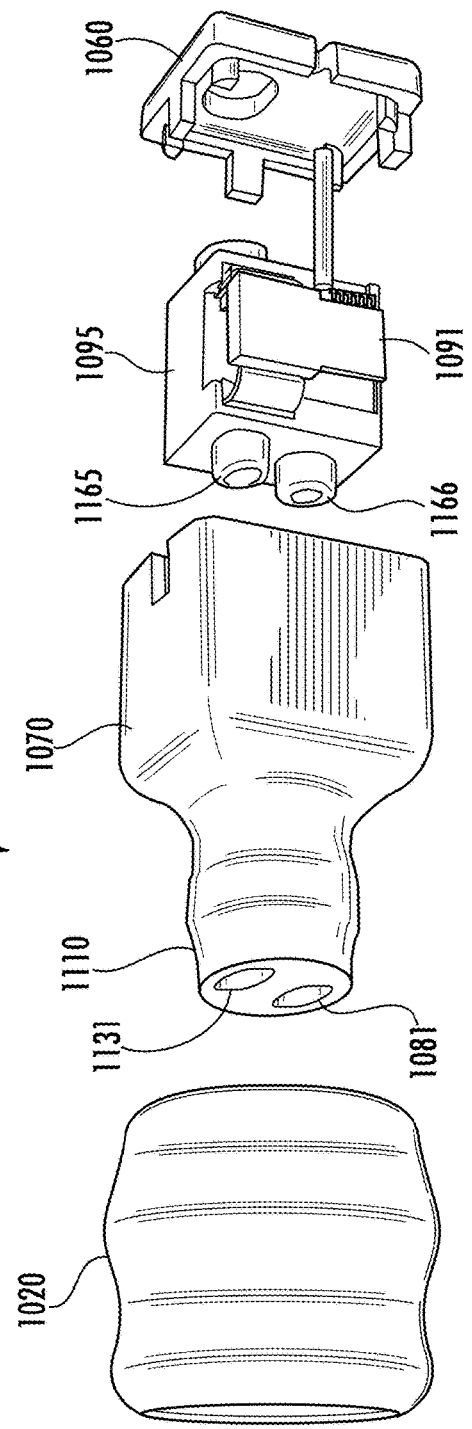

FIG. 103 illustrates an angled bottom exploded view of an earphone device 1000, which may include an eartip 1020 that may be secured to a stent 1110 of an earphone housing 1070. The earphone housing 1070 may connect to an electronics packaging unit 1095, such as by connecting the ear canal acoustic port 1165 to a keyed recess within the ear canal microphone port 1131 and by connecting the speaker acoustic port 1166 to a keyed recess within the speaker port 1081. The electronics packaging unit 1095 may include a flexible circuit 1091 that may couple to an ambient sound microphone 1120 and an ear canal microphone 1130. A cap 1060 may be secured to the underside of the electronics packaging unit 1095 to secure the components of the earphone device 1000 together.

Figure 104:
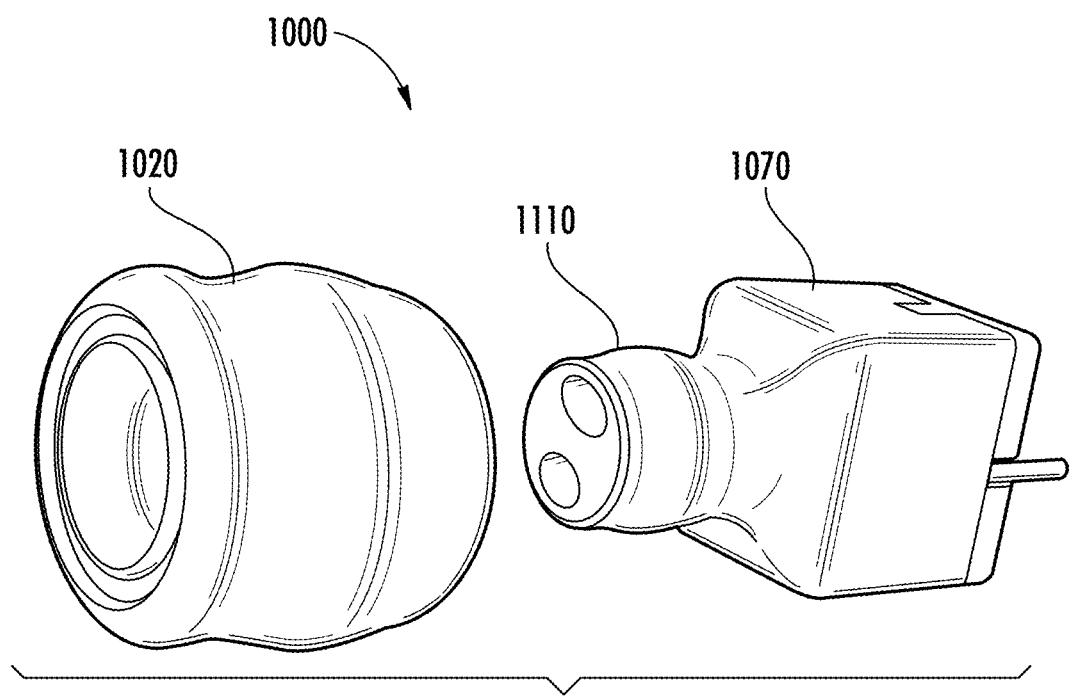
Figure 105:
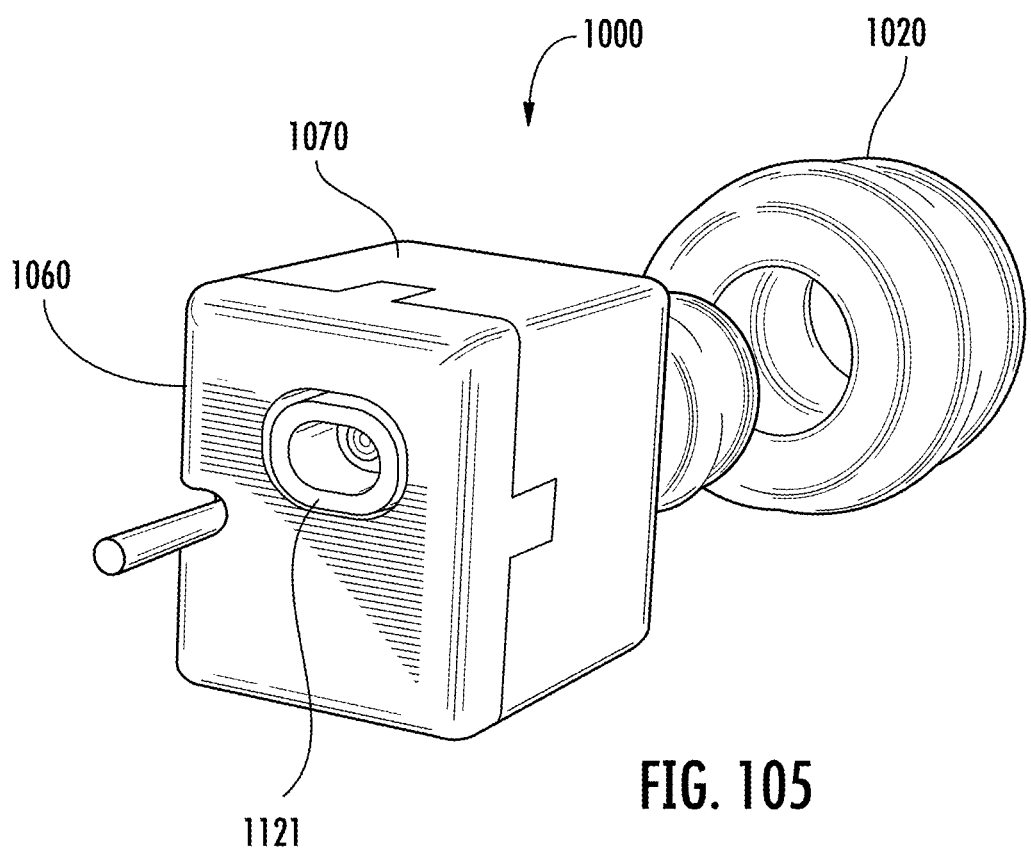

FIG. 104 illustrates an angled front exploded view of an earphone device 1000 that includes an eartip 1020 that may be secured to a stent 1110 of an earphone housing 1070. FIG. 105 illustrates an angled back exploded view of an earphone device 1000 that includes an eartip 1020 that may be secured to an earphone housing 1070. The earphone housing 1070 may be secured to the earphone device 1000 using a cap 1060 may connect with an ambient sound microphone port 1121 of the earphone device 1000.

Figure 106:
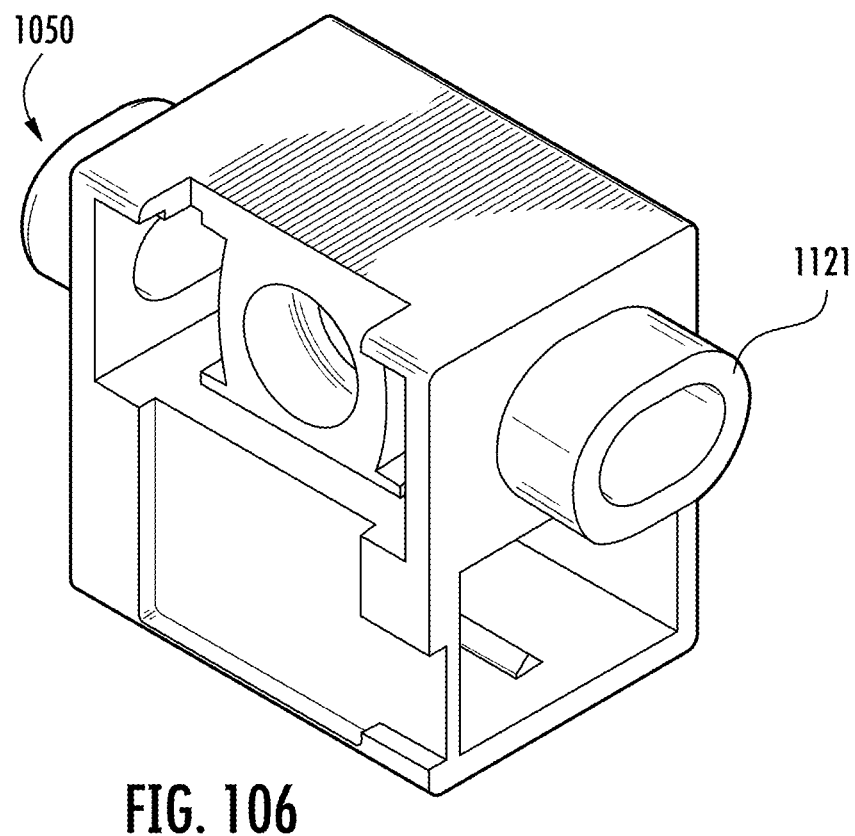

FIG. 106 illustrates an angled rear view of an electronic package housing 1050 for use with an earphone device 1000. The electronic package housing 1050 may include an ambient sound microphone port 1121 that may connect to a cap 1060 of the earphone device 1000, and may serve as channel through which an ambient sound microphone 1120 of the earphone device 1000 can measure and/or capture sound occurring in an ambient environment in a vicinity of the earphone device 1000. The speaker 1080 may also be inserted into the base of the electronic package housing 1050. The electronic package housing 1050 may be configured to isolate the microphones and speakers, and provide a uniform module that can be plugged into multiple designs.

The electronic package housing 1050 may be acoustically sealed after the electronics are inserted into it. For example, Alumilite high strength rubber 3 may be utilized to seal any gaps. Notably, any type of sealant may be utilized, for example, E600 elastic glue and/or UV curable glue.

FIG. 107 illustrates an angled front view of an electronic package housing 1050 for use with an earphone device 1000. The electronic package housing 1050 may include an ear canal microphone acoustic port 1165 and a speaker acoustic port 1166, which may connect to keys 1160 (i.e. keyed recesses) of an earphone housing 1070. The ear canal microphone acoustic port 1165 may serve as a channel through which an ear canal microphone 1130 of the earphone device 1000 can measure sounds occurring in an ear canal of a user. The speaker acoustic port 1166 may serve as a channel through which a speaker 1080 may output sounds to an ear canal of a user.

Testing Data

The earplug 300 provides minimal mean attenuation across frequencies of 10-15 dB to enable software advantages, a comfortable fit allowing hours of wear, and ease of manufacturing. Comfort and attenuation are measured by subjective and objective testing respectively. The ease of manufacturing was accomplished by designing a system that can be molded as a single piece that can then be folded into a final form factor. To examine comfort and attenuation, two substantial tests/studies were performed, an EPA regulated test for attenuation, and a second subjective comfort study. The standardized test for determining cross frequency mean attenuation is the EPAs Noise Reduction Rating. The The subjective goal was to enhance comfort so that a wearer can use the devices herein for prolonged periods of time. A three week comfort study (discussed below) was performed involving standard earphones delivered to volunteers whom swap three different types of eartips (Comply™ Tips (foam), Polymer Single Flange and applicant's AirTips™ eartips) every day comparing the eartips for ease of insertion, perceived pressure exerted against ear canal, comfort, and general usage satisfaction. Each user used the test object for at least a continuous period of two hours in a day, with thirty six usages (6 usages per subject) of each test object over the three week period. The order of use was varied to minimize fatigue bias in the results. In summary, applicant's eartip described herein was more comfortable than the Comply™ foam tip and more comfortable than the single flange polymer tip provided commercially with the earphone.

According to Environmental Protection Agency's (EPA) labeling requirement (Code of Federal Regulations (40 CFR Part 211), ANSI S3.19-1974 is the current testing requirement for hearing protective device labeling. It is an Experimenter-Fit, threshold hearing test for spectral attenuation in 9 frequency bands from 125-8000 Hz, using ten subjects, three tests each subject. The mean attenuation and standard deviations are used to compute an NRR value which can then be placed on the product label. A value of NRR=18 was measured. A surprisingly flat mean attenuation was also measured, providing the added benefit of attenuating frequencies above 3 KHz equally rather than increasing attenuation with increasing frequency. A flat mean attenuation profile maintains frequency integrity of sound being reduced by the attenuating eartip. The NRR testing is summarized in the following table.

| ATTENUATION MEANS AND STANDARD DEVIATIONS (from 30 trials) | | | | | | | | |
|---|---|---|---|---|---|---|---|---|
| ⅓ octave band center (Hz) | 125 | 250 | 500 | 1000 | 2000 | 3350 | 4000 | 6300 | 8000 |
| mean attenuation (dB) | 23.7 | 24.8 | 23.1 | 23.5 | 31.1 | 36.2 | 35.3 | 31.2 | 32.5 |
| standard deviation (dB) | 3.2 | 3.8 | 4.7 | 2.4 | 3.7 | 3.9 | 3.9 | 3.4 | 3.9 |

Comfort Study (six subjects, thirty six usages, at least 2 hour continuous usage):

A third party study subjectively compared the comfort of applicant's eartips on a commercial available earphone (Beyerdynamic iDX 160 iE) for long continuous usage periods (at least two hours of continuous for the day prior to any rating) over multiple weeks (three), and rotating the order of usage of the eartips to minimize potential effect of wearing fatigue on ratings. Table 1 below illustrates the usage order for a particular week, where the order was repeated during the week with a day rest between a usage order change. Each eartip was worn at least thirty six times over a period of three weeks (at least six usages per subject, with six subjects). The eartips tested were: applicant's eartip described herein, third party Comply™ Foam tips, and Beyerdynamic's Single Flange polymer tip which is provided commercially with the earphone upon purchase. The units were evaluated on Beyerdynamic iDX 160 iE earphones.

TABLE 1

Ear Tip Testing Schedule, where the numbers represent eartip type, note that the usage order is repeated for the particular week.

| | Repetition: | | |
|---|---|---|---|
| Participant | 2 Week 1 | 2 Week 2 | 2 Week 3 |
| 1 | 123 | 213 | 321 |
| 2 | 213 | 321 | 312 |
| 3 | 321 | 312 | 231 |
| 4 | 312 | 231 | 132 |
| 5 | 231 | 132 | 123 |
| 6 | 132 | 123 | 213 |

Each object tested was evaluated on a scale from −3 (least favorable) to +3 (most favorable), where after the first rotation (e.g., eartip usage 123 for participant 1) ratings were based upon eartip comparison. FIGS. 108-111 summarize the results with larger values being more favorable, with 95% confidence intervals (CI) plotted. In summary the applicant's AirTips™ eartips exceeded the Comply™ tips in comfort, perceived pressure, overall satisfaction and insertion difficulty.

FIG. 112 sets forth U.S. Environmental Protection Agency (EPA) Noise Reduction Rating (NRR) attenuation test data for an eartip 300. The test results provide a flat profile above 2 kHz and relatively flat from 125 to 2 kHz. Also, the NRR value is 18.

FIG. 113 illustrates the eartip mean attenuation profile in comparison with a market advertised flat attenuation earplug. Most earplugs attenuate more as frequency increases. Ideally, a flat attenuation (mean attenuation constant within standard deviation across frequency) maintains the frequency spectrum of external audio content where the earplug reduces audio content equally across frequency maintaining its frequency shape.

FIGS. 114-116 illustrate an acoustic spectrum which illustrates that the attenuation of occlusion effect eartips is less at frequencies less than 500 Hz which lets frequencies pass through the eartip to the outside ambient environment reducing the resonance in frequencies less than 500 Hz and reducing the occlusion effect.

Methods of Manufacturing

The Eartip (eartip) can be fabricated by various means, for example injection molding, then sealed with various filler mediums (e.g. gas, liquid, gel), and inserted upon a stent, for example the eartip can have an extension portion that slides over the stent.

For example specific materials may not be listed for achieving each of the targeted properties discussed, however one of ordinary skill would be able, without undo experimentation, to determine the materials needed given the enabling disclosure herein. For example Elastosil™ 30A, 70A, High Strength 1, 2, 3, Moldmaking Rubber (Alumilite™ products), flexible 3D printable material, silicon, urethane, natural and synthetic rubber, high strength rubber, chloroprene rubber, EVA rubber, quartz fiber, can be used; however, any material that can be used within the ear canal can be used for eartips and any material that can be used for earphones (silicon, urethane, rubber, plastic, Elastosil, metal, wood, and the like) can be used in the earphone housing and components thereof. As discussed herein, the eartips can be printed on three dimensional printers while provided the Shore A hardness discussed herein. Various material can also be used for the EPH, for example tough resin (FormLabs) if printed and any other materials, as mentioned if molded. Typical durometer for the in ear portions can be from shore A of 5-40.

The eartips can be formed as an inverted shape mold as discussed herein. As an example, the inverted mold can be formed as a partial cylindrical sleeve with the shapes and arrangements disclosed herein. Such manufacturing provides great advantages of reduced cost without sacrificing performance of the eartips. As disclosed, the inverted shape mold allows the user to folder over portions of the eartip to use the eartip. Such eartips can provide the performance disclosed herein while being designed to be disposable.

FIG. 117 shows a flow diagram of method 1300 of forming an eartip or earplug. At block 1302, a mold of an unfolded shape of an eartip can be formed. The mold can be formed from any suitable material, such as those disclosed herein. After the mold is formed at block 1302, eartips and/or earplugs can be formed without performing the step set forth in block 1302. At block 1304, a flexible material can be provided to the mold. At block 1306, the flexible material can sit for a threshold time and/or temperature for curing to form an inverted eartip that can be curved.

At step 1308, the cured inverted eartip can be removed. Here, no further processing of the cured inverted eartip is required. Optionally at step 1308, at least a portion of the inverted eartip can be folded to form a final, useable, or insertable eartip.

Computing System for Facilitating the Operation and Functionality of the System

Referring now also to FIG. 118, at least a portion of the methodologies and techniques described with respect to the exemplary embodiments of the system 100 can incorporate a machine, such as, but not limited to, computer system 14100, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, by providing functionality and/or programs for facilitating the operative functionality of the earphone devices 115, 130, and/or the first, second, third, fourth, and fifth user devices 102, 106, 110, 121, 125 and/or the earphone devices 115, 130, by providing functionality and/or programs for facilitating operation of any of the components of the earphone devices 115, 130 (e.g. ear canal receivers, transceivers, ear canal microphones, ambient sound microphones, or by assisting with any other operations conducted by or within the system 100.

In some embodiments, the machine may operate as a standalone device. In some embodiments, the machine may be connected (e.g., using communications network 135, the communications network 116, the communications network 131, another network, or a combination thereof) to and assist with operations performed by other machines and systems, such as, but not limited to, the first user device 102, the second user device 111, the third user device 110, the fourth user device 121, the fifth user device 125, the earphone device 115, the earphone device 130, the server 140, the server 150, the database 155, the server 160, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 14100 may include a processor 14102 (e.g., a central processing unit (CPU), a graphics processing unit (GPU, or both), a main memory 14104 and a static memory 14106, which communicate with each other via a bus 14108. The computer system 14100 may further include a video display unit 14110, which may be, but is not limited to, a liquid crystal display (LCD), a flat panel, a solid state display, or a cathode ray tube (CRT). The computer system 14100 may include an input device 14112, such as, but not limited to, a keyboard, a cursor control device 14114, such as, but not limited to, a mouse, a disk drive unit 14116, a signal generation device 14118, such as, but not limited to, a speaker or remote control, and a network interface device 14120.

The disk drive unit 14116 may include a machine-readable medium 14122 on which is stored one or more sets of instructions 14124, such as, but not limited to, software embodying any one or more of the methodologies or functions described herein, including those methods illustrated above. The instructions 14124 may also reside, completely or at least partially, within the main memory 14104, the static memory 14106, or within the processor 14102, or a combination thereof, during execution thereof by the computer system 14100. The main memory 14104 and the processor 14102 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 14122 containing instructions 14124 so that a device connected to the communications network 135, the communications network 116, the communications network 131, another network, or a combination thereof, can send or receive voice, video or data, and communicate over the communications network 135, the communications network 116, the communications network 131, another network, or a combination thereof, using the instructions. The instructions 14124 may further be transmitted or received over the communications network 135, another network, or a combination thereof, via the network interface device 14120.

While the machine-readable medium 14122 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. An eartip comprising:
   an outer portion; and
   an inner portion, wherein the inner portion has at least one sizing structure, wherein a first section of the outer portion is designed to contact the ear canal, and wherein the inner portion is configured to receive a stent, wherein the at least one sizing structure is flexible and is designed to flex to accept various outside diameters of a stent.

2. The eartip according to claim 1, where the outer portion is either flexible polymer or foam.

3. The eartip according to claim 2, where the outer portion includes a tip.

4. The eartip according to claim 3, where the tip rests against a portion of a first ridge or a second portion of a second ridge creating the contact area.

5. The eartip according to claim 3, where a portion of the tip contacts the inner portion when the eartip is inserted upon the stent or inserted into an ear canal.

6. An eartip comprising:
   an outer portion; and
   an inner portion, wherein the inner portion has at least one structure, wherein a first section of the outer portion is designed to contact the ear canal, and wherein the inner portion is configured to receive a stent, wherein the at least one structure is flexible and is designed to accept various outside diameters of a stent, wherein a first portion of the outer portion contacts a first ridge when the eartip is inserted upon a stent or inserted into an ear canal.

7. The eartip of any of claims 1 to 3, further comprising a lip extending from the inner portion.

8. The eartip of any of claims 1 to 5, further comprises of a material with a material property between 2 Shore A to 90 Shore A.

9. The eartip of any of claims 1 to 5, wherein the eartip forms an earplug with a mean attenuation between 15 dB to 36 dB.

* * * * *